US005213605A

United States Patent [19]

Rueb et al.

[11] Patent Number: 5,213,605

[45] Date of Patent: May 25, 1993

[54] N-ARYLTETRAHYDROPHTHALIMIDE COMPOUNDS

[75] Inventors: Lothar Rueb, Speyer; Karl Eicken, Wachenheim; Peter Plath, Frankenthal; Barbara Schwalge, Ludwigshafen; Karl-Otto Westphalen, Speyer; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 761,187

[22] Filed: Sep. 17, 1991

Related U.S. Application Data

[63] Continuation of Ser. No. 464,639, Jan. 5, 1990, Pat. No. 5,080,710, which is a continuation of Ser. No. 315,128, Feb. 24, 1989, abandoned.

[30] Foreign Application Priority Data

Mar. 5, 1988 [DE] Fed. Rep. of Germany ....... 3807295

[51] Int. Cl.[5] .................. C07D 413/10; C07D 417/10; A01N 43/76; A01N 43/78

[52] U.S. Cl. .................................. 504/267; 548/159; 548/221; 504/270

[58] Field of Search .................... 548/159, 221; 71/90, 71/95

[56] References Cited

U.S. PATENT DOCUMENTS 5,007,952 4/1991 Kume .................................... 71/73
5,077,401 12/1991 Kume .................................... 544/52

Primary Examiner—Robert Gerstl
Attorney, Agent, or Firm—Keil & Weinkauf

[57] ABSTRACT

N-aryltetrahydrophthalimide compounds of the general formula I

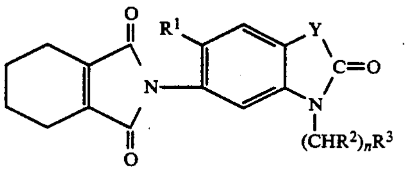

I where n, $R^1$, Y, $R^2$ and $R^3$ have the meanings stated in the claims and description, and a method for controlling undesirable plant growth.

12 Claims, No Drawings

N-ARYLTETRAHYDROPHTHALIMIDE COMPOUNDS

This is a continuation of application Ser. No. 464,639, filed Jan. 5, 1990, U.S. Pat. No. 5,080,710 which is a continuation of Ser. No. 315,128, filed Feb. 24, 1989, now abandoned.

The present invention relates to N-phenyltetrahydrophthalimide compounds of the general formula I

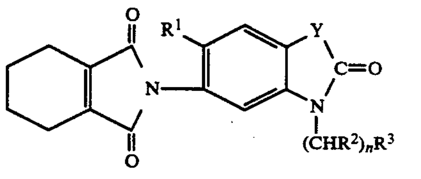

I where the substituents and indices have the following meanings: n is 0 or 1, $R^1$ is hydrogen or halogen, Y is —O—, —S—, —$CH_2$—, —S—$CR^4R^5$—, —O—$CR^4R^5$— or —$CH_2$—$CR^4R^5$—, $R^4$ and $R^5$ independently of one another being hydrogen or $C_1$-$C_3$-alkyl, $R^2$ is hydrogen or $C_1$-$C_3$-alkyl, $R^3$ is a saturated or monounsaturated 5-membered or 6-membered ring which has an oxygen or sulfur atom in the ring and may be monosubstituted to trisubstituted by $C_1$-$C_3$-alkyl, or $R^3$ is phenyl which is unsubstituted or monosubstituted to trisubstituted by $C_1$- or $C_2$-alkyl, halogen, methoxy, nitro and/or cyano, and, if n is 0 and Y is —$CH_2$—, —$CH_2$—$CR^4R^5$— or —S—$CR^4R^5$—, $R^3$ may furthermore be hydrogen, $C_1$-$C_5$-alkyl, $C_3$- or $C_4$-alkenyl, $C_3$- or $C_4$-alkynyl, $C_1$-$C_4$-haloalkyl, $C_3$- or $C_4$-haloalkenyl, $C_1$- or $C_2$-alkoxy-$C_1$- or $C_2$-alkyl or $C_1$- or $C_2$-alkoxy-$C_1$-or $C_2$-alkoxy-$C_1$- or $C_2$-alkyl or $C_1$-$C_6$-alkoxycarbonyl-substituted $C_1$-$C_3$-alkyl.

The present invention furthermore relates to a method for controlling undesirable plant growth and herbicides which contain these compounds.

N-aryl-substituted tetrahydrophthalimides having a herbicidal action are known. For example, EP-A-170 191 describes tetrahydrophthalimides, but their activity is unsatisfactory at low application rates.

It is an object of the present invention to provide appropriately improved tetrahydrophthalimide compounds.

We have found that this object is achieved in that the N-aryltetrahydrophthalimide compounds of the formula I which were defined at the outset have an advantageous herbicidal action, particularly by the postemergence method, and are selective with respect to a number of crops. Where these compounds are capable of forming stereoisomers, the invention relates to all isomers.

The compounds I are obtained, for example, by first reacting an appropriately substituted aniline of the formula II in a conventional manner in an inert organic solvent with an N-alkylating compound Z—$(CHR^2)_nR^3$ to give the aniline derivative III and then condensing this in an inert organic solvent with 3,4,5,6-tetrahydrophthalic anhydride to give the N-aryltetrahydrophthalimide I.

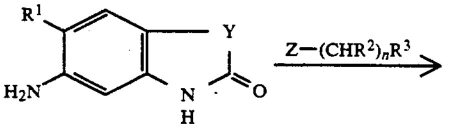

II

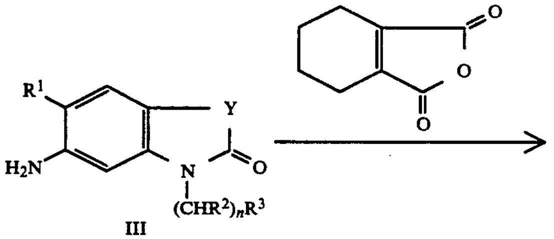

III

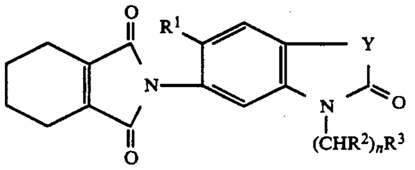

I

The radical Z in the alkylating reagent is a nucleophilic leaving group conventionally used in organic chemistry, such as halogen, e.g. chlorine, bromine or iodine, or sulfonyl, such as toluenesulfonyl or mesyl.

The alkylation is carried out in a conventional manner at up to 200° C., preferably from 0° to 150° C., in an aprotic polar solvent (e.g. acetone, acetonitrile or dimethylformamide), in the presence of a base (e.g. potassium carbonate, sodium hydroxide or sodium hydride).

The condensation of the aniline derivative III with 3,4,5,6-tetrahydrophthalic anhydride is carried out in a protic solvent, such as acetic acid, propionic acid or isobutyric acid, or in an aprotic solvent, such as toluene, xylene or dimethylformamide. The reaction is carried out, as a rule, at from 25° to 200° C., preferably from 70° to 140° C. When an aprotic solvent is used, it is advisable to remove the water continuously.

However, the compounds I are also obtained if an amine II is first condensed with 3,4,5,6-tetrahydrophthalic anhydride to give the N-phenyltetrahydrophthalimide IV, and the latter is then reacted with an N-alkylating compound Z—$(CHR^2)_nR^3$ to give I.

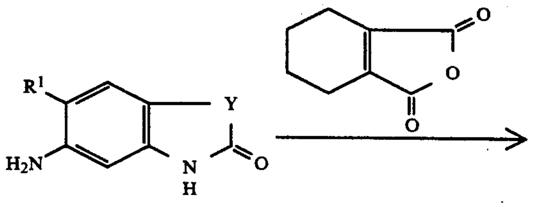

II

-continued

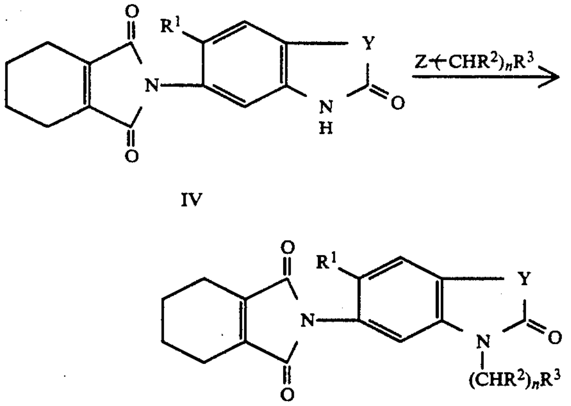

IV

I

These reactions are carried out under conditions similar to those described above.

The required compounds II are prepared in a conventional manner: S. Gabriel et al., Chem. Ber. 12 (1879), 600; W. A. Sexton, J. Chem. Soc. 1939, 470; D. R. Shridar et al., Synthesis 1982, 986; Sandmeyer, Chem. Ber. 19 (1886), 2656, and D. R. Shridar et al., Indian. J. Chem. 24B (1985), 1263.

For the use of the compounds I in accordance with regulations, the following radicals are preferred substituents.

Halogen as used above is fluorine, chlorine or bromine, halogen radicals $R^1$ preferably being fluorine.

Alkyl includes branched and straight-chain radicals, e.g. methyl, ethyl, n-propyl and isopropyl.

The alkenyl and alknyl radicals may likewise be branched or straight-chain. Examples of alkenyl radicals in formula I are allyl, 2-propenyl, 2-butenyl, 3-butenyl and 2-isobutenyl, in particular allyl and 2-butenyl, and alkynyl radicals are, as a rule, propargyl, 2-butynyl or 3-butynyl.

The five-membered or six-membered heterocyclic ring of the formula I is preferably a hydrogenated or partially hydrogenated furan, thiophene, pyran or thiopyran ring.

Phenyl preferably includes the unsubstituted and monosubstituted derivatives, e.g. chlorophenyl, methylphenyl and methoxyphenyl.

The N-substituted tetrahydrophthalimides are obtainable from 3,4,5,6-tetrahydrophthalic anhydride and an appropriate aniline of the formula III, for example in a solvent at from 20° to 200° C., preferably from 40° to 150° C. Suitable solvents are, for example, lower alkanoic acids, such as glacial acetic acid or propionic acid, or aprotic solvents, such as toluene or xylene, in the presence of an acidic catalyst, for example an aromatic sulfonic acid.

Preferred compounds I are those in which $R^1$ is hydrogen or fluorine, $R^4$ and $R^5$ are each hydrogen or methyl, $R^2$ is hydrogen and $R^3$ is 2- or 3-tetrahydrofuryl, 2- or 3-tetrahydrothienyl, 2-, 3- or 4-tetrahydropyranyl, 2-, 3- or 4-tetrahydrothiopyranyl, 5,6-dihydro-2H-pyranyl or 5,6-dihydro-2H-thiopyranyl.

Particularly active novel compounds are listed in Tables I, II, IIa, III, IIIa, IV, IVa, V and VI below.

TABLE I

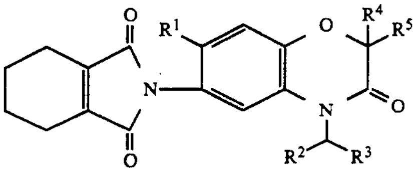

| $R^1$ | $R^2$ | $R^3$ | $R^4$ | $R^5$ |
|---|---|---|---|---|
| H | H | 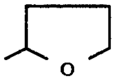 | H | H |
| F | H | 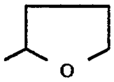 | H | H |
| H | $CH_3$ | 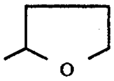 | H | H |
| F | $CH_3$ | 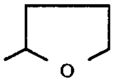 | H | H |
| H | H | 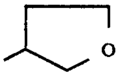 | H | H |
| F | H | 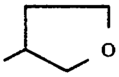 | H | H |
| H | $CH_3$ | 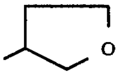 | H | H |
| F | $CH_3$ | 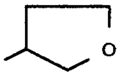 | H | H |
| H | H | 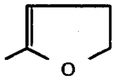 | H | H |
| F | H | 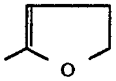 | H | H |
| H | $CH_3$ | 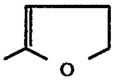 | H | H |
| F | $CH_3$ | 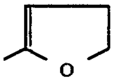 | H | H |
| H | H | 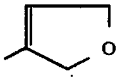 | H | H |
| F | H | 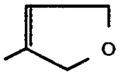 | H | H |

TABLE I-continued
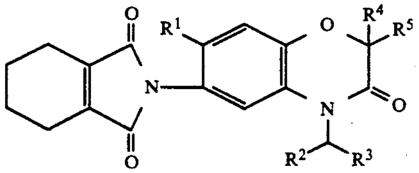
| R1 | R2 | R3 | R4 | R5 |
|---|---|---|---|---|
| H | CH3 | 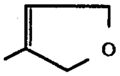 | H | H |
| F | CH3 | 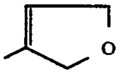 | H | H |
| H | H | 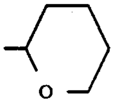 | H | H |
| F | H | 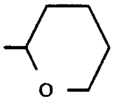 | H | H |
| H | CH3 | 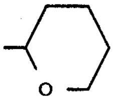 | H | H |
| F | CH3 | 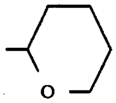 | H | H |
| H | H | 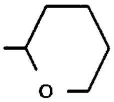 | CH3 | H |
| F | H | 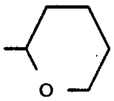 | CH3 | H |
| H | CH3 | 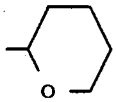 | CH3 | H |
| F | CH3 | 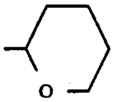 | CH3 | H |
| H | H | 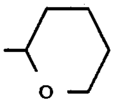 | CH3 | CH3 |
| F | H | 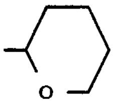 | CH3 | CH3 |
TABLE I-continued
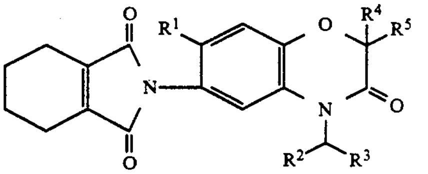
| R1 | R2 | R3 | R4 | R5 |
|---|---|---|---|---|
| H | CH3 | 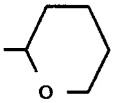 | CH3 | CH3 |
| F | CH3 | 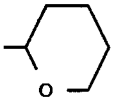 | CH3 | CH3 |
| H | H | 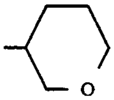 | H | H |
| F | H | 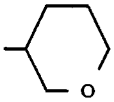 | H | H |
| H | CH3 | 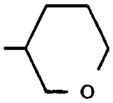 | H | H |
| F | CH3 | 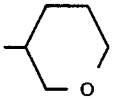 | H | H |
| H | H | 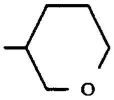 | CH3 | H |
| F | H | 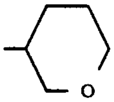 | CH3 | H |
| H | CH3 | 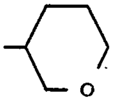 | CH3 | H |
| F | CH3 | 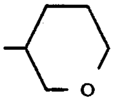 | CH3 | H |
| H | H | 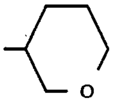 | CH3 | CH3 |

TABLE I-continued
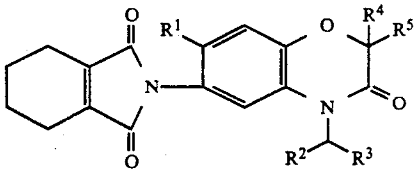
| $R^1$ | $R^2$ | $R^3$ | $R^4$ | $R^5$ |
|---|---|---|---|---|
| F | H | 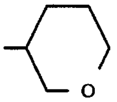 | $CH_3$ | $CH_3$ |
| H | $CH_3$ | 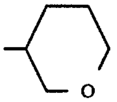 | $CH_3$ | $CH_3$ |
| F | $CH_3$ | 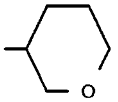 | $CH_3$ | $CH_3$ |
| H | H | 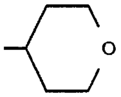 | H | H |
| F | H | 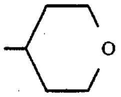 | H | H |
| H | $CH_3$ | 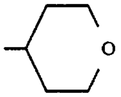 | H | H |
| F | $CH_3$ | 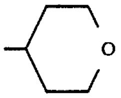 | H | H |
| H | H | 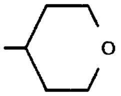 | $CH_3$ | H |
| F | H | 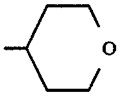 | $CH_3$ | H |
| H | $CH_3$ | 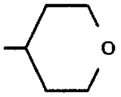 | $CH_3$ | H |
| F | $CH_3$ | 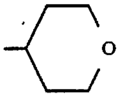 | $CH_3$ | H |
TABLE I-continued
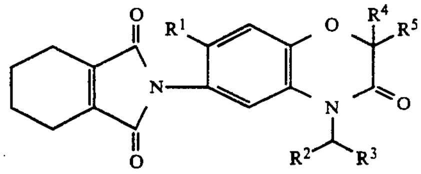
| $R^1$ | $R^2$ | $R^3$ | $R^4$ | $R^5$ |
|---|---|---|---|---|
| H | H | 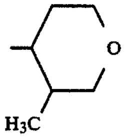 | H | H |
| F | H | 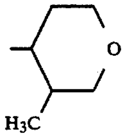 | H | H |
| H | $CH_3$ | 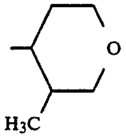 | H | H |
| F | $CH_3$ | 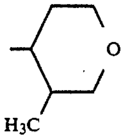 | H | H |
| H | H | 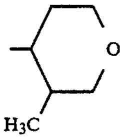 | $CH_3$ | H |
| F | H | 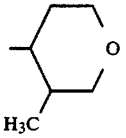 | $CH_3$ | H |
| H | $CH_3$ | 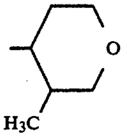 | $CH_3$ | H |
| F | $CH_3$ | 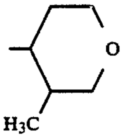 | $CH_3$ | H |
| H | H | 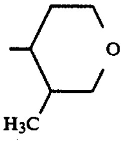 | $CH_3$ | $CH_3$ |

TABLE I-continued
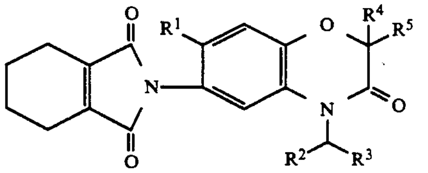
| $R^1$ | $R^2$ | $R^3$ | $R^4$ | $R^5$ |
|---|---|---|---|---|
| F | H | 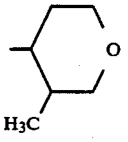 | $CH_3$ | $CH_3$ |
| H | $CH_3$ | 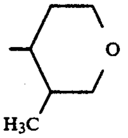 | $CH_3$ | $CH_3$ |
| F | $CH_3$ | 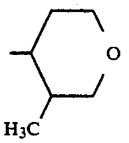 | $CH_3$ | $CH_3$ |
| H | H | 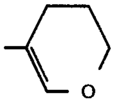 | H | H |
| F | H | 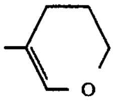 | H | H |
| H | $CH_3$ | 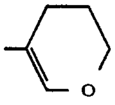 | H | H |
| F | $CH_3$ | 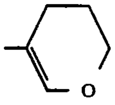 | H | H |
| H | H | 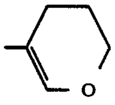 | $CH_3$ | H |
| F | H | 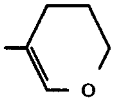 | $CH_3$ | H |
| H | $CH_3$ | 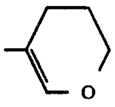 | $CH_3$ | H |
TABLE I-continued
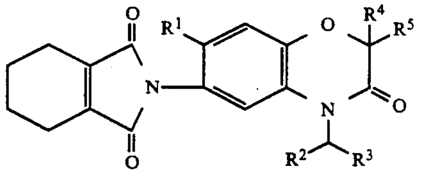
| $R^1$ | $R^2$ | $R^3$ | $R^4$ | $R^5$ |
|---|---|---|---|---|
| F | $CH_3$ | 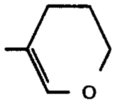 | $CH_3$ | H |
| H | H | 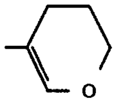 | $CH_3$ | $CH_3$ |
| F | H | 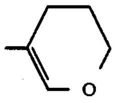 | $CH_3$ | $CH_3$ |
| H | $CH_3$ | 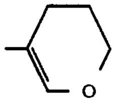 | $CH_3$ | $CH_3$ |
| F | $CH_3$ | 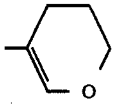 | $CH_3$ | $CH_3$ |
| H | H | 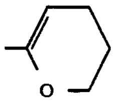 | $CH_3$ | $CH_3$ |
| F | H | 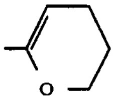 | $CH_3$ | $CH_3$ |
| H | $CH_3$ | 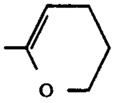 | $CH_3$ | $CH_3$ |
| F | $CH_3$ | 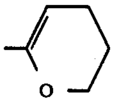 | $CH_3$ | $CH_3$ |
| H | H | 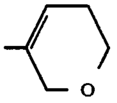 | H | H |
| F | H | 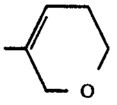 | H | H |

TABLE I-continued
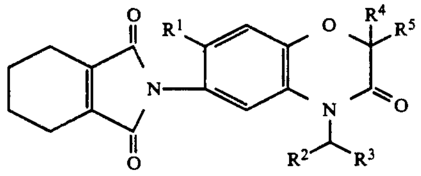
| $R^1$ | $R^2$ | $R^3$ | $R^4$ | $R^5$ |
|---|---|---|---|---|
| H | $CH_3$ | 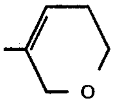 | H | H |
| F | $CH_3$ | 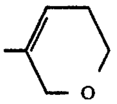 | H | H |
| H | H | 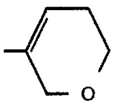 | $CH_3$ | H |
| F | H | 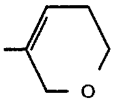 | $CH_3$ | H |
| H | $CH_3$ | 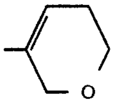 | $CH_3$ | H |
| F | $CH_3$ | 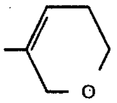 | $CH_3$ | H |
| H | H | 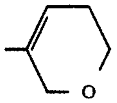 | $CH_3$ | $CH_3$ |
| F | H | 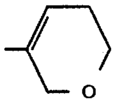 | $CH_3$ | $CH_3$ |
| H | $CH_3$ | 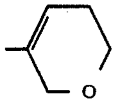 | $CH_3$ | $CH_3$ |
| F | $CH_3$ | 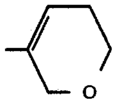 | $CH_3$ | $CH_3$ |
| H | H | 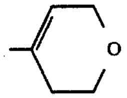 | H | H |
TABLE I-continued
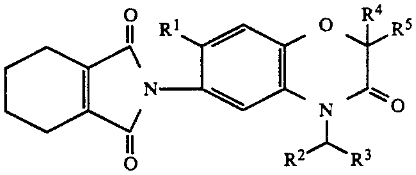
| $R^1$ | $R^2$ | $R^3$ | $R^4$ | $R^5$ |
|---|---|---|---|---|
| F | H | 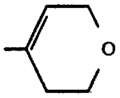 | H | H |
| H | $CH_3$ | 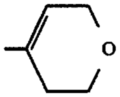 | H | H |
| F | $CH_3$ | 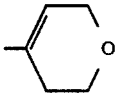 | H | H |
| H | H | 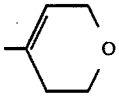 | $CH_3$ | H |
| F | H | 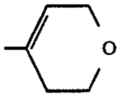 | $CH_3$ | H |
| H | $CH_3$ | 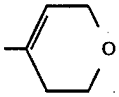 | $CH_3$ | H |
| F | $CH_3$ | 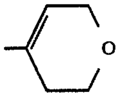 | $CH_3$ | H |
| H | H | 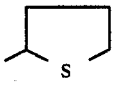 | H | H |
| F | H | 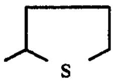 | H | H |
| H | $CH_3$ | 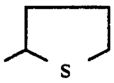 | H | H |
| F | $CH_3$ | 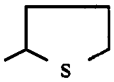 | H | H |
| H | H | 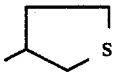 | H | H |
| F | H | 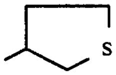 | H | H |

TABLE I-continued
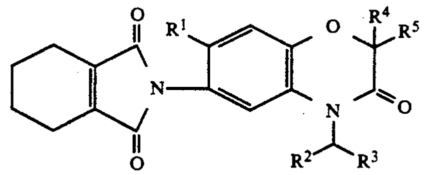
| $R^1$ | $R^2$ | $R^3$ | $R^4$ | $R^5$ |
|---|---|---|---|---|
| H | $CH_3$ | 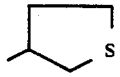 | H | H |
| F | $CH_3$ | 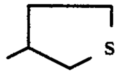 | H | H |
| H | H | 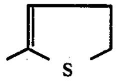 | H | H |
| F | H | 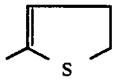 | H | H |
| H | $CH_3$ | 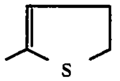 | H | H |
| F | $CH_3$ | 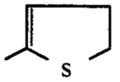 | H | H |
| H | H | 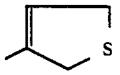 | H | H |
| F | H | 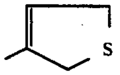 | H | H |
| H | $CH_3$ | 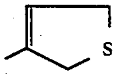 | H | H |
| F | $CH_3$ | 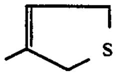 | H | H |
| H | H | 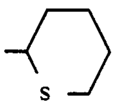 | H | H |
| F | H | 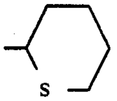 | H | H |
| H | $CH_3$ | 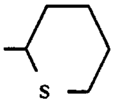 | H | H |
TABLE I-continued
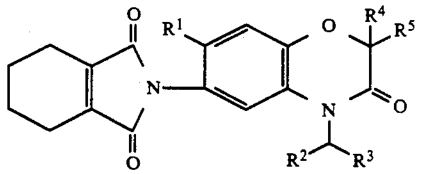
| $R^1$ | $R^2$ | $R^3$ | $R^4$ | $R^5$ |
|---|---|---|---|---|
| F | $CH_3$ | 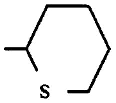 | H | H |
| H | H | 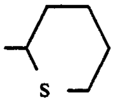 | $CH_3$ | H |
| F | H | 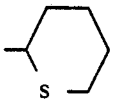 | $CH_3$ | H |
| H | $CH_3$ | 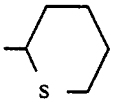 | $CH_3$ | H |
| F | $CH_3$ | 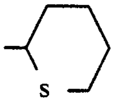 | $CH_3$ | H |
| H | H | 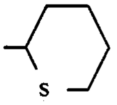 | $CH_3$ | $CH_3$ |
| F | H | 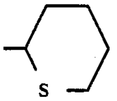 | $CH_3$ | $CH_3$ |
| H | $CH_3$ | 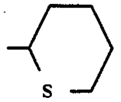 | $CH_3$ | $CH_3$ |
| F | $CH_3$ | 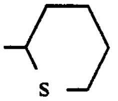 | $CH_3$ | $CH_3$ |
| H | H | 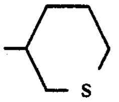 | H | H |
| F | H | 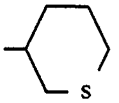 | H | H |

TABLE I-continued
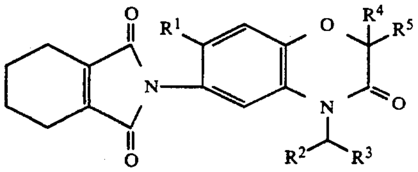
| $R^1$ | $R^2$ | $R^3$ | $R^4$ | $R^5$ |
|---|---|---|---|---|
| H | $CH_3$ | 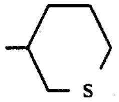 | H | H |
| F | $CH_3$ | 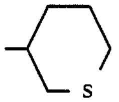 | H | H |
| H | H | 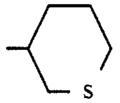 | $CH_3$ | H |
| F | H | 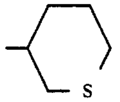 | $CH_3$ | H |
| H | $CH_3$ | 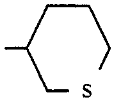 | $CH_3$ | H |
| F | $CH_3$ | 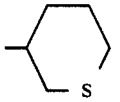 | $CH_3$ | H |
| H | H | 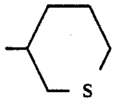 | $CH_3$ | $CH_3$ |
| F | H | 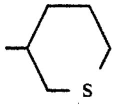 | $CH_3$ | $CH_3$ |
| H | $CH_3$ | 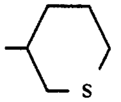 | $CH_3$ | $CH_3$ |
| F | $CH_3$ | 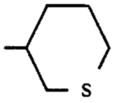 | $CH_3$ | $CH_3$ |
| H | H | 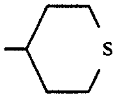 | H | H |
TABLE I-continued
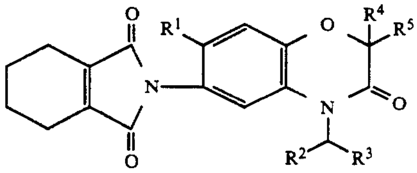
| $R^1$ | $R^2$ | $R^3$ | $R^4$ | $R^5$ |
|---|---|---|---|---|
| F | H | 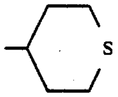 | H | H |
| H | $CH_3$ | 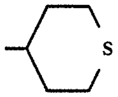 | H | H |
| F | $CH_3$ | 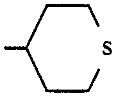 | H | H |
| H | H | 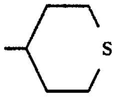 | $CH_3$ | H |
| F | H | 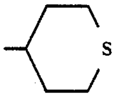 | $CH_3$ | H |
| H | $CH_3$ | 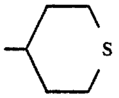 | $CH_3$ | H |
| F | $CH_3$ | 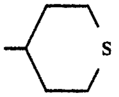 | $CH_3$ | H |
| H | H | 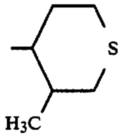 | H | H |
| F | H | 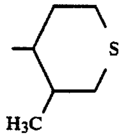 | H | H |
| H | $CH_3$ | 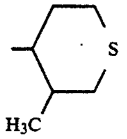 | H | H |

TABLE I-continued
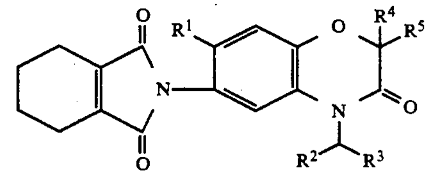
| R¹ | R² | R³ | R⁴ | R⁵ |
|---|---|---|---|---|
| F | $CH_3$ | 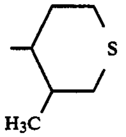 | H | H |
| H | H | 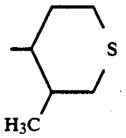 | $CH_3$ | H |
| F | H | 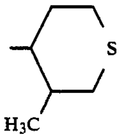 | $CH_3$ | H |
| H | $CH_3$ | 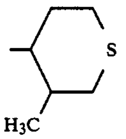 | $CH_3$ | H |
| F | $CH_3$ | 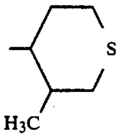 | $CH_3$ | H |
| H | H | 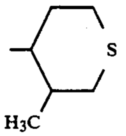 | $CH_3$ | $CH_3$ |
| F | H | 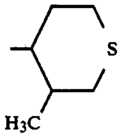 | $CH_3$ | $CH_3$ |
| H | $CH_3$ | 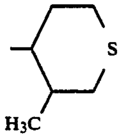 | $CH_3$ | $CH_3$ |
| F | $CH_3$ | 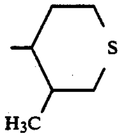 | $CH_3$ | $CH_3$ |
TABLE I-continued
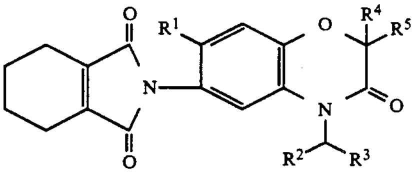
| R¹ | R² | R³ | R⁴ | R⁵ |
|---|---|---|---|---|
| H | H | 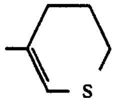 | H | H |
| F | H | 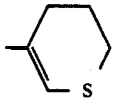 | H | H |
| H | $CH_3$ | 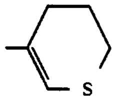 | H | H |
| F | $CH_3$ | 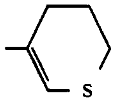 | H | H |
| H | H | 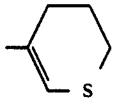 | $CH_3$ | H |
| F | H | 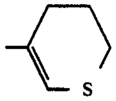 | $CH_3$ | H |
| H | $CH_3$ | 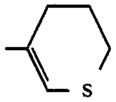 | $CH_3$ | H |
| F | $CH_3$ | 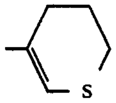 | $CH_3$ | H |
| H | H | 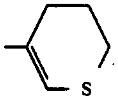 | $CH_3$ | $CH_3$ |
| F | H | 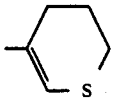 | $CH_3$ | $CH_3$ |
| H | $CH_3$ | 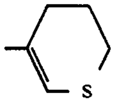 | $CH_3$ | $CH_3$ |

TABLE I-continued
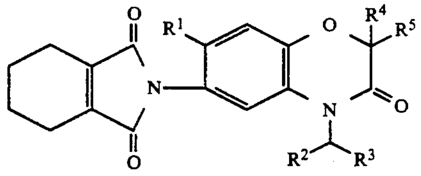
| $R^1$ | $R^2$ | $R^3$ | $R^4$ | $R^5$ |
|---|---|---|---|---|
| F | $CH_3$ | 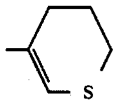 | $CH_3$ | $CH_3$ |
| H | H | 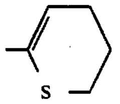 | $CH_3$ | $CH_3$ |
| F | H | 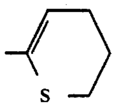 | $CH_3$ | $CH_3$ |
| H | $CH_3$ | 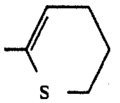 | $CH_3$ | $CH_3$ |
| F | $CH_3$ | 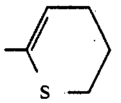 | $CH_3$ | $CH_3$ |
| H | H | 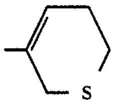 | H | H |
| F | H | 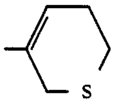 | H | H |
| H | $CH_3$ | 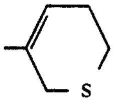 | H | H |
| F | $CH_3$ | 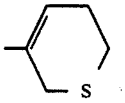 | H | H |
| H | H | 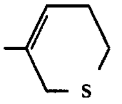 | $CH_3$ | H |
| F | H | 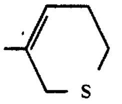 | $CH_3$ | H |
TABLE I-continued
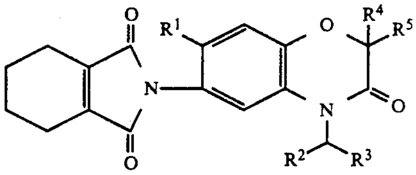
| $R^1$ | $R^2$ | $R^3$ | $R^4$ | $R^5$ |
|---|---|---|---|---|
| H | $CH_3$ | 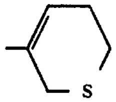 | $CH_3$ | H |
| F | $CH_3$ | 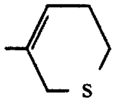 | $CH_3$ | H |
| H | H | 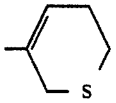 | $CH_3$ | $CH_3$ |
| F | H | 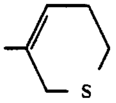 | $CH_3$ | $CH_3$ |
| H | $CH_3$ | 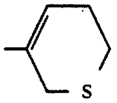 | $CH_3$ | $CH_3$ |
| F | $CH_3$ | 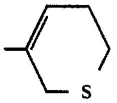 | $CH_3$ | $CH_3$ |
| H | H | 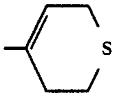 | H | H |
| F | H | 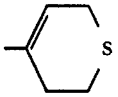 | H | H |
| H | $CH_3$ | 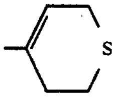 | H | H |
| F | $CH_3$ | 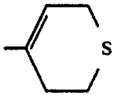 | H | H |
| H | H | 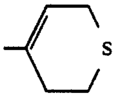 | $CH_3$ | H |

TABLE I-continued
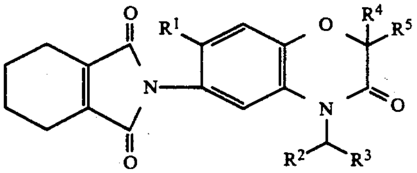
| $R^1$ | $R^2$ | $R^3$ | $R^4$ | $R^5$ |
|---|---|---|---|---|
| F | H | 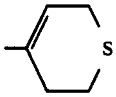 | $CH_3$ | H |
| H | $CH_3$ | 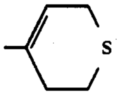 | $CH_3$ | H |
| F | $CH_3$ | 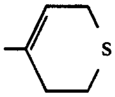 | $CH_3$ | H |
| H | H | 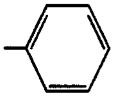 | H | H |
| F | H | 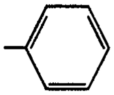 | H | H |
| H | $CH_3$ | 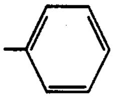 | H | H |
| F | $CH_3$ | 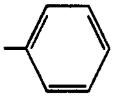 | H | H |
| H | H | 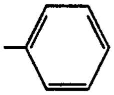 | $CH_3$ | H |
| F | H | 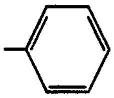 | $CH_3$ | H |
| H | $CH_3$ | 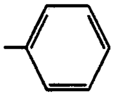 | $CH_3$ | H |
| F | $CH_3$ | 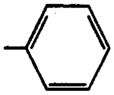 | $CH_3$ | H |
| H | H | 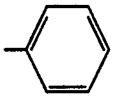 | $CH_3$ | $CH_3$ |
TABLE I-continued
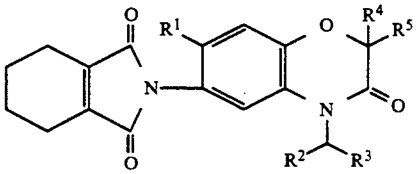
| $R^1$ | $R^2$ | $R^3$ | $R^4$ | $R^5$ |
|---|---|---|---|---|
| F | H | 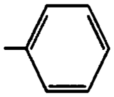 | $CH_3$ | $CH_3$ |
| H | $CH_3$ | 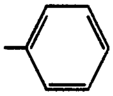 | $CH_3$ | $CH_3$ |
| F | $CH_3$ | 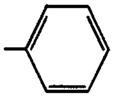 | $CH_3$ | $CH_3$ |
| H | H | 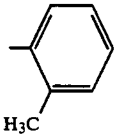 | H | H |
| F | H | 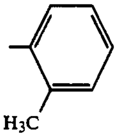 | H | H |
| H | $CH_3$ | 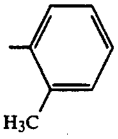 | H | H |
| F | $CH_3$ | 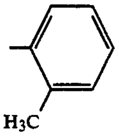 | H | H |
| H | H | 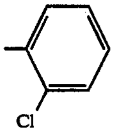 | H | H |
| F | H | 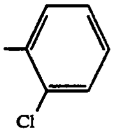 | H | H |
| H | $CH_3$ | 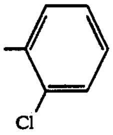 | H | H |

TABLE I-continued
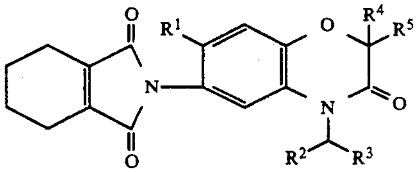
| R1 | R2 | R3 | R4 | R5 |
|---|---|---|---|---|
| F | $CH_3$ | 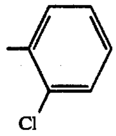 | H | H |
| H | H | 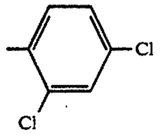 | H | H |
| F | H | 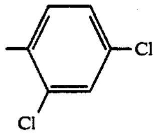 | H | H |
| H | $CH_3$ | 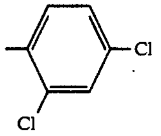 | H | H |
| F | $CH_3$ | 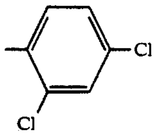 | H | H |
TABLE II
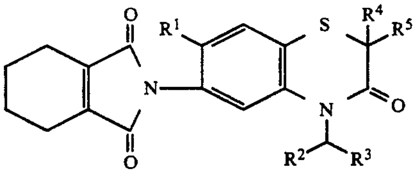
| R1 | R2 | R3 | R4 | R5 |
|---|---|---|---|---|
| H | H | 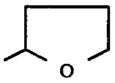 | H | H |
| F | H | 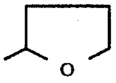 | H | H |
| H | $CH_3$ | 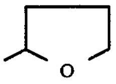 | H | H |
TABLE II-continued
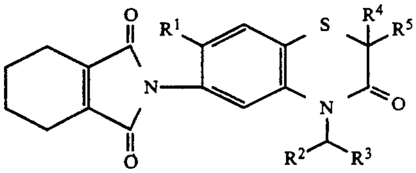
| R1 | R2 | R3 | R4 | R5 |
|---|---|---|---|---|
| F | $CH_3$ | 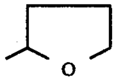 | H | H |
| H | H | 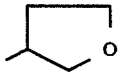 | H | H |
| F | H | 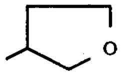 | H | H |
| H | $CH_3$ | 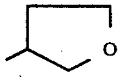 | H | H |
| F | $CH_3$ | 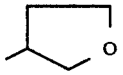 | H | H |
| H | H | 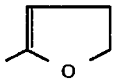 | H | H |
| F | H | 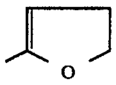 | H | H |
| H | $CH_3$ | 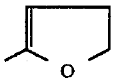 | H | H |
| F | $CH_3$ | 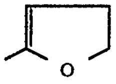 | H | H |
| H | H | 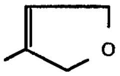 | H | H |
| F | H | 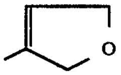 | H | H |
| H | $CH_3$ | 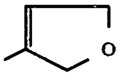 | H | H |
| F | $CH_3$ | 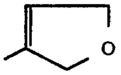 | H | H |
| H | H | 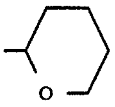 | H | H |

TABLE II-continued
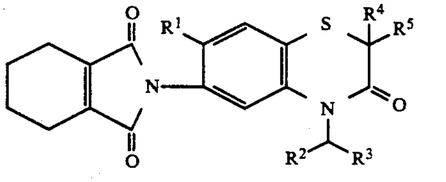
| R1 | R2 | R3 | R4 | R5 |
|---|---|---|---|---|
| F | H | 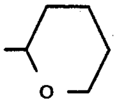 | H | H |
| H | $CH_3$ | 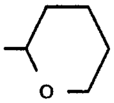 | H | H |
| F | $CH_3$ | 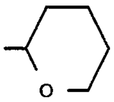 | H | H |
| H | H | 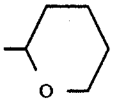 | $CH_3$ | H |
| F | H | 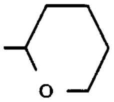 | $CH_3$ | H |
| H | $CH_3$ | 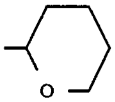 | $CH_3$ | H |
| F | $CH_3$ | 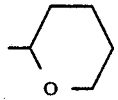 | $CH_3$ | H |
| H | H | 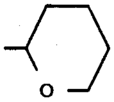 | $CH_3$ | $CH_3$ |
| F | H | 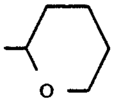 | $CH_3$ | $CH_3$ |
| H | $CH_3$ | 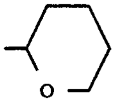 | $CH_3$ | $CH_3$ |
| F | $CH_3$ | 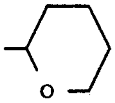 | $CH_3$ | $CH_3$ |
TABLE II-continued
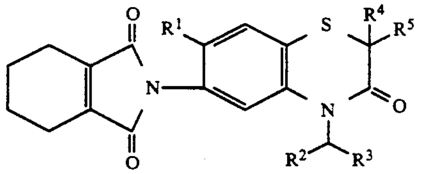
| R1 | R2 | R3 | R4 | R5 |
|---|---|---|---|---|
| H | H | 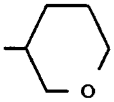 | H | H |
| F | H | 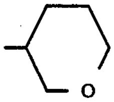 | H | H |
| H | $CH_3$ | 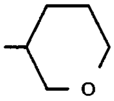 | H | H |
| F | $CH_3$ | 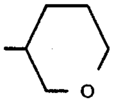 | H | H |
| H | H | 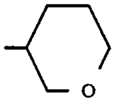 | $CH_3$ | H |
| F | H | 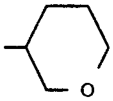 | $CH_3$ | H |
| H | $CH_3$ | 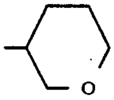 | $CH_3$ | H |
| F | $CH_3$ | 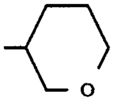 | $CH_3$ | H |
| H | H | 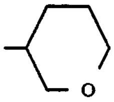 | $CH_3$ | $CH_3$ |
| F | H | 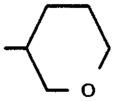 | $CH_3$ | $CH_3$ |
| H | $CH_3$ | 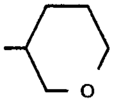 | $CH_3$ | $CH_3$ |

TABLE II-continued
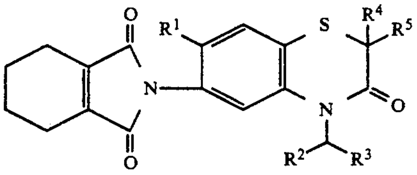
| $R^1$ | $R^2$ | $R^3$ | $R^4$ | $R^5$ |
|---|---|---|---|---|
| F | $CH_3$ | 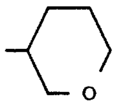 | $CH_3$ | $CH_3$ |
| H | H | 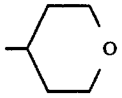 | H | H |
| F | H | 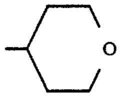 | H | H |
| H | $CH_3$ | 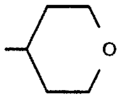 | H | H |
| F | $CH_3$ | 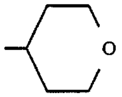 | H | H |
| H | H | 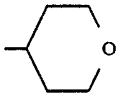 | $CH_3$ | H |
| F | H | 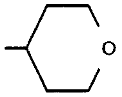 | $CH_3$ | H |
| H | $CH_3$ | 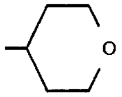 | $CH_3$ | H |
| F | $CH_3$ | 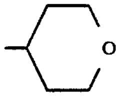 | $CH_3$ | H |
| H | H | 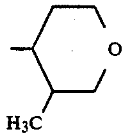 | H | H |
| F | H | 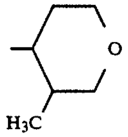 | H | H |
TABLE II-continued
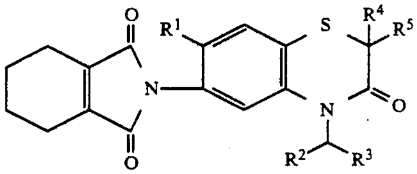
| $R^1$ | $R^2$ | $R^3$ | $R^4$ | $R^5$ |
|---|---|---|---|---|
| H | $CH_3$ | 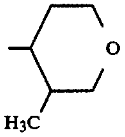 | H | H |
| F | $CH_3$ | 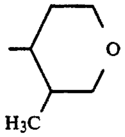 | H | H |
| H | H | 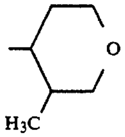 | $CH_3$ | H |
| F | H | 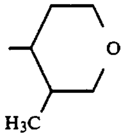 | $CH_3$ | H |
| H | $CH_3$ | 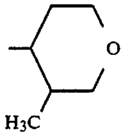 | $CH_3$ | H |
| F | $CH_3$ | 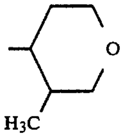 | $CH_3$ | H |
| H | H | 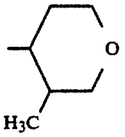 | $CH_3$ | $CH_3$ |
| F | H | 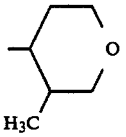 | $CH_3$ | $CH_3$ |
| H | $CH_3$ | 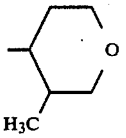 | $CH_3$ | $CH_3$ |

TABLE II-continued
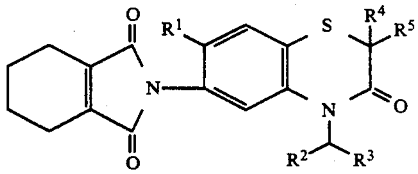
| $R^1$ | $R^2$ | $R^3$ | $R^4$ | $R^5$ |
|---|---|---|---|---|
| F | $CH_3$ | 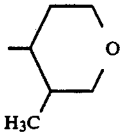 | $CH_3$ | $CH_3$ |
| H | H | 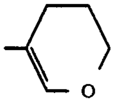 | H | H |
| F | H | 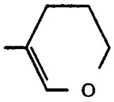 | H | H |
| H | $CH_3$ | 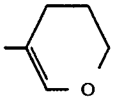 | H | H |
| F | $CH_3$ | 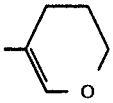 | H | H |
| H | H | 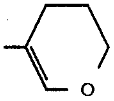 | $CH_3$ | H |
| F | H | 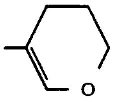 | $CH_3$ | H |
| H | $CH_3$ | 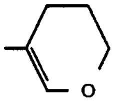 | $CH_3$ | H |
| F | $CH_3$ | 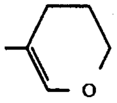 | $CH_3$ | H |
| H | H | 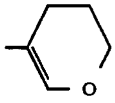 | $CH_3$ | $CH_3$ |
| F | H | 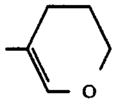 | $CH_3$ | $CH_3$ |
TABLE II-continued
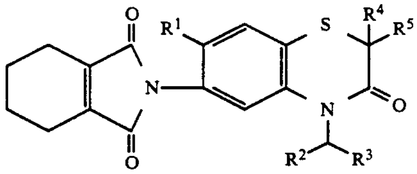
| $R^1$ | $R^2$ | $R^3$ | $R^4$ | $R^5$ |
|---|---|---|---|---|
| H | $CH_3$ | 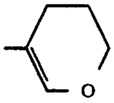 | $CH_3$ | $CH_3$ |
| F | $CH_3$ | 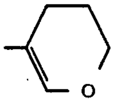 | $CH_3$ | $CH_3$ |
| H | H | 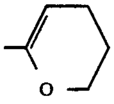 | $CH_3$ | $CH_3$ |
| F | H | 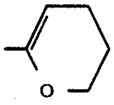 | $CH_3$ | $CH_3$ |
| H | $CH_3$ | 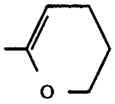 | $CH_3$ | $CH_3$ |
| F | $CH_3$ | 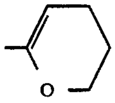 | $CH_3$ | $CH_3$ |
| H | H | 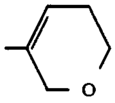 | H | H |
| F | H | 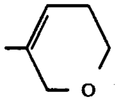 | H | H |
| H | $CH_3$ | 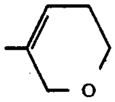 | H | H |
| F | $CH_3$ | 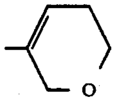 | H | H |
| H | H | 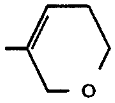 | $CH_3$ | H |

TABLE II-continued
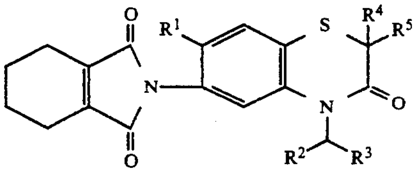
| $R^1$ | $R^2$ | $R^3$ | $R^4$ | $R^5$ |
|---|---|---|---|---|
| F | H | 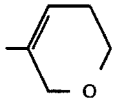 | $CH_3$ | H |
| H | $CH_3$ | 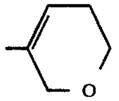 | $CH_3$ | H |
| F | $CH_3$ | 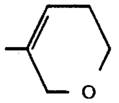 | $CH_3$ | H |
| H | H | 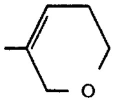 | $CH_3$ | $CH_3$ |
| F | H | 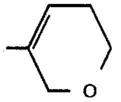 | $CH_3$ | $CH_3$ |
| H | $CH_3$ | 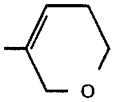 | $CH_3$ | $CH_3$ |
| F | $CH_3$ | 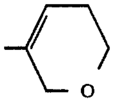 | $CH_3$ | $CH_3$ |
| H | H | 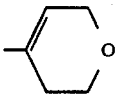 | H | H |
| F | H | 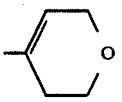 | H | H |
| H | $CH_3$ | 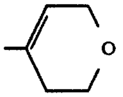 | H | H |
| F | $CH_3$ | 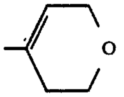 | H | H |
TABLE II-continued
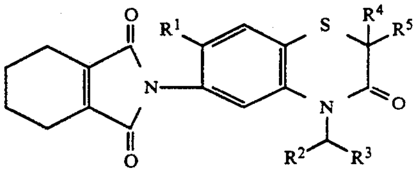
| $R^1$ | $R^2$ | $R^3$ | $R^4$ | $R^5$ |
|---|---|---|---|---|
| H | H | 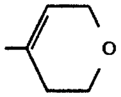 | $CH_3$ | H |
| F | H | 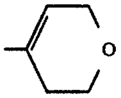 | $CH_3$ | H |
| H | $CH_3$ | 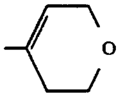 | $CH_3$ | H |
| F | $CH_3$ | 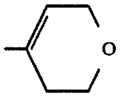 | $CH_3$ | H |
| H | H | 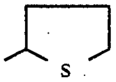 | H | H |
| F | H | 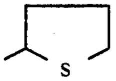 | H | H |
| H | $CH_3$ | 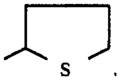 | H | H |
| F | $CH_3$ | 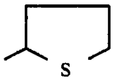 | H | H |
| H | H | 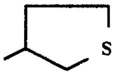 | H | H |
| F | H | 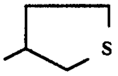 | H | H |
| H | $CH_3$ | 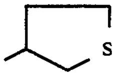 | H | H |
| F | $CH_3$ | 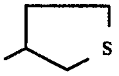 | H | H |
| H | H | 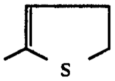 | H | H |

TABLE II-continued
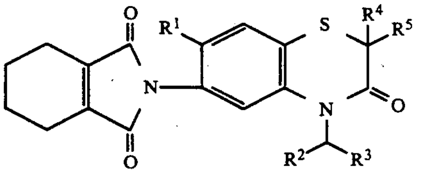
| R¹ | R² | R³ | R⁴ | R⁵ |
|---|---|---|---|---|
| F | H | 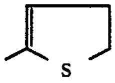 | H | H |
| H | $CH_3$ | 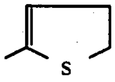 | H | H |
| F | $CH_3$ | 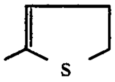 | H | H |
| H | H | 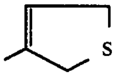 | H | H |
| F | H | 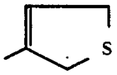 | H | H |
| H | $CH_3$ | 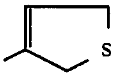 | H | H |
| F | $CH_3$ | 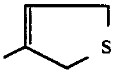 | H | H |
| H | H | 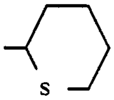 | H | H |
| F | H | 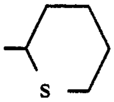 | H | H |
| H | $CH_3$ | 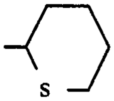 | H | H |
| F | $CH_3$ | 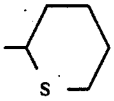 | H | H |
| H | H | 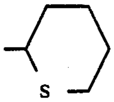 | $CH_3$ | H |
TABLE II-continued
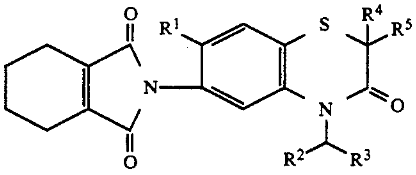
| R¹ | R² | R³ | R⁴ | R⁵ |
|---|---|---|---|---|
| F | H | 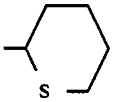 | $CH_3$ | H |
| H | $CH_3$ | 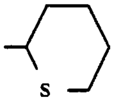 | $CH_3$ | H |
| F | $CH_3$ | 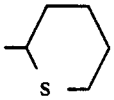 | $CH_3$ | H |
| H | H | 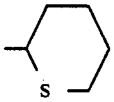 | $CH_3$ | $CH_3$ |
| F | H | 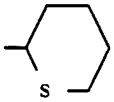 | $CH_3$ | $CH_3$ |
| H | $CH_3$ | 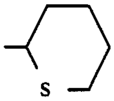 | $CH_3$ | $CH_3$ |
| F | $CH_3$ | 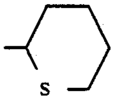 | $CH_3$ | $CH_3$ |
| H | H | 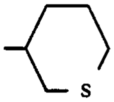 | H | H |
| F | H | 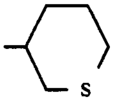 | H | H |
| H | $CH_3$ | 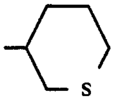 | H | H |
| F | $CH_3$ | 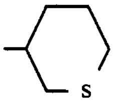 | H | H |

TABLE II-continued
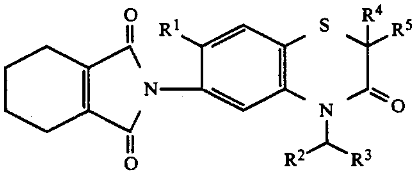
| $R^1$ | $R^2$ | $R^3$ | $R^4$ | $R^5$ |
|---|---|---|---|---|
| H | H | 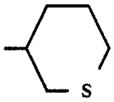 | $CH_3$ | H |
| F | H | 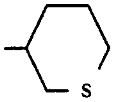 | $CH_3$ | H |
| H | $CH_3$ | 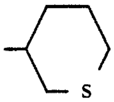 | $CH_3$ | H |
| F | $CH_3$ | 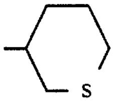 | $CH_3$ | H |
| H | H | 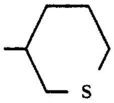 | $CH_3$ | $CH_3$ |
| F | H | 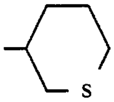 | $CH_3$ | $CH_3$ |
| H | $CH_3$ | 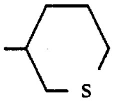 | $CH_3$ | $CH_3$ |
| F | $CH_3$ | 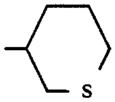 | $CH_3$ | $CH_3$ |
| H | H | 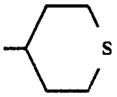 | H | H |
| F | H | 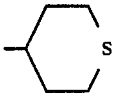 | H | H |
| H | $CH_3$ | 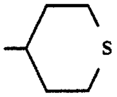 | H | H |
TABLE II-continued
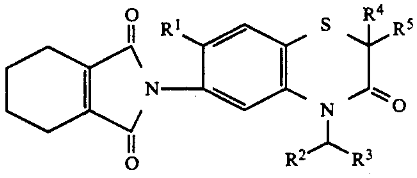
| $R^1$ | $R^2$ | $R^3$ | $R^4$ | $R^5$ |
|---|---|---|---|---|
| F | $CH_3$ | 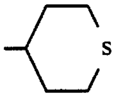 | H | H |
| H | H | 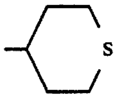 | $CH_3$ | H |
| F | H | 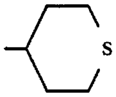 | $CH_3$ | H |
| H | $CH_3$ | 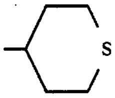 | $CH_3$ | H |
| F | $CH_3$ | 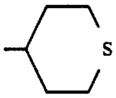 | $CH_3$ | H |
| H | H | 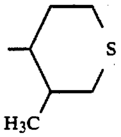 | H | H |
| F | H | 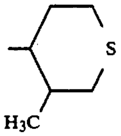 | H | H |
| H | $CH_3$ | 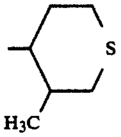 | H | H |
| F | $CH_3$ | 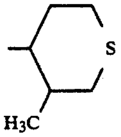 | H | H |
| H | H | 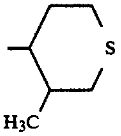 | $CH_3$ | H |

TABLE II-continued
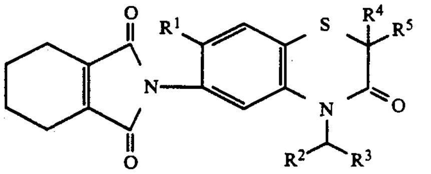
| $R^1$ | $R^2$ | $R^3$ | $R^4$ | $R^5$ |
|---|---|---|---|---|
| F | H | 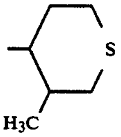 | $CH_3$ | H |
| H | $CH_3$ | 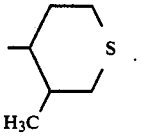 | $CH_3$ | H |
| F | $CH_3$ | 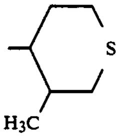 | $CH_3$ | H |
| H | H | 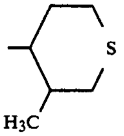 | $CH_3$ | $CH_3$ |
| F | H | 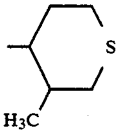 | $CH_3$ | $CH_3$ |
| H | $CH_3$ | 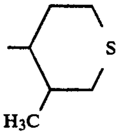 | $CH_3$ | $CH_3$ |
| F | $CH_3$ | 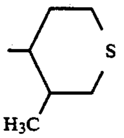 | $CH_3$ | $CH_3$ |
| H | H | 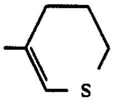 | H | H |
| F | H | 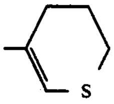 | H | H |
TABLE II-continued
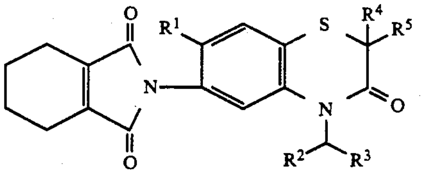
| $R^1$ | $R^2$ | $R^3$ | $R^4$ | $R^5$ |
|---|---|---|---|---|
| H | $CH_3$ | 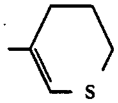 | H | H |
| F | $CH_3$ | 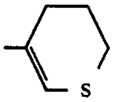 | H | H |
| H | H | 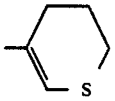 | $CH_3$ | H |
| F | H | 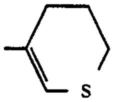 | $CH_3$ | H |
| H | $CH_3$ | 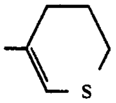 | $CH_3$ | H |
| F | $CH_3$ | 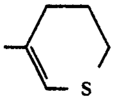 | $CH_3$ | H |
| H | H | 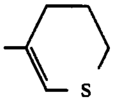 | $CH_3$ | $CH_3$ |
| F | H | 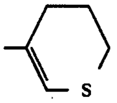 | $CH_3$ | $CH_3$ |
| H | $CH_3$ | 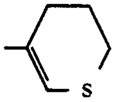 | $CH_3$ | $CH_3$ |
| F | $CH_3$ | 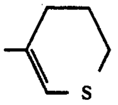 | $CH_3$ | $CH_3$ |
| H | H | 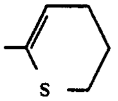 | $CH_3$ | $CH_3$ |

TABLE II-continued
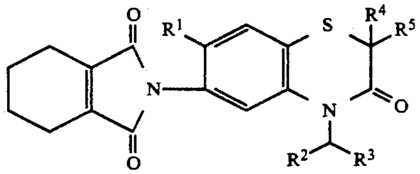
| $R^1$ | $R^2$ | $R^3$ | $R^4$ | $R^5$ |
|---|---|---|---|---|
| F | H | 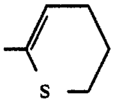 | $CH_3$ | $CH_3$ |
| H | $CH_3$ | 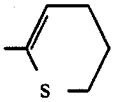 | $CH_3$ | $CH_3$ |
| F | $CH_3$ | 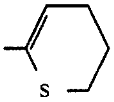 | $CH_3$ | $CH_3$ |
| H | H | 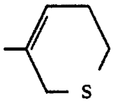 | H | H |
| F | H | 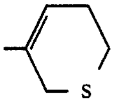 | H | H |
| H | $CH_3$ | 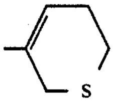 | H | H |
| F | $CH_3$ | 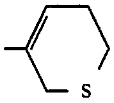 | H | H |
| H | H | 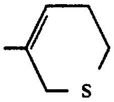 | $CH_3$ | H |
| F | H | 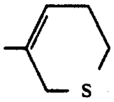 | $CH_3$ | H |
| H | $CH_3$ | 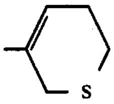 | $CH_3$ | H |
| F | $CH_3$ | 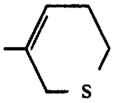 | $CH_3$ | H |
TABLE II-continued
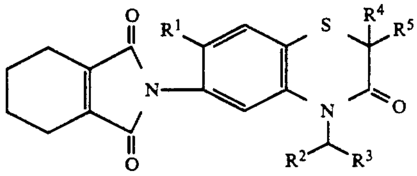
| $R^1$ | $R^2$ | $R^3$ | $R^4$ | $R^5$ |
|---|---|---|---|---|
| H | H | 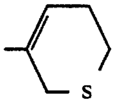 | $CH_3$ | $CH_3$ |
| F | H | 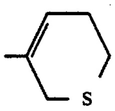 | $CH_3$ | $CH_3$ |
| H | $CH_3$ | 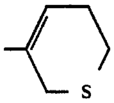 | $CH_3$ | $CH_3$ |
| F | $CH_3$ | 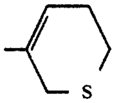 | $CH_3$ | $CH_3$ |
| H | H | 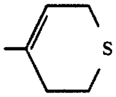 | H | H |
| F | H | 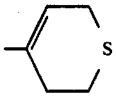 | H | H |
| H | $CH_3$ | 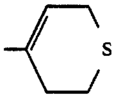 | H | H |
| F | $CH_3$ | 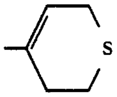 | H | H |
| H | H | 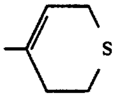 | $CH_3$ | H |
| F | H | 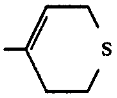 | $CH_3$ | H |
| H | $CH_3$ | 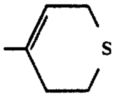 | $CH_3$ | H |
| F | $CH_3$ | 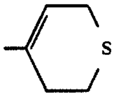 | $CH_3$ | H |

TABLE II-continued
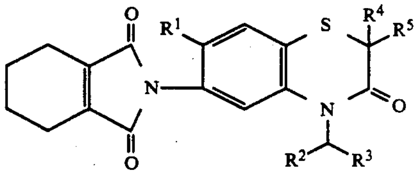
| $R^1$ | $R^2$ | $R^3$ | $R^4$ | $R^5$ |
|---|---|---|---|---|
| H | H | 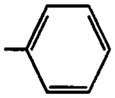 | H | H |
| F | H | 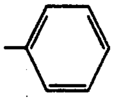 | H | H |
| H | $CH_3$ | 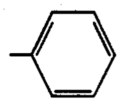 | H | H |
| F | $CH_3$ | 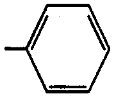 | H | H |
| H | H | 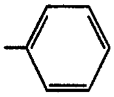 | $CH_3$ | H |
| F | H | 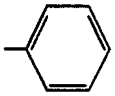 | $CH_3$ | H |
| H | $CH_3$ | 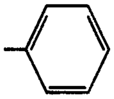 | $CH_3$ | H |
| F | $CH_3$ | 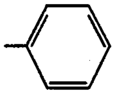 | $CH_3$ | H |
| H | H | 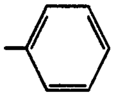 | $CH_3$ | $CH_3$ |
| F | H | 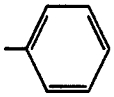 | $CH_3$ | $CH_3$ |
| H | $CH_3$ | 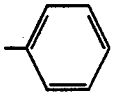 | $CH_3$ | $CH_3$ |
| F | $CH_3$ | 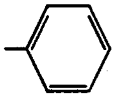 | $CH_3$ | $CH_3$ |
TABLE II-continued
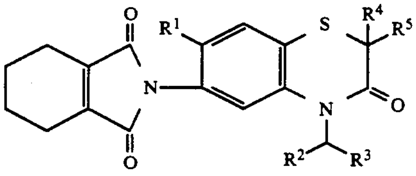
| $R^1$ | $R^2$ | $R^3$ | $R^4$ | $R^5$ |
|---|---|---|---|---|
| H | H | 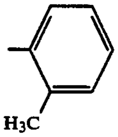 | H | H |
| F | H | 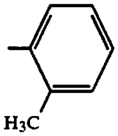 | H | H |
| H | $CH_3$ | 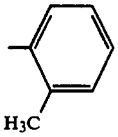 | H | H |
| F | $CH_3$ | 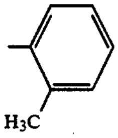 | H | H |
| H | H | 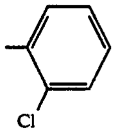 | H | H |
| F | H | 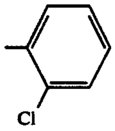 | H | H |
| H | $CH_3$ | 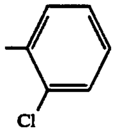 | H | H |
| F | $CH_3$ | 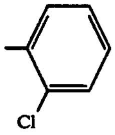 | H | H |
| H | H | 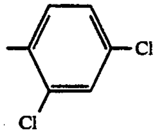 | H | H |

TABLE II-continued

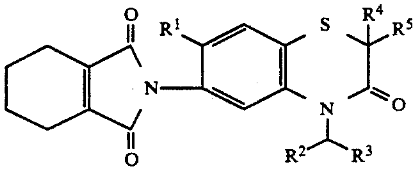

| $R^1$ | $R^2$ | $R^3$ | $R^4$ | $R^5$ |
|---|---|---|---|---|
| F | H | 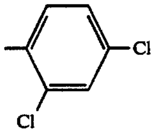 | H | H |
| H | $CH_3$ | 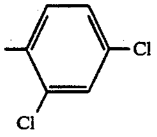 | H | H |
| F | $CH_3$ | 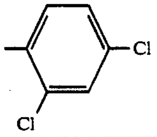 | H | H |

TABLE IIa

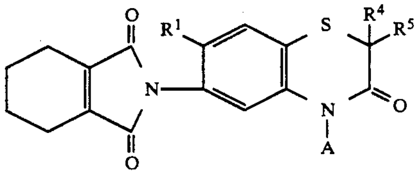

| $R^1$ | $R^4$ | $R^5$ | A |
|---|---|---|---|
| H | H | H | H |
| F | H | H | H |
| H | $CH_3$ | H | H |
| F | $CH_3$ | H | H |
| H | H | H | $CH_3$ |
| F | H | H | $CH_3$ |
| H | $CH_3$ | H | $CH_3$ |
| F | $CH_3$ | H | $CH_3$ |
| H | H | H | $CH_2CH_3$ |
| F | H | H | $CH_2CH_3$ |
| H | $CH_3$ | H | $CH_2CH_3$ |
| F | $CH_3$ | H | $CH_2CH_3$ |
| H | H | H | $CH(CH_3)_2$ |
| F | H | H | $CH(CH_3)_2$ |
| H | $CH_3$ | H | $CH(CH_3)_2$ |
| F | $CH_3$ | H | $CH(CH_3)_2$ |
| H | H | H | $CH_2CH{=}CH_2$ |
| F | H | H | $CH_2CH{=}CH_2$ |
| H | $CH_3$ | H | $CH_2CH{=}CH_2$ |
| F | $CH_3$ | H | $CH_2CH{=}CH_2$ |
| H | H | H | $CH_2CH{=}CHCH_3$ |
| F | H | H | $CH_2CH{=}CHCH_3$ |
| H | $CH_3$ | H | $CH_2CH{=}CHCH_3$ |
| F | $CH_3$ | H | $CH_2CH{=}CHCH_3$ |
| H | H | H | $CH_2C{\equiv}CH$ |
| F | H | H | $CH_2C{\equiv}CH$ |
| H | $CH_3$ | H | $CH_2C{\equiv}CH$ |
| F | $CH_3$ | H | $CH_2C{\equiv}CH$ |
| H | H | H | $CH_2C{\equiv}CCH_3$ |
| F | H | H | $CH_2C{\equiv}CCH_3$ |
| H | $CH_3$ | H | $CH_2C{\equiv}CCH_3$ |
| F | $CH_3$ | H | $CH_2C{\equiv}CCH_3$ |
| H | H | H | $CH_2OCH_3$ |
| F | H | H | $CH_2OCH_3$ |
| H | $CH_3$ | H | $CH_2OCH_3$ |

TABLE IIa-continued

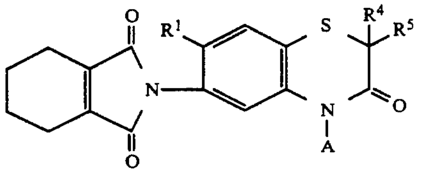

| $R^1$ | $R^4$ | $R^5$ | A |
|---|---|---|---|
| F | $CH_3$ | H | $CH_2OCH_3$ |
| H | H | H | $(CH_2)_2OCH_3$ |
| F | H | H | $(CH_2)_2OCH_3$ |
| H | $CH_3$ | H | $(CH_2)_2OCH_3$ |
| F | $CH_3$ | H | $(CH_2)_2OCH_3$ |
| H | H | H | $CH_2CO_2CH_3$ |
| F | H | H | $CH_2CO_2CH_3$ |
| H | $CH_3$ | H | $CH_2CO_2CH_3$ |
| F | $CH_3$ | H | $CH_2CO_2CH_3$ |
| H | H | H | $CH_2CO_2CH_2CH_3$ |
| F | H | H | $CH_2CO_2CH_2CH_3$ |
| H | $CH_3$ | H | $CH_2CO_2CH_2CH_3$ |
| F | $CH_3$ | H | $CH_2CO_2CH_2CH_3$ |
| H | H | H | $CH(CH_3)CO_2CH_3$ |
| F | H | H | $CH(CH_3)CO_2CH_3$ |
| H | $CH_3$ | H | $CH(CH_3)CO_2CH_3$ |
| F | $CH_3$ | H | $CH(CH_3)CO_2CH_3$ |
| H | H | H | $CH(CH_3)CO_2CH_2CH_3$ |
| F | H | H | $CH(CH_3)CO_2CH_2CH_3$ |
| H | $CH_3$ | H | $CH(CH_3)CO_2CH_2CH_3$ |
| F | $CH_3$ | H | $CH(CH_3)CO_2CH_2CH_3$ |
| H | $CH_3$ | $CH_3$ | H |
| F | $CH_3$ | $CH_3$ | H |
| H | $CH_3$ | $CH_3$ | $CH_3$ |
| F | $CH_3$ | $CH_3$ | $CH_3$ |
| H | $CH_3$ | $CH_3$ | $CH_2CH_3$ |
| F | $CH_3$ | $CH_3$ | $CH_2CH_3$ |
| H | $CH_3$ | $CH_3$ | $CH_2CH{=}CH_2$ |
| F | $CH_3$ | $CH_3$ | $CH_2CH{=}CH_2$ |
| H | $CH_3$ | $CH_3$ | $CH_2C{\equiv}CH$ |
| F | $CH_3$ | $CH_3$ | $CH_2C{\equiv}CH$ |
| H | $CH_3$ | $CH_3$ | $(CH_2)_2OCH_3$ |
| F | $CH_3$ | $CH_3$ | $(CH_2)_2OCH_3$ |
| H | $CH_3$ | $CH_3$ | $CH_2CO_2CH_3$ |
| F | $CH_3$ | $CH_3$ | $CH_2CO_2CH_3$ |
| H | $CH_3$ | $CH_3$ | $CH(CH_3)CO_2CH_3$ |
| F | $CH_3$ | $CH_3$ | $CH(CH_3)CO_2CH_3$ |

TABLE III

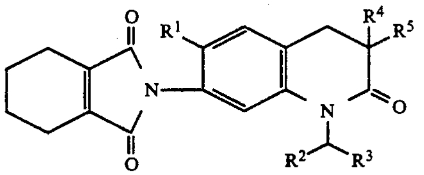

| $R^1$ | $R^2$ | $R^3$ | $R^4$ | $R^5$ |
|---|---|---|---|---|
| H | H | 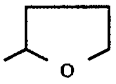 | H | H |
| F | H | 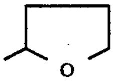 | H | H |
| H | $CH_3$ | 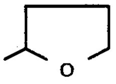 | H | H |
| F | $CH_3$ | 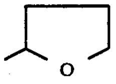 | H | H |

TABLE III-continued
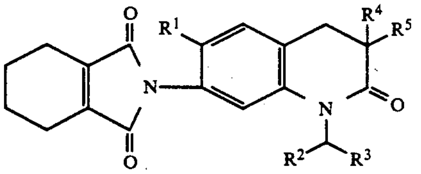
| $R^1$ | $R^2$ | $R^3$ | $R^4$ | $R^5$ |
|---|---|---|---|---|
| H | H | 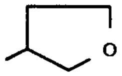 | H | H |
| F | H | 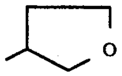 | H | H |
| H | $CH_3$ | 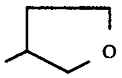 | H | H |
| F | $CH_3$ | 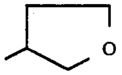 | H | H |
| H | H | 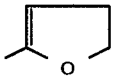 | H | H |
| F | H | 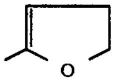 | H | H |
| H | $CH_3$ | 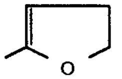 | H | H |
| F | $CH_3$ | 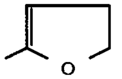 | H | H |
| H | H | 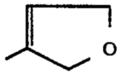 | H | H |
| F | H | 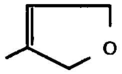 | H | H |
| H | $CH_3$ | 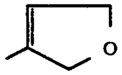 | H | H |
| F | $CH_3$ | 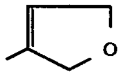 | H | H |
| H | H | 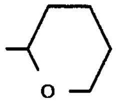 | H | H |
TABLE III-continued
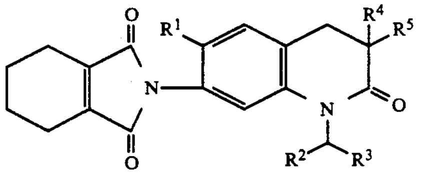
| $R^1$ | $R^2$ | $R^3$ | $R^4$ | $R^5$ |
|---|---|---|---|---|
| F | H | 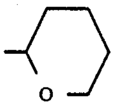 | H | H |
| H | $CH_3$ | 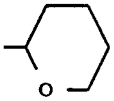 | H | H |
| F | $CH_3$ | 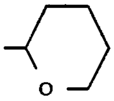 | H | H |
| H | H | 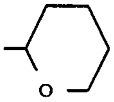 | $CH_3$ | H |
| F | H | 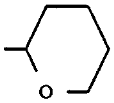 | $CH_3$ | H |
| H | $CH_3$ | 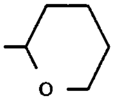 | $CH_3$ | H |
| F | $CH_3$ | 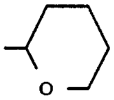 | $CH_3$ | H |
| H | H | 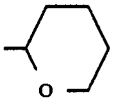 | $CH_3$ | $CH_3$ |
| F | H | 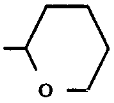 | $CH_3$ | $CH_3$ |
| H | $CH_3$ | 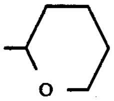 | $CH_3$ | $CH_3$ |
| F | $CH_3$ | 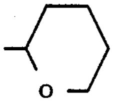 | $CH_3$ | $CH_3$ |

TABLE III-continued
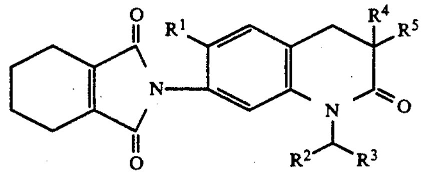
| R¹ | R² | R³ | R⁴ | R⁵ |
|---|---|---|---|---|
| H | H | 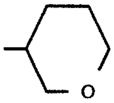 | H | H |
| F | H | 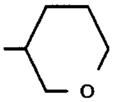 | H | H |
| H | $CH_3$ | 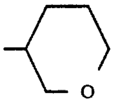 | H | H |
| F | $CH_3$ | 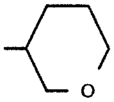 | H | H |
| H | H | 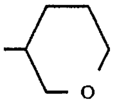 | $CH_3$ | H |
| F | H | 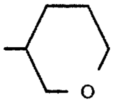 | $CH_3$ | H |
| H | $CH_3$ | 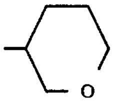 | $CH_3$ | H |
| F | $CH_3$ | 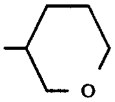 | $CH_3$ | H |
| H | H | 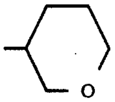 | $CH_3$ | $CH_3$ |
| F | H | 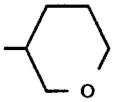 | $CH_3$ | $CH_3$ |
| H | $CH_3$ | 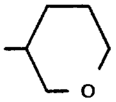 | $CH_3$ | $CH_3$ |
TABLE III-continued
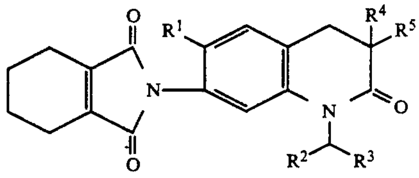
| R¹ | R² | R³ | R⁴ | R⁵ |
|---|---|---|---|---|
| F | $CH_3$ | 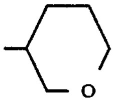 | $CH_3$ | $CH_3$ |
| H | H | 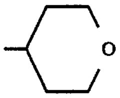 | H | H |
| F | H | 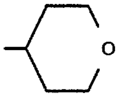 | H | H |
| H | $CH_3$ | 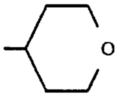 | H | H |
| F | $CH_3$ | 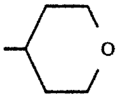 | H | H |
| H | H | 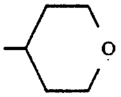 | $CH_3$ | H |
| F | H | 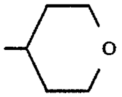 | $CH_3$ | H |
| H | $CH_3$ | 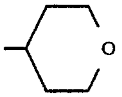 | $CH_3$ | H |
| F | $CH_3$ | 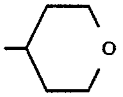 | $CH_3$ | H |
| H | H | 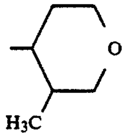 | H | H |
| F | H | 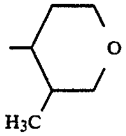 | H | H |

TABLE III-continued
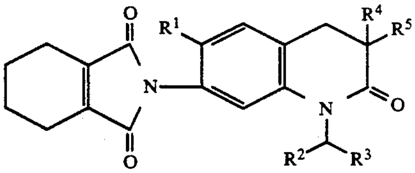
| $R^1$ | $R^2$ | $R^3$ | $R^4$ | $R^5$ |
|---|---|---|---|---|
| H | $CH_3$ | 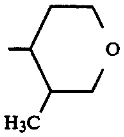 | H | H |
| F | $CH_3$ | 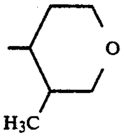 | H | H |
| H | H | 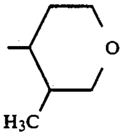 | $CH_3$ | H |
| F | H | 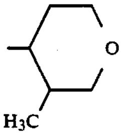 | $CH_3$ | H |
| H | $CH_3$ | 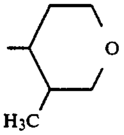 | $CH_3$ | H |
| F | $CH_3$ | 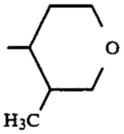 | $CH_3$ | H |
| H | H | 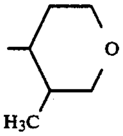 | $CH_3$ | $CH_3$ |
| F | H | 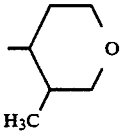 | $CH_3$ | $CH_3$ |
| H | $CH_3$ | 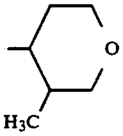 | $CH_3$ | $CH_3$ |
TABLE III-continued
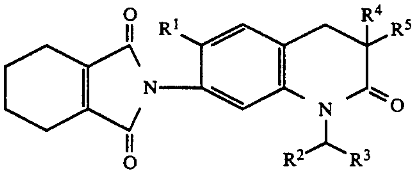
| $R^1$ | $R^2$ | $R^3$ | $R^4$ | $R^5$ |
|---|---|---|---|---|
| F | $CH_3$ | 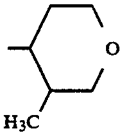 | $CH_3$ | $CH_3$ |
| H | H | 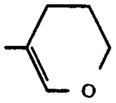 | H | H |
| F | H | 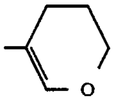 | H | H |
| H | $CH_3$ | 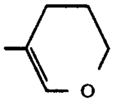 | H | H |
| F | $CH_3$ | 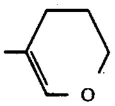 | H | H |
| H | H | 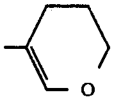 | $CH_3$ | H |
| F | H | 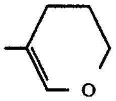 | $CH_3$ | H |
| H | $CH_3$ | 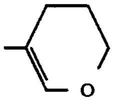 | $CH_3$ | H |
| F | $CH_3$ | 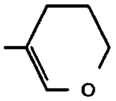 | $CH_3$ | H |
| H | H | 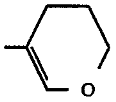 | $CH_3$ | $CH_3$ |
| F | H | 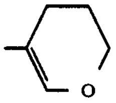 | $CH_3$ | $CH_3$ |

TABLE III-continued
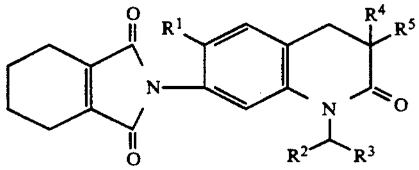
| $R^1$ | $R^2$ | $R^3$ | $R^4$ | $R^5$ |
|---|---|---|---|---|
| H | $CH_3$ | 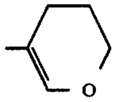 | $CH_3$ | $CH_3$ |
| F | $CH_3$ | 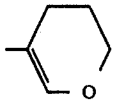 | $CH_3$ | $CH_3$ |
| H | H | 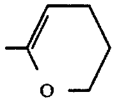 | $CH_3$ | $CH_3$ |
| F | H | 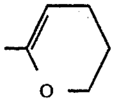 | $CH_3$ | $CH_3$ |
| H | $CH_3$ | 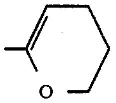 | $CH_3$ | $CH_3$ |
| F | $CH_3$ | 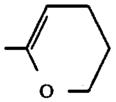 | $CH_3$ | $CH_3$ |
| H | H | 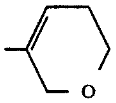 | H | H |
| F | H | 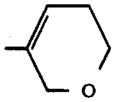 | H | H |
| H | $CH_3$ | 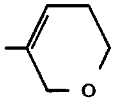 | H | H |
| F | $CH_3$ | 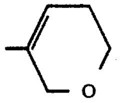 | H | H |
| H | H | 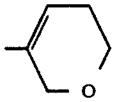 | $CH_3$ | H |
TABLE III-continued
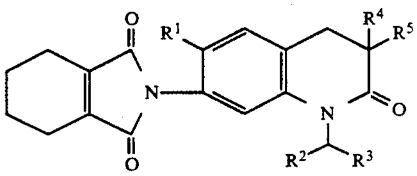
| $R^1$ | $R^2$ | $R^3$ | $R^4$ | $R^5$ |
|---|---|---|---|---|
| F | H | 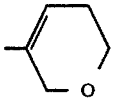 | $CH_3$ | H |
| H | $CH_3$ | 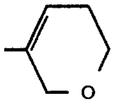 | $CH_3$ | H |
| F | $CH_3$ | 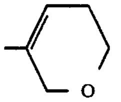 | $CH_3$ | H |
| H | H | 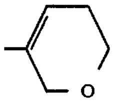 | $CH_3$ | $CH_3$ |
| F | H | 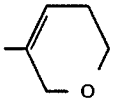 | $CH_3$ | $CH_3$ |
| H | $CH_3$ | 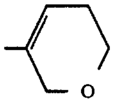 | $CH_3$ | $CH_3$ |
| F | $CH_3$ | 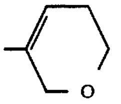 | $CH_3$ | $CH_3$ |
| H | H | 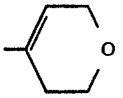 | H | H |
| F | H | 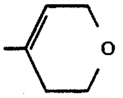 | H | H |
| H | $CH_3$ | 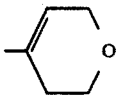 | H | H |
| F | $CH_3$ | 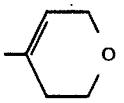 | H | H |

TABLE III-continued
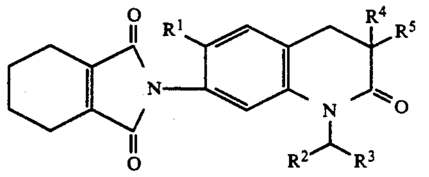
| $R^1$ | $R^2$ | $R^3$ | $R^4$ | $R^5$ |
|---|---|---|---|---|
| H | H | 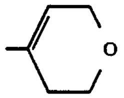 | $CH_3$ | H |
| F | H | 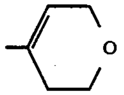 | $CH_3$ | H |
| H | $CH_3$ | 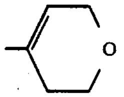 | $CH_3$ | H |
| F | $CH_3$ | 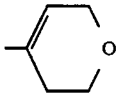 | $CH_3$ | H |
| H | H | 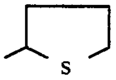 | H | H |
| F | H | 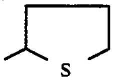 | H | H |
| H | $CH_3$ | 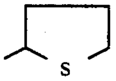 | H | H |
| F | $CH_3$ | 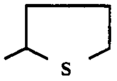 | H | H |
| H | H | 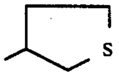 | H | H |
| F | H | 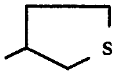 | H | H |
| H | $CH_3$ | 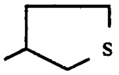 | H | H |
| F | $CH_3$ | 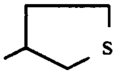 | H | H |
| H | H | 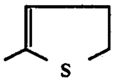 | H | H |
TABLE III-continued
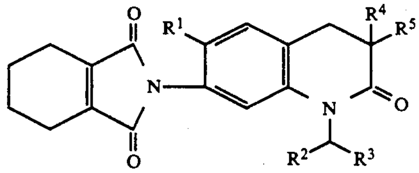
| $R^1$ | $R^2$ | $R^3$ | $R^4$ | $R^5$ |
|---|---|---|---|---|
| F | H | 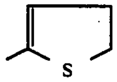 | H | H |
| H | $CH_3$ | 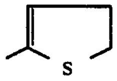 | H | H |
| F | $CH_3$ | 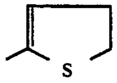 | H | H |
| H | H | 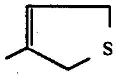 | H | H |
| F | H | 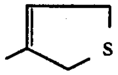 | H | H |
| H | $CH_3$ | 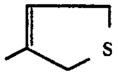 | H | H |
| F | $CH_3$ | 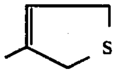 | H | H |
| H | H | 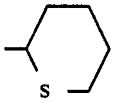 | H | H |
| F | H | 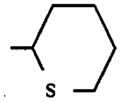 | H | H |
| H | $CH_3$ | 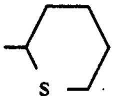 | H | H |
| F | $CH_3$ | 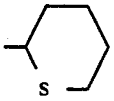 | H | H |
| H | H | 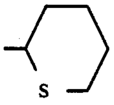 | $CH_3$ | H |

TABLE III-continued
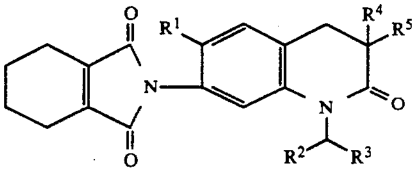
| R¹ | R² | R³ | R⁴ | R⁵ |
|---|---|---|---|---|
| F | H | 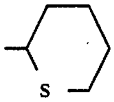 | $CH_3$ | H |
| H | $CH_3$ | 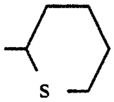 | $CH_3$ | H |
| F | $CH_3$ | 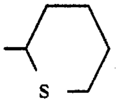 | $CH_3$ | H |
| H | H | 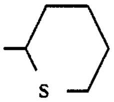 | $CH_3$ | $CH_3$ |
| F | H | 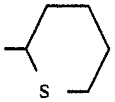 | $CH_3$ | $CH_3$ |
| H | $CH_3$ | 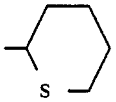 | $CH_3$ | $CH_3$ |
| F | $CH_3$ | 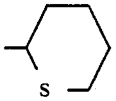 | $CH_3$ | $CH_3$ |
| H | H | 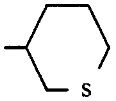 | H | H |
| F | H | 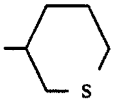 | H | H |
| H | $CH_3$ | 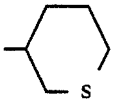 | H | H |
| F | $CH_3$ | 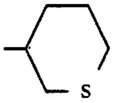 | H | H |
TABLE III-continued
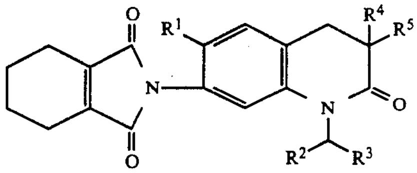
| R¹ | R² | R³ | R⁴ | R⁵ |
|---|---|---|---|---|
| H | H | 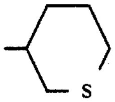 | $CH_3$ | H |
| F | H | 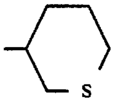 | $CH_3$ | H |
| H | $CH_3$ | 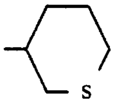 | $CH_3$ | H |
| F | $CH_3$ | 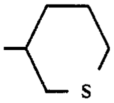 | $CH_3$ | H |
| H | H | 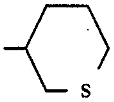 | $CH_3$ | $CH_3$ |
| F | H | 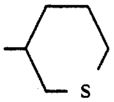 | $CH_3$ | $CH_3$ |
| H | $CH_3$ | 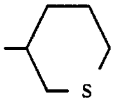 | $CH_3$ | $CH_3$ |
| F | $CH_3$ | 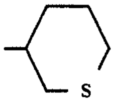 | $CH_3$ | $CH_3$ |
| H | H | 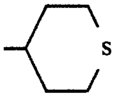 | H | H |
| F | H | 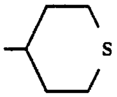 | H | H |
| H | $CH_3$ | 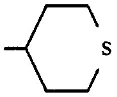 | H | H |

TABLE III-continued
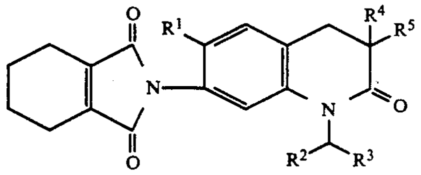
| $R^1$ | $R^2$ | $R^3$ | $R^4$ | $R^5$ |
|---|---|---|---|---|
| F | $CH_3$ | 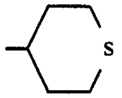 | H | H |
| H | H | 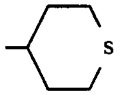 | $CH_3$ | H |
| F | H | 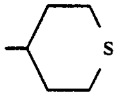 | $CH_3$ | H |
| H | $CH_3$ | 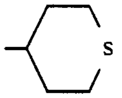 | $CH_3$ | H |
| F | $CH_3$ | 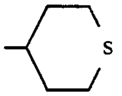 | $CH_3$ | H |
| H | H | 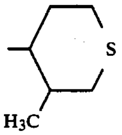 | H | H |
| F | H | 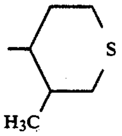 | H | H |
| F | $CH_3$ | 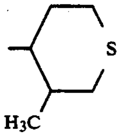 | H | H |
| F | $CH_3$ | 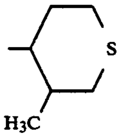 | H | H |
| H | H | 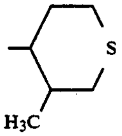 | $CH_3$ | H |
TABLE III-continued
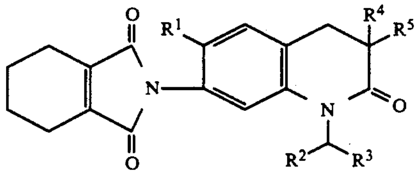
| $R^1$ | $R^2$ | $R^3$ | $R^4$ | $R^5$ |
|---|---|---|---|---|
| F | H | 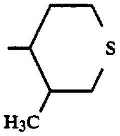 | $CH_3$ | H |
| H | $CH_3$ | 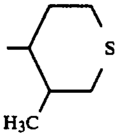 | $CH_3$ | H |
| F | $CH_3$ | 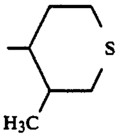 | $CH_3$ | H |
| H | H | 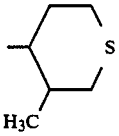 | $CH_3$ | $CH_3$ |
| F | H | 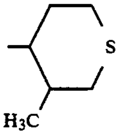 | $CH_3$ | $CH_3$ |
| H | $CH_3$ | 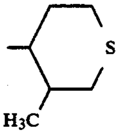 | $CH_3$ | $CH_3$ |
| F | $CH_3$ | 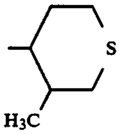 | $CH_3$ | $CH_3$ |
| H | H | 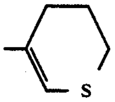 | H | H |
| F | H | 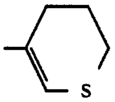 | H | H |

TABLE III-continued
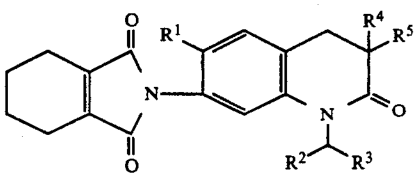
| $R^1$ | $R^2$ | $R^3$ | $R^4$ | $R^5$ |
|---|---|---|---|---|
| H | $CH_3$ | 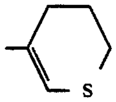 | H | H |
| F | $CH_3$ | 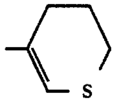 | H | H |
| H | H | 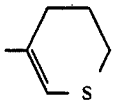 | $CH_3$ | H |
| F | H | 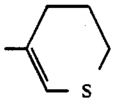 | $CH_3$ | H |
| H | $CH_3$ | 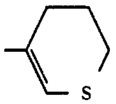 | $CH_3$ | H |
| F | $CH_3$ | 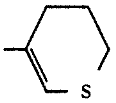 | $CH_3$ | H |
| H | H | 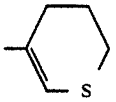 | $CH_3$ | $CH_3$ |
| F | H | 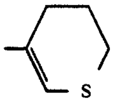 | $CH_3$ | $CH_3$ |
| H | $CH_3$ | 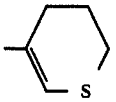 | $CH_3$ | $CH_3$ |
| F | $CH_3$ | 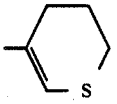 | $CH_3$ | $CH_3$ |
| H | H | 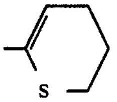 | $CH_3$ | $CH_3$ |
TABLE III-continued
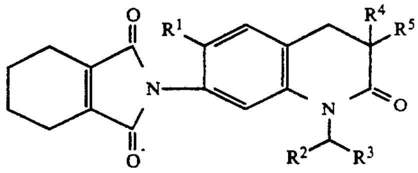
| $R^1$ | $R^2$ | $R^3$ | $R^4$ | $R^5$ |
|---|---|---|---|---|
| F | H | 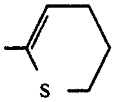 | $CH_3$ | $CH_3$ |
| H | $CH_3$ | 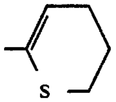 | $CH_3$ | $CH_3$ |
| F | $CH_3$ | 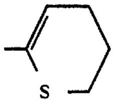 | $CH_3$ | $CH_3$ |
| H | H | 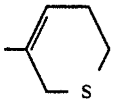 | H | H |
| F | H | 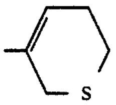 | H | H |
| H | $CH_3$ | 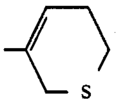 | H | H |
| F | $CH_3$ | 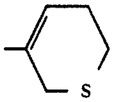 | H | H |
| H | H | 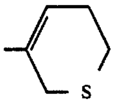 | $CH_3$ | H |
| F | H | 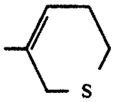 | $CH_3$ | H |
| H | $CH_3$ | 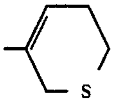 | $CH_3$ | H |
| F | $CH_3$ | 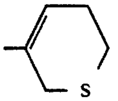 | $CH_3$ | H |

TABLE III-continued
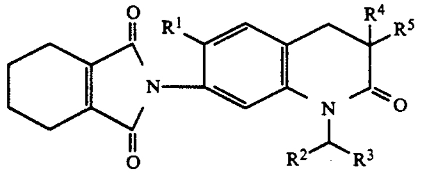
| R1 | R2 | R3 | R4 | R5 |
|---|---|---|---|---|
| H | H | 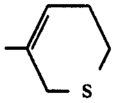 | $CH_3$ | $CH_3$ |
| F | H | 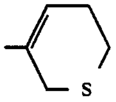 | $CH_3$ | $CH_3$ |
| H | $CH_3$ | 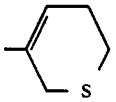 | $CH_3$ | $CH_3$ |
| F | $CH_3$ | 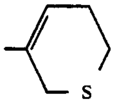 | $CH_3$ | $CH_3$ |
| H | H | 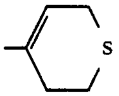 | H | H |
| F | H | 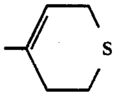 | H | H |
| H | $CH_3$ | 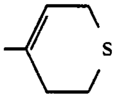 | H | H |
| F | $CH_3$ | 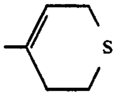 | H | H |
| H | H | 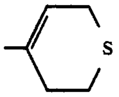 | $CH_3$ | H |
| F | H | 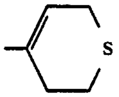 | $CH_3$ | H |
| H | $CH_3$ | 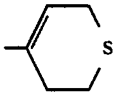 | $CH_3$ | H |
| F | $CH_3$ | 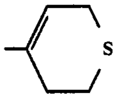 | $CH_3$ | H |
TABLE III-continued
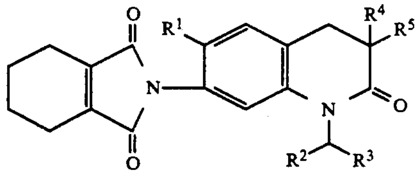
| R1 | R2 | R3 | R4 | R5 |
|---|---|---|---|---|
| H | H | 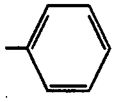 | H | H |
| F | H | 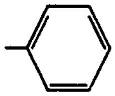 | H | H |
| H | $CH_3$ | 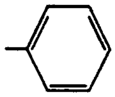 | H | H |
| F | $CH_3$ | 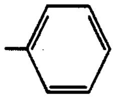 | H | H |
| H | H | 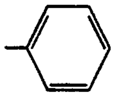 | $CH_3$ | H |
| F | H | 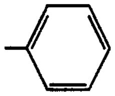 | $CH_3$ | H |
| H | $CH_3$ | 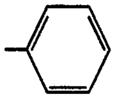 | $CH_3$ | H |
| F | $CH_3$ | 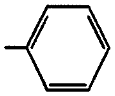 | $CH_3$ | H |
| H | H | 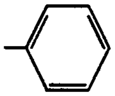 | $CH_3$ | $CH_3$ |
| F | H | 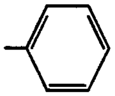 | $CH_3$ | $CH_3$ |
| H | $CH_3$ | 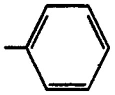 | $CH_3$ | $CH_3$ |
| F | $CH_3$ | 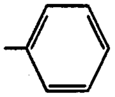 | $CH_3$ | $CH_3$ |

TABLE III-continued

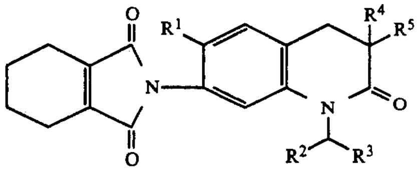

| R[1] | R[2] | R[3] | R[4] | R[5] |
|---|---|---|---|---|
| H | H | 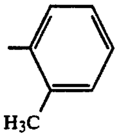 | H | H |
| F | H | 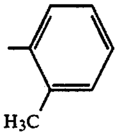 | H | H |
| H | $CH_3$ | 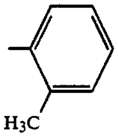 | H | H |
| F | $CH_3$ | 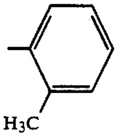 | H | H |
| H | H | 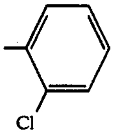 | H | H |
| F | H | 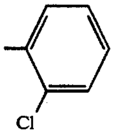 | H | H |
| H | $CH_3$ | 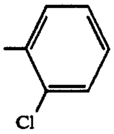 | H | H |
| F | $CH_3$ | 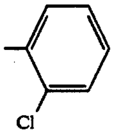 | H | H |
| H | H | 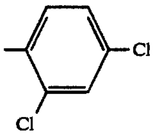 | H | H |

TABLE III-continued

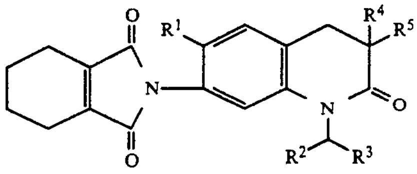

| R[1] | R[2] | R[3] | R[4] | R[5] |
|---|---|---|---|---|
| F | H | 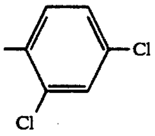 | H | H |
| H | $CH_3$ | 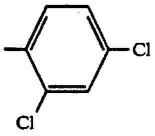 | H | H |
| F | $CH_3$ | 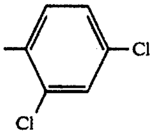 | H | H |

TABLE IIIa

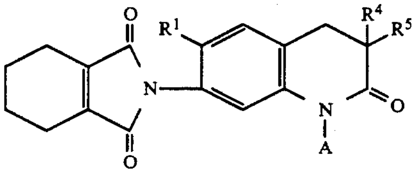

| R[1] | R[4] | R[5] | A |
|---|---|---|---|
| H | H | H | H |
| F | H | H | H |
| H | $CH_3$ | H | H |
| F | $CH_3$ | H | H |
| H | H | H | $CH_3$ |
| F | H | H | $CH_3$ |
| H | $CH_3$ | H | $CH_3$ |
| F | $CH_3$ | H | $CH_3$ |
| H | H | H | $CH_2CH_3$ |
| F | H | H | $CH_2CH_3$ |
| H | $CH_3$ | H | $CH_2CH_3$ |
| F | $CH_3$ | H | $CH_2CH_3$ |
| H | H | H | $CH(CH_3)_2$ |
| F | H | H | $CH(CH_3)_2$ |
| H | $CH_3$ | H | $CH(CH_3)_2$ |
| F | $CH_3$ | H | $CH(CH_3)_2$ |
| H | H | H | $CH_2CH{=}CH_2$ |
| F | H | H | $CH_2CH{=}CH_2$ |
| H | $CH_3$ | H | $CH_2CH{=}CH_2$ |
| F | $CH_3$ | H | $CH_2CH{=}CH_2$ |
| H | H | H | $CH_2CH{=}CHCH_3$ |
| F | H | H | $CH_2CH{=}CHCH_3$ |
| H | $CH_3$ | H | $CH_2CH{=}CHCH_3$ |
| F | $CH_3$ | H | $CH_2CH{=}CHCH_3$ |
| H | H | H | $CH_2CH{\equiv}CH$ |
| F | H | H | $CH_2CH{\equiv}CH$ |
| H | $CH_3$ | H | $CH_2CH{\equiv}CH$ |
| F | $CH_3$ | H | $CH_2CH{\equiv}CH$ |
| H | H | H | $CH_2C{\equiv}CCH_3$ |
| F | H | H | $CH_2C{\equiv}CCH_3$ |
| H | $CH_3$ | H | $CH_2C{\equiv}CCH_3$ |
| F | $CH_3$ | H | $CH_2C{\equiv}CCH_3$ |
| H | H | H | $CH_2OCH_3$ |
| F | H | H | $CH_2OCH_3$ |
| H | $CH_3$ | H | $CH_2OCH_3$ |

TABLE IIIa-continued

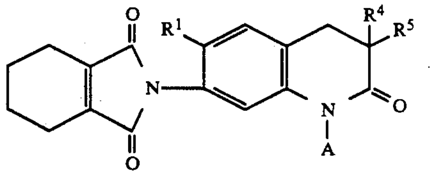

| $R^1$ | $R^4$ | $R^5$ | A |
|---|---|---|---|
| F | $CH_3$ | H | $CH_2OCH_3$ |
| H | H | H | $(CH_2)_2OCH_3$ |
| F | H | H | $(CH_2)_2OCH_3$ |
| H | $CH_3$ | H | $(CH_2)_2OCH_3$ |
| F | $CH_3$ | H | $(CH_2)_2OCH_3$ |
| H | H | H | $CH_2CO_2CH_3$ |
| F | H | H | $CH_2CO_2CH_3$ |
| H | $CH_3$ | H | $CH_2CO_2CH_3$ |
| F | $CH_3$ | H | $CH_2CO_2CH_3$ |
| H | H | H | $CH_2CO_2CH_2CH_3$ |
| F | H | H | $CH_2CO_2CH_2CH_3$ |
| H | $CH_3$ | H | $CH_2CO_2CH_2CH_3$ |
| F | $CH_3$ | H | $CH_2CO_2CH_2CH_3$ |
| H | H | H | $CH(CH_3)CO_2CH_3$ |
| F | H | H | $CH(CH_3)CO_2CH_3$ |
| H | $CH_3$ | H | $CH(CH_3)CO_2CH_3$ |
| F | $CH_3$ | H | $CH(CH_3)CO_2CH_3$ |
| H | H | H | $CH(CH_3)CO_2CH_2CH_3$ |
| F | H | H | $CH(CH_3)CO_2CH_2CH_3$ |
| H | $CH_3$ | H | $CH(CH_3)CO_2CH_2CH_3$ |
| F | $CH_3$ | H | $CH(CH_3)CO_2CH_2CH_3$ |
| H | $CH_3$ | $CH_3$ | H |
| F | $CH_3$ | $CH_3$ | H |
| H | $CH_3$ | $CH_3$ | $CH_3$ |
| F | $CH_3$ | $CH_3$ | $CH_3$ |
| H | $CH_3$ | $CH_3$ | $CH_2CH_3$ |
| F | $CH_3$ | $CH_3$ | $CH_2CH_3$ |
| H | $CH_3$ | $CH_3$ | $CH_2CH{=}CH_2$ |
| F | $CH_3$ | $CH_3$ | $CH_2CH{=}CH_2$ |
| H | $CH_3$ | $CH_3$ | $CH_2C{\equiv}CH$ |
| F | $CH_3$ | $CH_3$ | $CH_2C{\equiv}CH$ |
| H | $CH_3$ | $CH_3$ | $(CH_2)_2OCH_3$ |
| F | $CH_3$ | $CH_3$ | $(CH_2)_2OCH_3$ |
| H | $CH_3$ | $CH_3$ | $CH_2CO_2CH_3$ |
| F | $CH_3$ | $CH_3$ | $CH_2CO_2CH_3$ |
| H | $CH_3$ | $CH_3$ | $CH(CH_3)CO_2CH_3$ |
| F | $CH_3$ | $CH_3$ | $CH(CH_3)CO_2CH_3$ |

TABLE IV

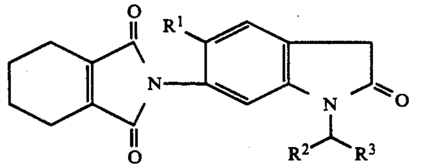

| $R^1$ | $R^2$ | $R^3$ |
|---|---|---|
| H | H | 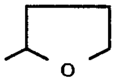 |
| F | H | 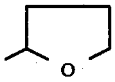 |
| H | $CH_3$ | 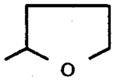 |
| F | $CH_3$ | 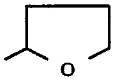 |

TABLE IV-continued

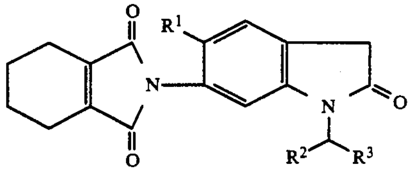

| $R^1$ | $R^2$ | $R^3$ |
|---|---|---|
| H | H | 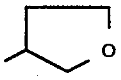 |
| F | H | 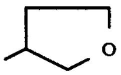 |
| H | $CH_3$ | 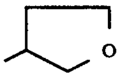 |
| F | $CH_3$ | 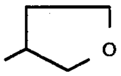 |
| H | H | 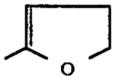 |
| F | H | 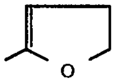 |
| H | $CH_3$ | 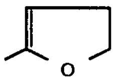 |
| F | $CH_3$ | 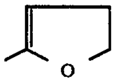 |
| H | H | 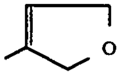 |
| F | H | 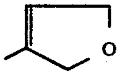 |
| H | $CH_3$ | 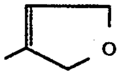 |
| F | $CH_3$ | 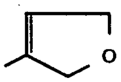 |
| H | H | 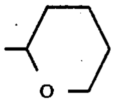 |

TABLE IV-continued
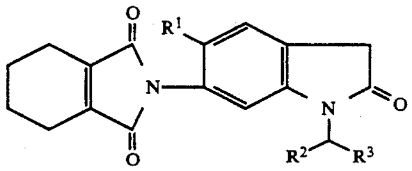
| R¹ | R² | R³ |
| --- | --- | --- |
| F | H | 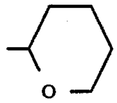 |
| H | $CH_3$ | 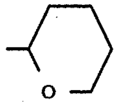 |
| F | $CH_3$ | 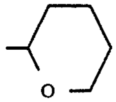 |
| H | H | 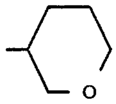 |
| F | H | 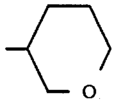 |
| H | $CH_3$ | 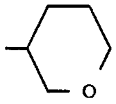 |
| F | $CH_3$ | 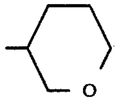 |
| H | H | 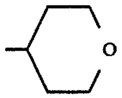 |
| F | H | 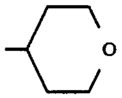 |
| H | $CH_3$ | 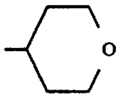 |
| F | $CH_3$ | 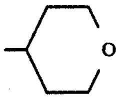 |
TABLE IV-continued
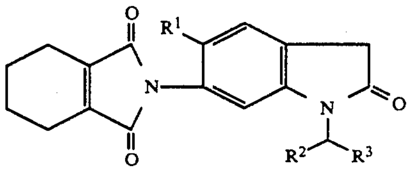
| R¹ | R² | R³ |
| --- | --- | --- |
| H | H | 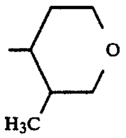 |
| F | H | 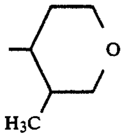 |
| H | $CH_3$ | 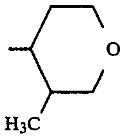 |
| F | $CH_3$ | 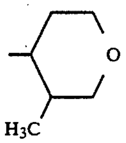 |
| H | H | 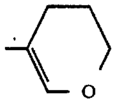 |
| F | H | 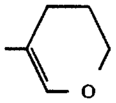 |
| H | $CH_3$ | 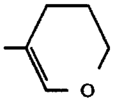 |
| F | $CH_3$ | 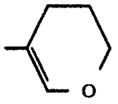 |
| H | H | 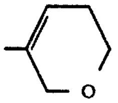 |
| F | H | 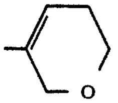 |

TABLE IV-continued
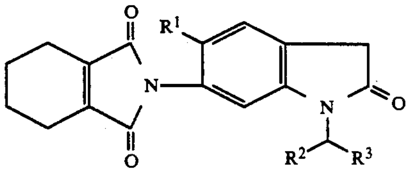
| $R^1$ | $R^2$ | $R^3$ |
|---|---|---|
| H | $CH_3$ | 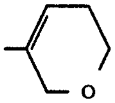 |
| F | $CH_3$ | 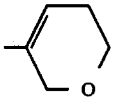 |
| H | H | 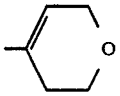 |
| F | H | 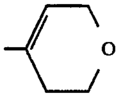 |
| H | $CH_3$ | 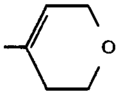 |
| F | $CH_3$ | 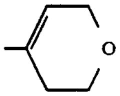 |
| H | H | 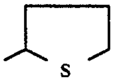 |
| F | H | 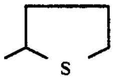 |
| H | $CH_3$ | 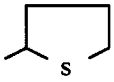 |
| F | $CH_3$ | 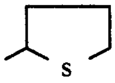 |
| H | H | 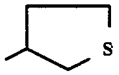 |
| F | H | 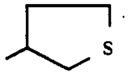 |
| H | $CH_3$ | 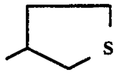 |
TABLE IV-continued
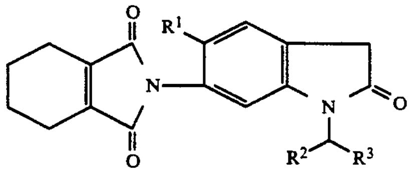
| $R^1$ | $R^2$ | $R^3$ |
|---|---|---|
| F | $CH_3$ | 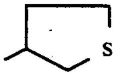 |
| H | H | 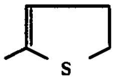 |
| F | H | 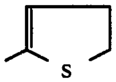 |
| H | $CH_3$ | 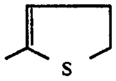 |
| F | $CH_3$ | 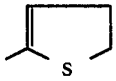 |
| H | H | 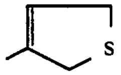 |
| F | H | 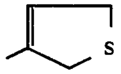 |
| H | $CH_3$ | 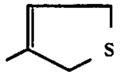 |
| F | $CH_3$ | 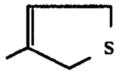 |
| H | H | 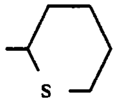 |
| F | H | 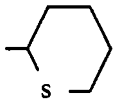 |
| H | $CH_3$ | 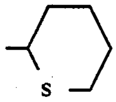 |
| F | $CH_3$ | 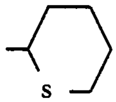 |

TABLE IV-continued
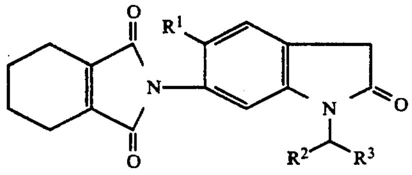
| $R^1$ | $R^2$ | $R^3$ |
|---|---|---|
| H | H | 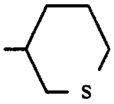 |
| F | H | 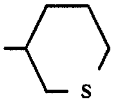 |
| H | $CH_3$ | 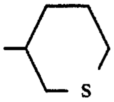 |
| F | $CH_3$ | 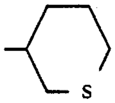 |
| H | H | 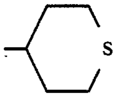 |
| F | H | 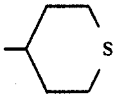 |
| H | $CH_3$ | 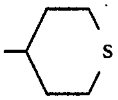 |
| F | $CH_3$ | 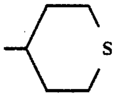 |
| H | H | 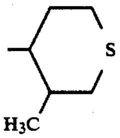 |
| F | H | 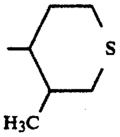 |
| H | $CH_3$ | 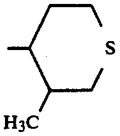 |
TABLE IV-continued
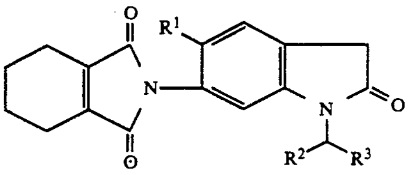
| $R^1$ | $R^2$ | $R^3$ |
|---|---|---|
| F | $CH_3$ | 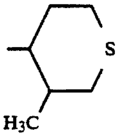 |
| H | H | 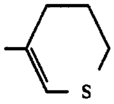 |
| F | H | 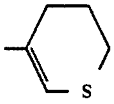 |
| H | $CH_3$ | 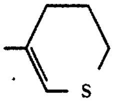 |
| F | $CH_3$ | 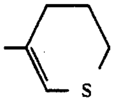 |
| H | H | 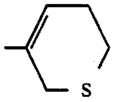 |
| F | H | 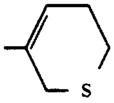 |
| H | $CH_3$ | 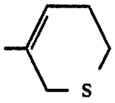 |
| F | $CH_3$ | 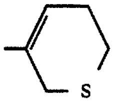 |
| H | H | 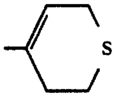 |
| F | H | 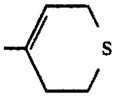 |

TABLE IV-continued
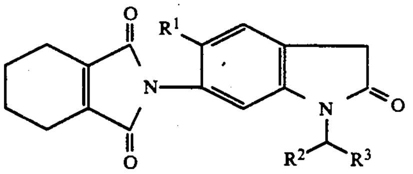
| R1 | R2 | R3 |
|---|---|---|
| H | $CH_3$ | 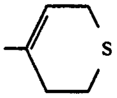 |
| F | $CH_3$ | 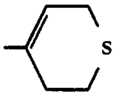 |
| H | H | 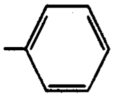 |
| F | H | 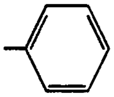 |
| H | $CH_3$ | 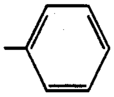 |
| F | $CH_3$ | 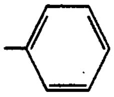 |
| H | H | 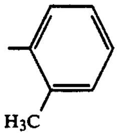 |
| F | H | 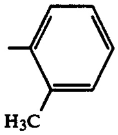 |
| H | $CH_3$ | 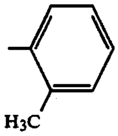 |
| F | $CH_3$ | 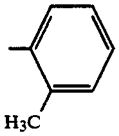 |
TABLE IV-continued
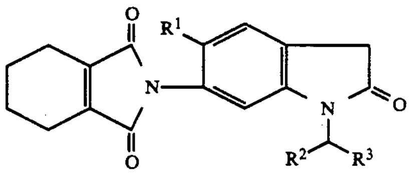
| R1 | R2 | R3 |
|---|---|---|
| H | H | 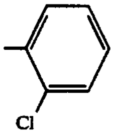 |
| F | H | 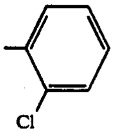 |
| H | $CH_3$ | 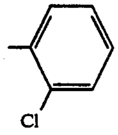 |
| F | $CH_3$ | 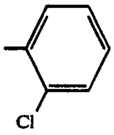 |
| H | H | 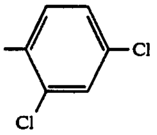 |
| F | H | 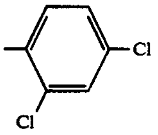 |
| H | $CH_3$ | 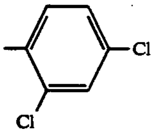 |
| F | $CH_3$ | 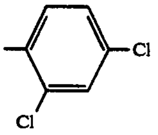 |

TABLE IVa

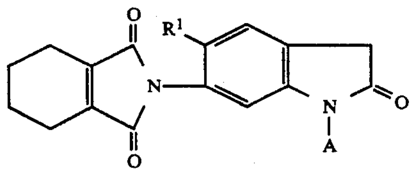

| $R^1$ | A |
|---|---|
| H | H |
| F | H |
| H | $CH_3$ |
| F | $CH_3$ |
| H | $CH_2CH_3$ |
| F | $CH_2CH_3$ |
| H | $CH(CH_3)_2$ |
| F | $CH(CH_3)_2$ |
| H | $CH_2CH{=}CH_2$ |
| F | $CH_2CH{=}CH_2$ |
| H | $CH_2CH{=}CHCH_3$ |
| F | $CH_2CH{=}CHCH_3$ |
| H | $CH_2C{\equiv}CH$ |
| F | $CH_2C{\equiv}CH$ |
| H | $CH_2C{\equiv}CCH_3$ |
| F | $CH_2C{\equiv}CCH_3$ |
| H | $CH_2OCH_3$ |
| F | $CH_2OCH_3$ |
| H | $(CH_2)_2OCH_3$ |
| F | $(CH_2)_2OCH_3$ |
| H | $CH_2CO_2CH_3$ |
| F | $CH_2CO_2CH_3$ |
| H | $CH_2CO_2CH_2CH_3$ |
| F | $CH_2CO_2CH_2CH_3$ |
| H | $CH(CH_3)CO_2CH_3$ |
| F | $CH(CH_3)CO_2CH_3$ |
| H | $CH(CH_3)CO_2CH_2CH_3$ |
| F | $CH(CH_3)CO_2CH_2CH_3$ |

TABLE V

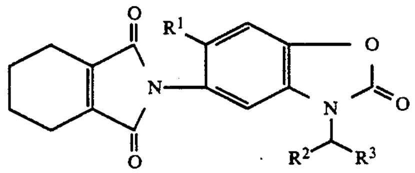

| $R^1$ | $R^2$ | $R^3$ |
|---|---|---|
| H | H | 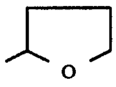 |
| F | H | 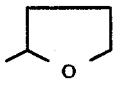 |
| H | $CH_3$ | 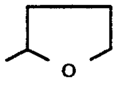 |
| F | $CH_3$ | 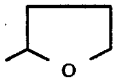 |
| H | H | 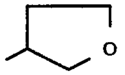 |

TABLE V-continued

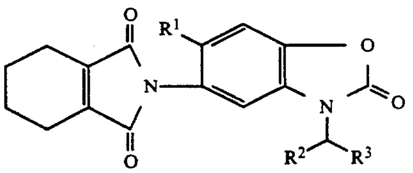

| $R^1$ | $R^2$ | $R^3$ |
|---|---|---|
| F | H | 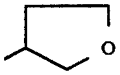 |
| H | $CH_3$ | 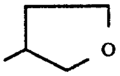 |
| F | $CH_3$ | 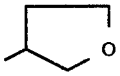 |
| H | H | 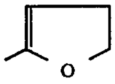 |
| F | H | 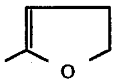 |
| H | $CH_3$ | 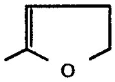 |
| F | $CH_3$ | 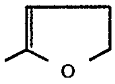 |
| H | H | 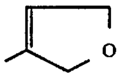 |
| F | H | 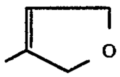 |
| H | $CH_3$ | 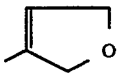 |
| F | $CH_3$ | 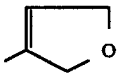 |
| H | H | 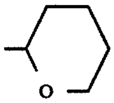 |
| F | H | 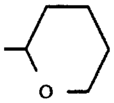 |

TABLE V-continued
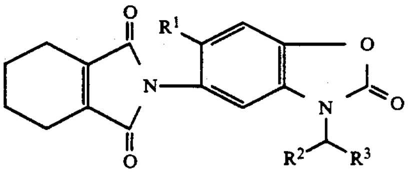
| $R^1$ | $R^2$ | $R^3$ |
|---|---|---|
| H | $CH_3$ | 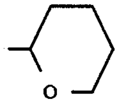 |
| F | $CH_3$ | 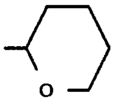 |
| H | H | 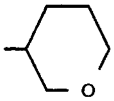 |
| F | H | 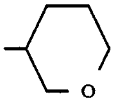 |
| H | $CH_3$ | 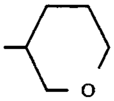 |
| F | $CH_3$ | 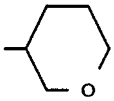 |
| H | H | 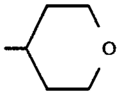 |
| F | H | 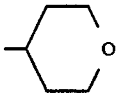 |
| H | $CH_3$ | 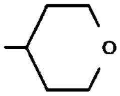 |
| F | $CH_3$ | 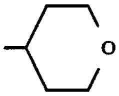 |
| H | H | 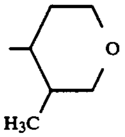 |
TABLE V-continued
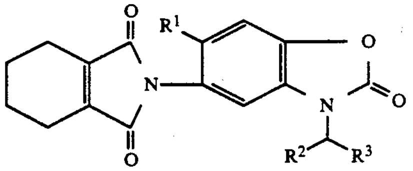
| $R^1$ | $R^2$ | $R^3$ |
|---|---|---|
| F | H | 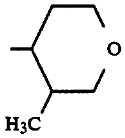 |
| H | $CH_3$ | 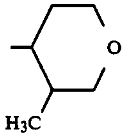 |
| F | $CH_3$ | 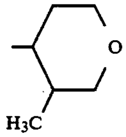 |
| H | H | 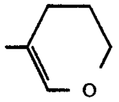 |
| F | H | 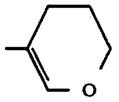 |
| H | $CH_3$ | 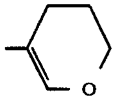 |
| F | $CH_3$ | 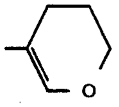 |
| H | H | 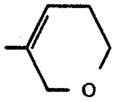 |
| F | H | 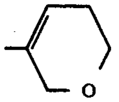 |
| H | $CH_3$ | 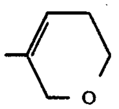 |

TABLE V-continued
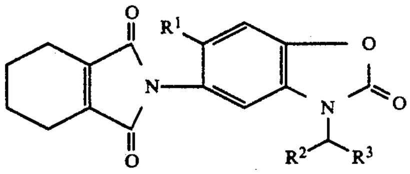
| $R^1$ | $R^2$ | $R^3$ |
|---|---|---|
| F | $CH_3$ | 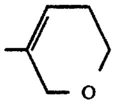 |
| H | H | 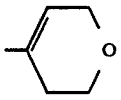 |
| F | H | 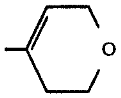 |
| H | $CH_3$ | 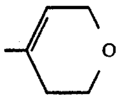 |
| F | $CH_3$ | 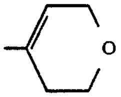 |
| H | H | 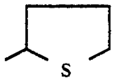 |
| F | H | 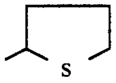 |
| H | $CH_3$ | 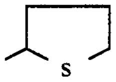 |
| F | $CH_3$ | 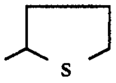 |
| H | H | 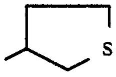 |
| F | H | 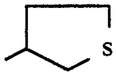 |
| H | $CH_3$ | 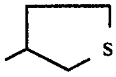 |
| F | $CH_3$ | 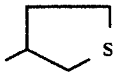 |
TABLE V-continued
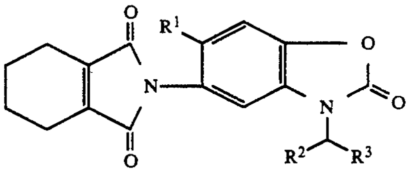
| $R^1$ | $R^2$ | $R^3$ |
|---|---|---|
| H | H | 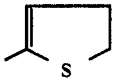 |
| F | H | 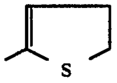 |
| H | $CH_3$ | 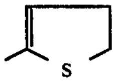 |
| F | $CH_3$ | 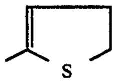 |
| H | H | 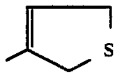 |
| F | H | 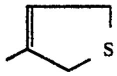 |
| H | $CH_3$ | 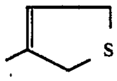 |
| F | $CH_3$ | 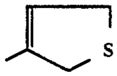 |
| H | H | 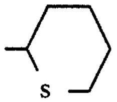 |
| F | H | 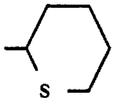 |
| H | $CH_3$ | 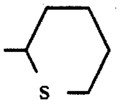 |
| F | $CH_3$ | 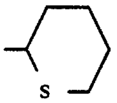 |
| H | H | 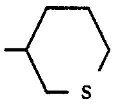 |

TABLE V-continued
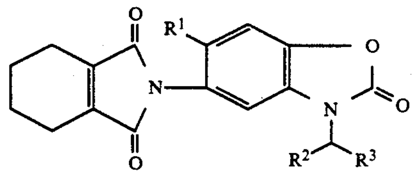
| R1 | R2 | R3 |
|---|---|---|
| F | H | 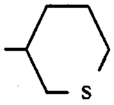 |
| H | $CH_3$ | 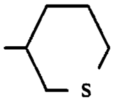 |
| F | $CH_3$ | 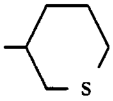 |
| H | H | 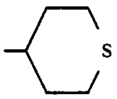 |
| F | H | 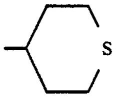 |
| H | $CH_3$ | 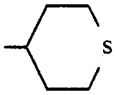 |
| F | $CH_3$ | 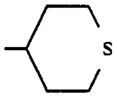 |
| H | H | 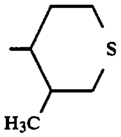 |
| F | H | 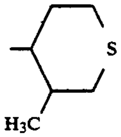 |
| H | $CH_3$ | 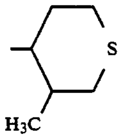 |
TABLE V-continued
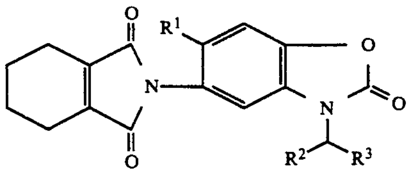
| R1 | R2 | R3 |
|---|---|---|
| F | $CH_3$ | 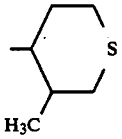 |
| H | H | 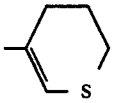 |
| F | H | 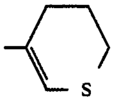 |
| H | $CH_3$ | 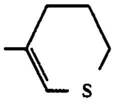 |
| F | $CH_3$ | 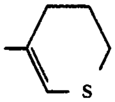 |
| H | H | 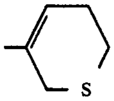 |
| F | H | 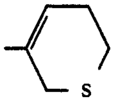 |
| H | $CH_3$ | 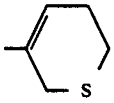 |
| F | $CH_3$ | 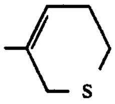 |
| H | H | 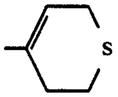 |
| F | H | 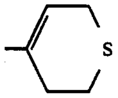 |

TABLE V-continued
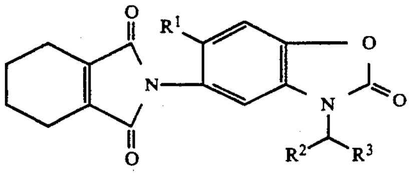
| R[1] | R[2] | R[3] |
|---|---|---|
| H | $CH_3$ | 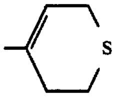 |
| F | $CH_3$ | 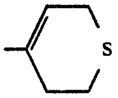 |
| H | H | 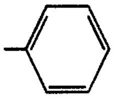 |
| F | H | 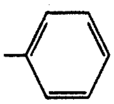 |
| H | $CH_3$ | 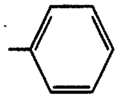 |
| F | $CH_3$ | 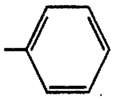 |
| H | H | 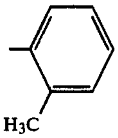 |
| F | H | 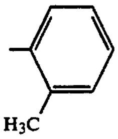 |
| H | $CH_3$ | 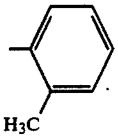 |
| F | $CH_3$ | 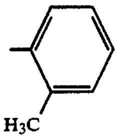 |
TABLE V-continued
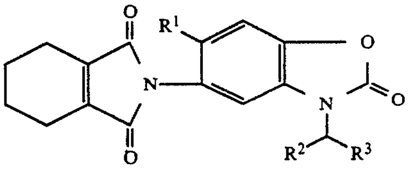
| R[1] | R[2] | R[3] |
|---|---|---|
| H | H | 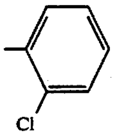 |
| F | H | 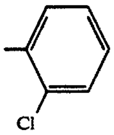 |
| H | $CH_3$ | 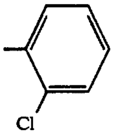 |
| F | $CH_3$ | 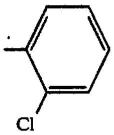 |
| H | H | 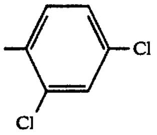 |
| F | H | 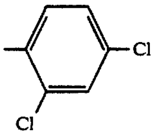 |
| H | $CH_3$ | 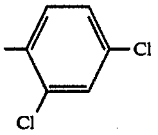 |
| F | $CH_3$ | 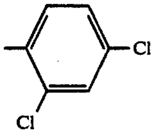 |

TABLE VI
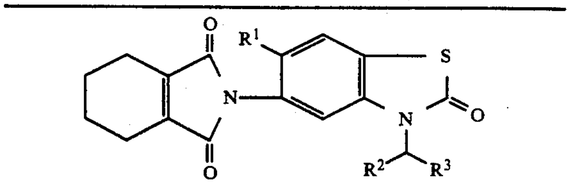
| $R^1$ | $R^2$ | $R^3$ |
|---|---|---|
| H | H | 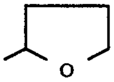 |
| F | H | 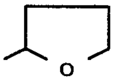 |
| H | $CH_3$ | 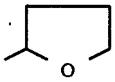 |
| F | $CH_3$ | 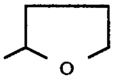 |
| H | H | 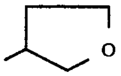 |
| F | H | 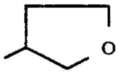 |
| H | $CH_3$ | 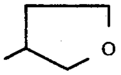 |
| F | $CH_3$ | 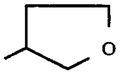 |
| H | H | 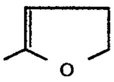 |
| F | H | 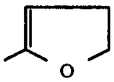 |
| H | $CH_3$ | 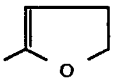 |
| F | $CH_3$ | 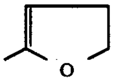 |
| H | H | 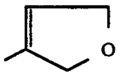 |
| F | H | 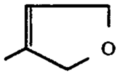 |
TABLE VI-continued
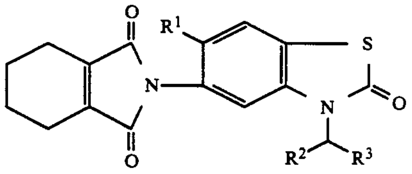
| $R^1$ | $R^2$ | $R^3$ |
|---|---|---|
| H | $CH_3$ | 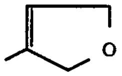 |
| F | $CH_3$ | 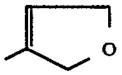 |
| H | H | 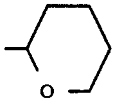 |
| F | H | 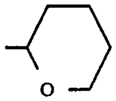 |
| H | $CH_3$ | 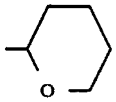 |
| F | $CH_3$ | 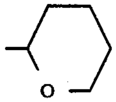 |
| H | H | 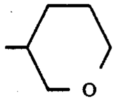 |
| F | H | 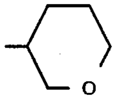 |
| H | $CH_3$ | 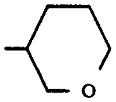 |
| F | $CH_3$ | 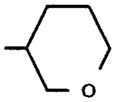 |
| H | H | 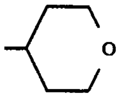 |
| F | H | 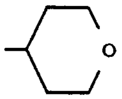 |

TABLE VI-continued
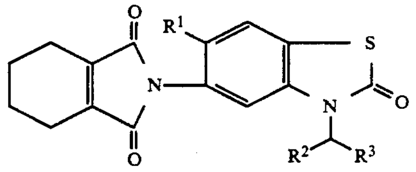
| $R^1$ | $R^2$ | $R^3$ |
|---|---|---|
| H | $CH_3$ | 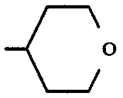 |
| F | $CH_3$ | 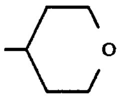 |
| H | H | 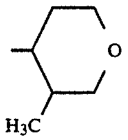 |
| F | H | 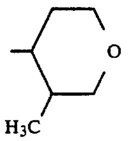 |
| H | $CH_3$ | 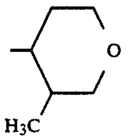 |
| F | $CH_3$ | 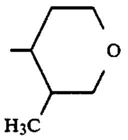 |
| H | H | 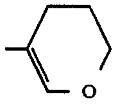 |
| F | H | 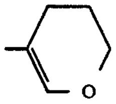 |
| H | $CH_3$ | 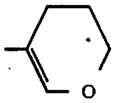 |
| F | $CH_3$ | 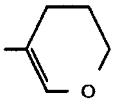 |
TABLE VI-continued
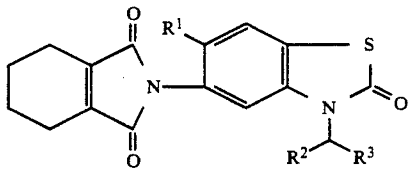
| $R^1$ | $R^2$ | $R^3$ |
|---|---|---|
| H | H | 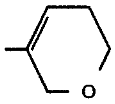 |
| F | H | 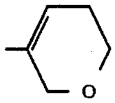 |
| H | $CH_3$ | 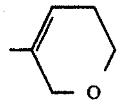 |
| F | $CH_3$ | 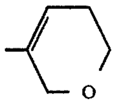 |
| H | H | 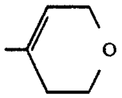 |
| F | H | 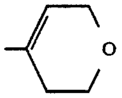 |
| H | $CH_3$ | 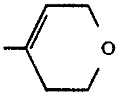 |
| F | $CH_3$ | 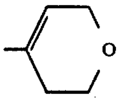 |
| H | H | 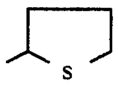 |
| F | H | 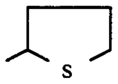 |
| H | $CH_3$ | 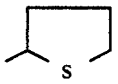 |
| F | $CH_3$ | 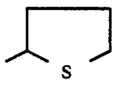 |

TABLE VI-continued
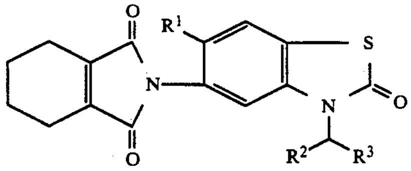
| $R^1$ | $R^2$ | $R^3$ |
|---|---|---|
| H | H | 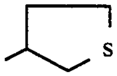 |
| F | H | 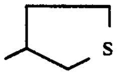 |
| H | $CH_3$ | 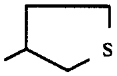 |
| F | $CH_3$ | 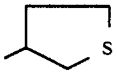 |
| H | H | 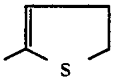 |
| F | H | 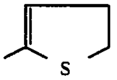 |
| H | $CH_3$ | 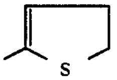 |
| F | $CH_3$ | 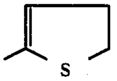 |
| H | H | 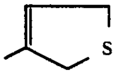 |
| F | H | 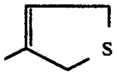 |
| H | $CH_3$ | 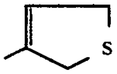 |
| F | $CH_3$ | 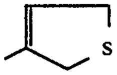 |
| H | H | 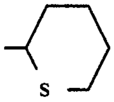 |
TABLE VI-continued
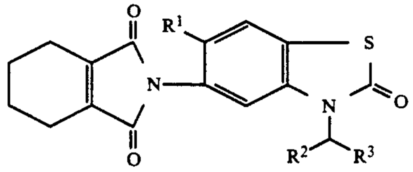
| $R^1$ | $R^2$ | $R^3$ |
|---|---|---|
| F | H | 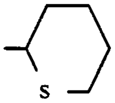 |
| H | $CH_3$ | 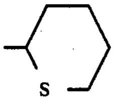 |
| F | $CH_3$ | 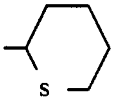 |
| H | H | 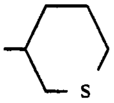 |
| F | H | 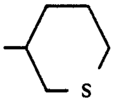 |
| H | $CH_3$ | 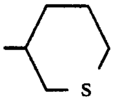 |
| F | $CH_3$ | 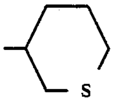 |
| H | H | 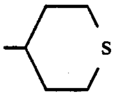 |
| F | H | 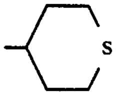 |
| H | $CH_3$ | 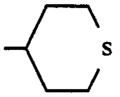 |
| F | $CH_3$ | 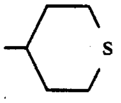 |

TABLE VI-continued
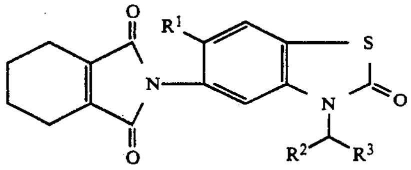
| $R^1$ | $R^2$ | $R^3$ |
|---|---|---|
| H | H | 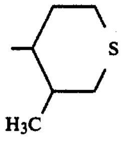 |
| F | H | 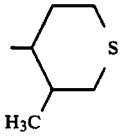 |
| H | $CH_3$ | 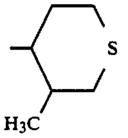 |
| F | $CH_3$ | 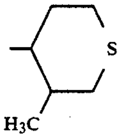 |
| H | H | 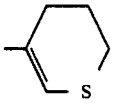 |
| F | H | 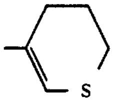 |
| H | $CH_3$ | 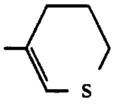 |
| F | $CH_3$ | 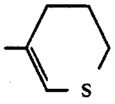 |
| H | H | 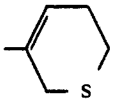 |
| F | H | 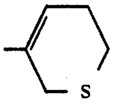 |
TABLE VI-continued
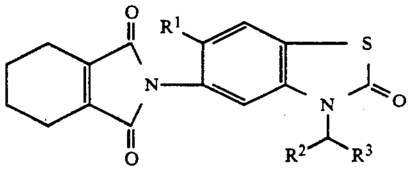
| $R^1$ | $R^2$ | $R^3$ |
|---|---|---|
| H | $CH_3$ | 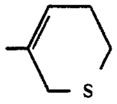 |
| F | $CH_3$ | 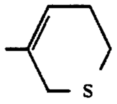 |
| H | H | 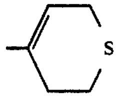 |
| F | H | 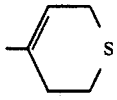 |
| H | $CH_3$ | 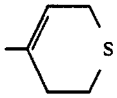 |
| F | $CH_3$ | 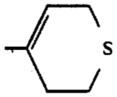 |
| H | H | 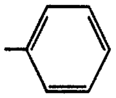 |
| F | H | 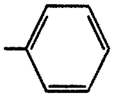 |
| H | $CH_3$ | 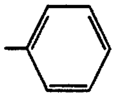 |
| F | $CH_3$ | 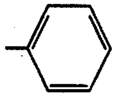 |
| H | H | 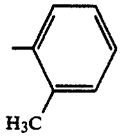 |

TABLE VI-continued

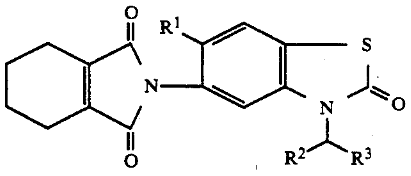

| $R^1$ | $R^2$ | $R^3$ |
|---|---|---|
| F | H | 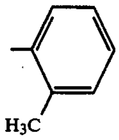 |
| H | $CH_3$ | 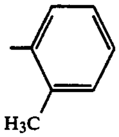 |
| F | $CH_3$ | 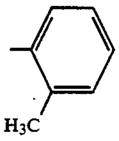 |
| H | H | 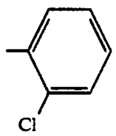 |
| F | H | 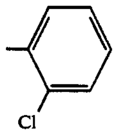 |
| H | $CH_3$ | 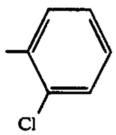 |
| F | $CH_3$ | 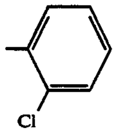 |
| H | H | 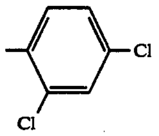 |
| F | H | 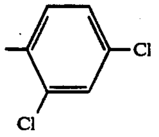 |

TABLE VI-continued

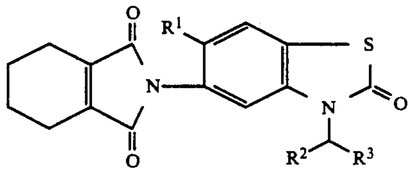

| $R^1$ | $R^2$ | $R^3$ |
|---|---|---|
| H | $CH_3$ | 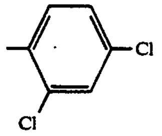 |
| F | $CH_3$ | 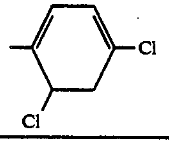 |

The N-aryltetrahydrophthalimide compounds I, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal slats of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90% by weight of active ingredient.

Examples of formulations are given below.

I. 90 parts by weight of compound no. 1.003 is mixed with 10 parts by weight of N-methyl-alpha-pyrrolidone. A mixture is obtained which is suitable for application in the form of very fine drops.

II. 20 parts by weight of compound no. 1.011 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.035 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 3.059 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

In view of the number of application methods available the compounds according to the invention, or agents containing them, may be used in a further large number of crop plants for combating unwanted plants. Examples of such crops are as follows:

V. 20 parts by weight of compound no. 4.047 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1.023 is intimately mixed with 97 parts by weight of particulate kaolin. A dust is obtained containing 3% by weight of the active ingredient.

VII. 30 parts by weight of compound no. 1.033 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 3.067 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The herbicidal agents, or the active ingredients on which they are based, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 5.0, preferably 0.01 to 0.5, kg/ha.

In view of the number of application methods available the compounds according to the invention, or agents containing them, may be used in a further large number of crop plants for combating unwanted plants. Examples of such crops are as follows:

| Botanical Name | Common Name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |

-continued

| Botanical Name | Common Name |
|---|---|
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum (Gossypium arboreum, Gossypium herbaceum, Gossypium vitifolium)* | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| Malus spp. | apple trees |
| *Manihot esculenta* | cassava |
| *Medicago sativa* | alfalfa (lucerne) |
| *Mentha piperita* | peppermint |
| Musa spp. | banana plants |
| *Nicotiana tabacum (N. rustica)* | tobacco |
| *Olea europaea* | olive trees |
| *Oryza sativa* | rice |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor (S. vulgare)* | sorghum |
| *Sorghum dochna* | sorgo |
| *Spinacia oleracea* | spinach |
| *Theobroma cacao* | cacao plants |
| *Trifolium pratense* | red clover |
| *Triticum aestivum* | wheat |
| *Triticum durum* | durum wheat |
| *Vaccinium corymbosum* | blueberries |
| *Vaccinium vitis-idaea* | cranberries |
| *Vicia faba* | tick beans |
| *Vigna sinensis (V. unguiculata)* | cow peas |
| *Vitis vinifera* | grapes |
| *Zea mays* | Indian corn, sweet corn, maize |

To increase the spectrum of action and to achieve synergistic effects, the N-aryltetrahydrophthalimide compounds of the formula I may be mixed and applied togethr with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, phenyloxy- or heteroaryloxy-phenylpropionic acids and salts, esters and amides thereof, etc.

It may also be useful to apply the novel compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

Example 1

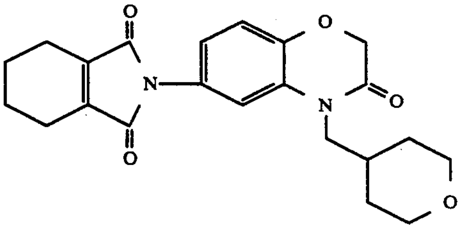

a) 4.9 g (0.03 mol) of 6-amino-3,4-dihydro-2H-1,4-benzoxazin-3-one is introduced into 50 ml of dimethylformamide. At 5° C., 0.79 g (0.033 mol) of sodium hydride is added, and the mixture is stirred for 30 minutes at this temperature. Subsequently, 5.9 g (0.033 mol) of 4-bromomethyltetrahydropyran is added, the mixture is stirred for 3 hours at 60° C., 200 ml of water is added, extraction is carried out twice with methylene chloride, followed by drying and evaporation of the solvent under reduced pressure. There is obtained 5 g (64%) of 4-(tetrahydropyran-4-ylmethyl)-6-amino-3,4-dihydro-2H-1,4-benzoxazin-3-one as an oil.

b) 4.5 g (0.017 mol) of the abovementioned aniline and 2.7 g (0.018 mol) of cyclohexene-1,2-dicarboxylic anhydride are stirred for 3 hours at 70° C. in 70 ml of glacial acetic acid. After the mixture has cooled, 100 ml of water is added and the mixture filtered. The precipitate is washed with water and dried. There is obtained 3.5 g (52%) of N-[4-(tetrahydropyran-4-ylmethyl)-3,4-dihydro-2H-1,4-benzoxazin-3-on-6-yl]-3,4,5,6-tetrahydrophthalimide (m.p. 187°-189° C.) (Table 1, No. 1.033).

TABLE 1

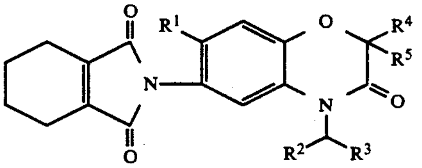

I

| No. | $R^1$ | $R^2$ | $R^3$ | $R^4$ | $R^5$ | m.p.[°C.] |
|---|---|---|---|---|---|---|
| 1.001 | H | H | 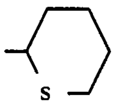 | H | H | |
| 1.002 | F | H | 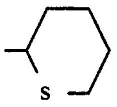 | H | H | |

TABLE 1-continued
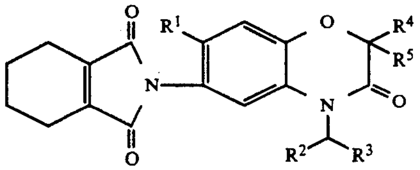
I
| No. | R¹ | R² | R³ | R⁴ | R⁵ | m.p.[°C.] |
|---|---|---|---|---|---|---|
| 1.003 | H | H | 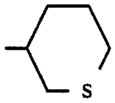 | H | H | 165–166 |
| 1.004 | F | H | 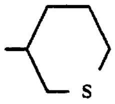 | H | H | 204–206 |
| 1.005 | H | H | 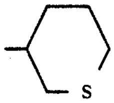 | $CH_3$ | H | |
| 1.006 | F | H | 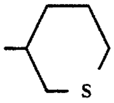 | $CH_3$ | H | |
| 1.007 | H | H | 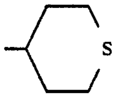 | H | H | |
| 1.008 | F | H | 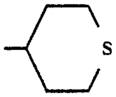 | H | H | |
| 1.009 | H | H | 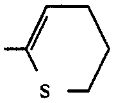 | H | H | |
| 1.010 | F | H | 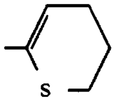 | H | H | |
| 1.011 | H | H | 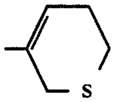 | H | H | 140–142 |
| 1.012 | F | H | 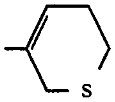 | H | H | |
| 1.013 | H | H | 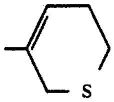 | $CH_3$ | H | |
TABLE 1-continued
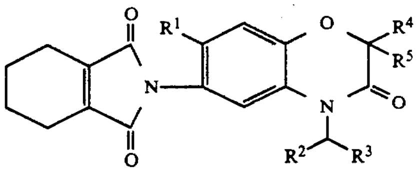
I
| No. | R¹ | R² | R³ | R⁴ | R⁵ | m.p.[°C.] |
|---|---|---|---|---|---|---|
| 1.014 | F | H | 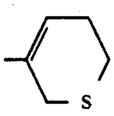 | $CH_3$ | H | |
| 1.015 | H | H | 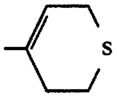 | H | H | |
| 1.016 | F | H | 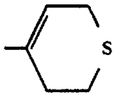 | H | H | |
| 1.017 | H | H | 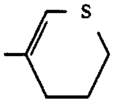 | H | H | |
| 1.018 | F | H | 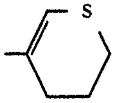 | H | H | |
| 1.019 | H | H | 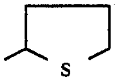 | H | H | |
| 1.020 | F | H | 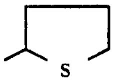 | H | H | |
| 1.021 | H | H | 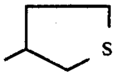 | H | H | |
| 1.022 | F | H | 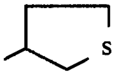 | H | H | |
| 1.023 | H | H | 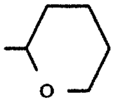 | H | H | 145–147 |
| 1.024 | F | H | 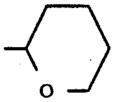 | H | H | |
| 1.025 | H | H | 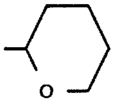 | $CH_3$ | H | |

TABLE 1-continued
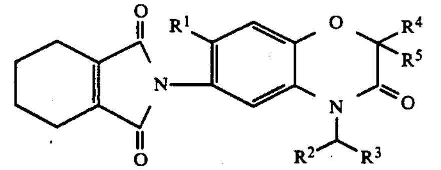
I
| No. | $R^1$ | $R^2$ | $R^3$ | $R^4$ | $R^5$ | m.p.[°C.] |
|---|---|---|---|---|---|---|
| 1.026 | F | H | 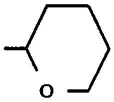 | $CH_3$ | H | |
| 1.027 | H | H | 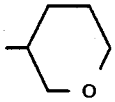 | H | H | 138-140 |
| 1.028 | F | H | 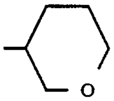 | H | H | 70 (Zers.) |
| 1.029 | H | H | 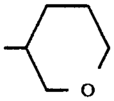 | $CH_3$ | H | 145-147 |
| 1.030 | F | H | 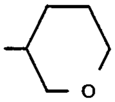 | $CH_3$ | H | |
| 1.031 | H | $CH_3$ | 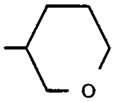 | H | H | |
| 1.032 | F | $CH_3$ | 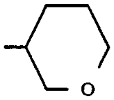 | H | H | |
| 1.033 | H | H | 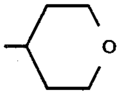 | H | H | 187-189 |
| 1.034 | F | H | 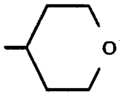 | H | H | |
| 1.035 | H | H | 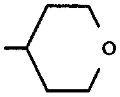 | $CH_3$ | H | 150-152 |
| 1.036 | F | H | 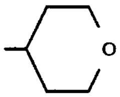 | $CH_3$ | H | |
TABLE 1-continued
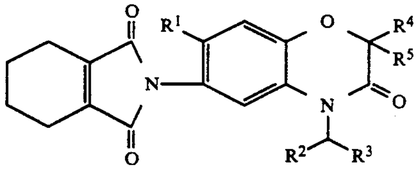
I
| No. | $R^1$ | $R^2$ | $R^3$ | $R^4$ | $R^5$ | m.p.[°C.] |
|---|---|---|---|---|---|---|
| 1.037 | H | H | 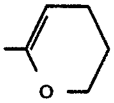 | H | H | |
| 1.038 | F | H | 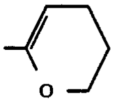 | H | H | |
| 1.039 | H | H | 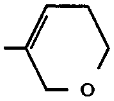 | H | H | |
| 1.040 | F | H | 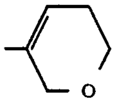 | H | H | 178-179 |
| 1.041 | H | H | 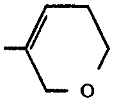 | $CH_3$ | H | |
| 1.042 | F | H | 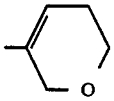 | $CH_3$ | H | |
| 1.043 | H | H | 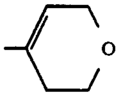 | H | H | |
| 1.044 | F | H | 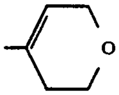 | H | H | |
| 1.045 | H | H | 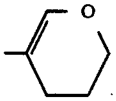 | H | H | |
| 1.046 | F | H | 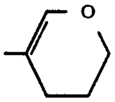 | H | H | |
| 1.047 | H | H | 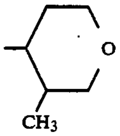 | H | H | |

TABLE 1-continued
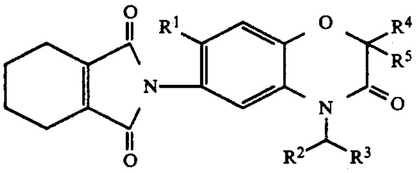
I
| No. | $R^1$ | $R^2$ | $R^3$ | $R^4$ | $R^5$ | m.p.[°C.] |
|---|---|---|---|---|---|---|
| 1.048 | F | H | 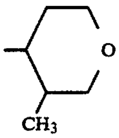 | H | H | |
| 1.049 | H | H | 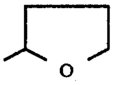 | H | H | 127-129 |
| 1.050 | F | H | 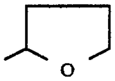 | H | H | |
| 1.051 | H | H | 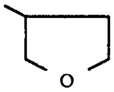 | H | H | |
| 1.052 | F | H | 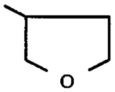 | H | H | |
| 1.053 | H | H | 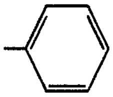 | H | H | 178-180 |
| 1.054 | F | H | 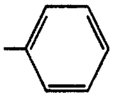 | H | H | |
| 1.055 | H | H | 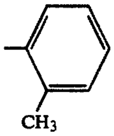 | H | H | 157-168 |
| 1.056 | F | H | 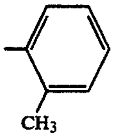 | H | H | |
| 1.057 | H | H | 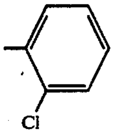 | H | H | 177-178 |
TABLE 1-continued
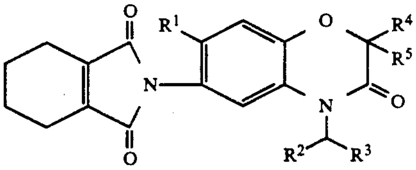
I
| No. | $R^1$ | $R^2$ | $R^3$ | $R^4$ | $R^5$ | m.p.[°C.] |
|---|---|---|---|---|---|---|
| 1.058 | F | H | 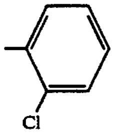 | H | H | |
TABLE 2
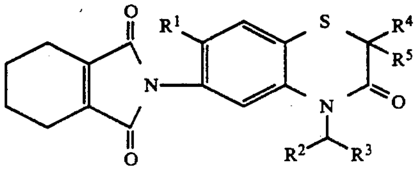
I
| No. | $R^1$ | $R^2$ | $R^3$ | $R^4$ | $R^5$ | m.p.[°C.] |
|---|---|---|---|---|---|---|
| 2.001 | H | H | 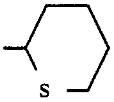 | H | H | |
| 2.002 | F | H | 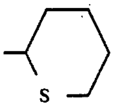 | H | H | |
| 2.003 | H | H | 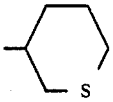 | H | H | |
| 2.004 | F | H | 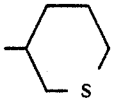 | H | H | |
| 2.005 | H | H | 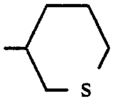 | $CH_3$ | H | |
| 2.006 | F | H | 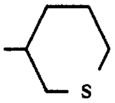 | $CH_3$ | H | |
| 2.007 | H | H | 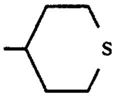 | H | H | |
| 2.008 | F | H | 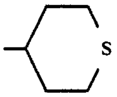 | H | H | |

TABLE 2-continued
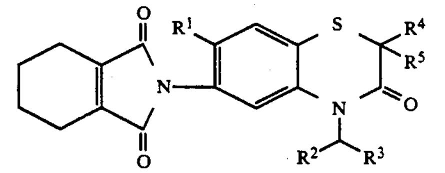
I
| No. | R1 | R2 | R3 | R4 | R5 | m.p.[°C.] |
|---|---|---|---|---|---|---|
| 2.009 | H | H | 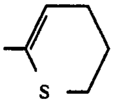 | H | H | |
| 2.010 | F | H | 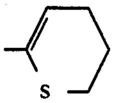 | H | H | |
| 2.011 | H | H | 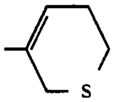 | H | H | |
| 2.012 | F | H | 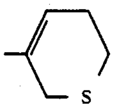 | H | H | |
| 2.013 | H | H | 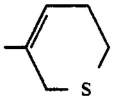 | $CH_3$ | H | |
| 2.014 | F | H | 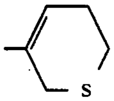 | $CH_3$ | H | |
| 2.015 | H | H | 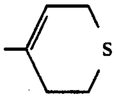 | H | H | |
| 2.016 | F | H | 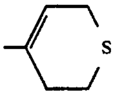 | H | H | |
| 2.017 | H | H | 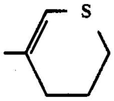 | H | H | |
| 2.018 | F | H | 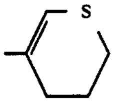 | H | H | |
| 2.019 | H | H | 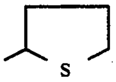 | H | H | |
| 2.020 | F | H | 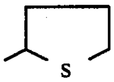 | H | H | |
TABLE 2-continued
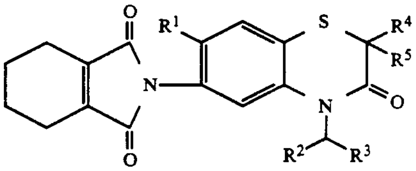
I
| No. | R1 | R2 | R3 | R4 | R5 | m.p.[°C.] |
|---|---|---|---|---|---|---|
| 2.021 | H | H | 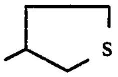 | H | H | |
| 2.022 | F | H | 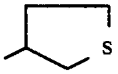 | H | H | |
| 2.023 | H | H | 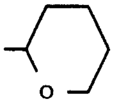 | H | H | |
| 2.024 | F | H | 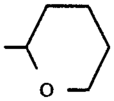 | H | H | |
| 2.025 | H | H | 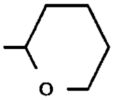 | $CH_3$ | H | |
| 2.026 | F | H | 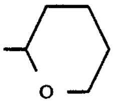 | $CH_3$ | H | |
| 2.027 | H | H | 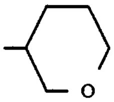 | H | H | |
| 2.028 | F | H | 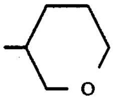 | H | H | |
| 2.029 | H | H | 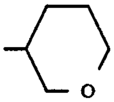 | $CH_3$ | H | |
| 2.030 | F | H | 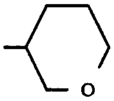 | $CH_3$ | H | |
| 2.031 | H | $CH_3$ | 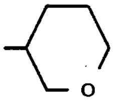 | H | H | |
| 2.032 | F | $CH_3$ | 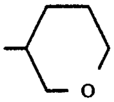 | H | H | |

TABLE 2-continued
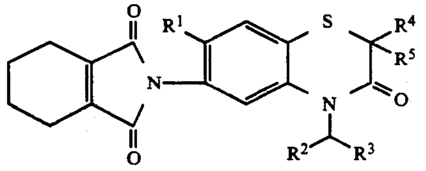
I
| No. | $R^1$ | $R^2$ | $R^3$ | $R^4$ | $R^5$ | m.p.[°C.] |
|---|---|---|---|---|---|---|
| 2.033 | H | H | 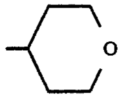 | H | H | |
| 2.034 | F | H | 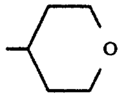 | H | H | |
| 2.035 | H | H | 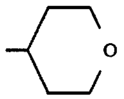 | $CH_3$ | H | |
| 2.036 | F | H | 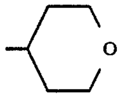 | $CH_3$ | H | |
| 2.037 | H | H | 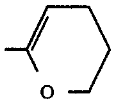 | H | H | |
| 2.038 | F | H | 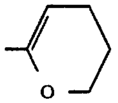 | H | H | |
| 2.039 | H | H | 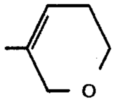 | H | H | |
| 2.040 | F | H | 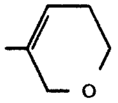 | H | H | |
| 2.041 | H | H | 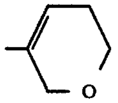 | $CH_3$ | H | |
| 2.042 | F | H | 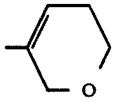 | $CH_3$ | H | |
| 2.043 | H | H | 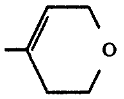 | H | H | |
TABLE 2-continued
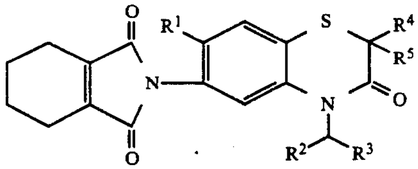
I
| No. | $R^1$ | $R^2$ | $R^3$ | $R^4$ | $R^5$ | m.p.[°C.] |
|---|---|---|---|---|---|---|
| 2.044 | F | H | 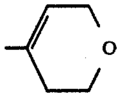 | H | H | |
| 2.045 | H | H | 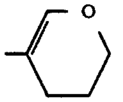 | H | H | |
| 2.046 | F | H | 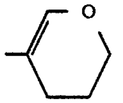 | H | H | |
| 2.047 | H | H | 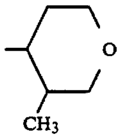 | H | H | |
| 2.048 | F | H | 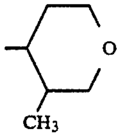 | H | H | |
| 2.049 | H | H | 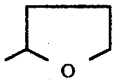 | H | H | |
| 2.050 | F | H | 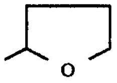 | H | H | |
| 2.051 | H | H | 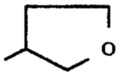 | H | H | |
| 2.052 | F | H | 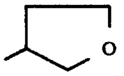 | H | H | |
| 2.053 | H | H | 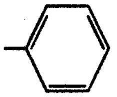 | H | H | |
| 2.054 | F | H | 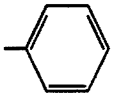 | H | H | |

TABLE 2-continued

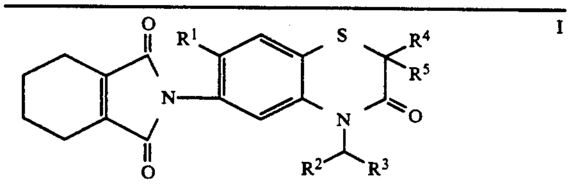
I

| No. | R[1] | R[2] | R[3] | R[4] | R[5] | m.p.[°C.] |
|---|---|---|---|---|---|---|
| 2.055 | H | H | 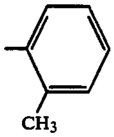 | H | H | |
| 2.056 | F | H | 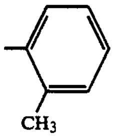 | H | H | |
| 2.057 | H | H | 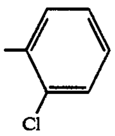 | H | H | |
| 2.058 | F | H | 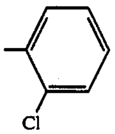 | H | H | |

TABLE 2a

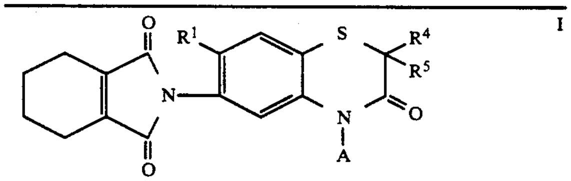
I

| No. | R[1] | A | R[4] | R[5] | m.p.[°C.] |
|---|---|---|---|---|---|
| 2.059 | H | H | H | H | 230–231 |
| 2.060 | F | H | H | H | |
| 2.061 | H | $CH_3$ | H | H | |
| 2.062 | F | $CH_3$ | H | H | |
| 2.063 | H | $CH_2CH_3$ | H | H | |
| 2.064 | F | $CH_2CH_3$ | H | H | |
| 2.065 | H | $CH(CH_3)_2$ | H | H | |
| 2.066 | F | $CH(CH_3)_2$ | H | H | |
| 2.067 | H | $CH_2CH{=}CH_2$ | H | H | |
| 2.068 | F | $CH_2CH{=}CH_2$ | H | H | |
| 2.069 | H | $CH_2C{\equiv}CH$ | H | H | 193–194 |
| 2.070 | F | $CH_2C{\equiv}CH$ | H | H | |
| 2.071 | H | $CH_2OCH_3$ | H | H | |
| 2.072 | F | $CH_2OCH_3$ | H | H | |
| 2.073 | H | $CH_2CH_2OCH_3$ | H | H | |
| 2.074 | F | $CH_2CH_2OCH_3$ | H | H | |
| 2.075 | H | $CH_2CO_2CH_3$ | H | H | |
| 2.076 | F | $CH_2CO_2CH_3$ | H | H | |
| 2.077 | H | $CH_2CO_2CH_2CH_3$ | H | H | |
| 2.078 | F | $CH_2CO_2CH_2CH_3$ | H | H | |
| 2.079 | H | $CH(CH_3)CO_2CH_3$ | H | H | |
| 2.080 | F | $CH(CH_3)CO_2CH_3$ | H | H | |
| 2.081 | H | $CH(CH_3)CO_2CH_2CH_3$ | H | H | |
| 2.082 | F | $CH(CH_3)CO_2CH_2CH_3$ | H | H | |
| 2.083 | H | $CH(CH_3)CO_2CH_2CH_3$ | $CH_3$ | H | |
| 2.084 | F | $CH(CH_3)CO_2CH_2CH_3$ | $CH_3$ | H | |
| 2.085 | H | $CH_2CH{=}CH_2$ | $CH_3$ | H | |

TABLE 2a-continued

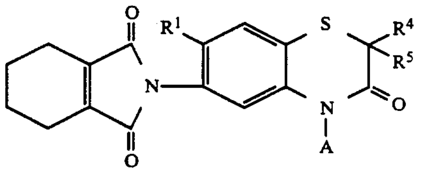
I

| No. | R[1] | A | R[4] | R[5] | m.p.[°C.] |
|---|---|---|---|---|---|
| 2.086 | F | $CH_2CH{=}CH_2$ | $CH_3$ | H | |
| 2.087 | H | $CH_2C{\equiv}CH$ | $CH_3$ | H | |
| 2.088 | F | $CH_2C{\equiv}CH$ | $CH_3$ | H | |

TABLE 3

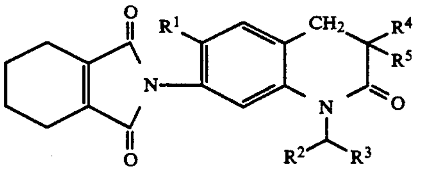
I

| No. | R[1] | R[2] | R[3] | R[4] | R[5] | m.p.[°C.] |
|---|---|---|---|---|---|---|
| 3.001 | H | H | 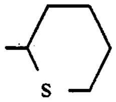 | H | H | |
| 3.002 | F | H | 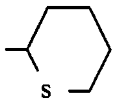 | H | H | |
| 3.003 | H | H | 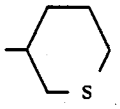 | H | H | |
| 3.004 | F | H | 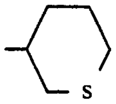 | H | H | |
| 3.005 | H | H | 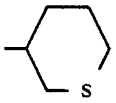 | $CH_3$ | H | |
| 3.006 | F | H | 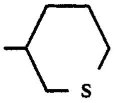 | $CH_3$ | H | |
| 3.007 | H | H | 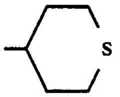 | H | H | |
| 3.008 | F | H | 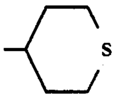 | H | H | |
| 3.009 | H | H | 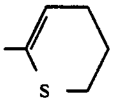 | H | H | |

TABLE 3-continued
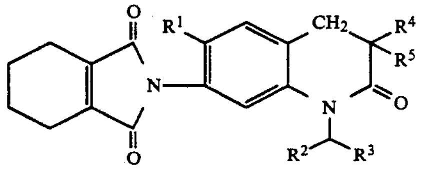
I
| No. | R1 | R2 | R3 | R4 | R5 | m.p.[°C.] |
|---|---|---|---|---|---|---|
| 3.010 | F | H | 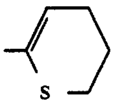 | H | H | |
| 3.011 | H | H | 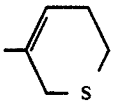 | H | H | 147-149 |
| 3.012 | F | H | 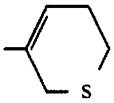 | H | H | |
| 3.013 | H | H | 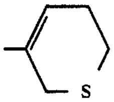 | $CH_3$ | H | |
| 3.014 | F | H | 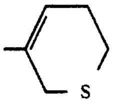 | $CH_3$ | H | |
| 3.015 | H | H | 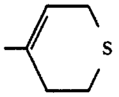 | H | H | |
| 3.016 | F | H | 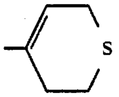 | H | H | |
| 3.017 | H | H | 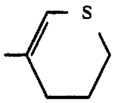 | H | H | |
| 3.018 | F | H | 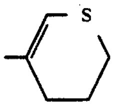 | H | H | |
| 3.019 | H | H | 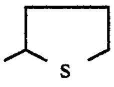 | H | H | |
| 3.020 | F | H | 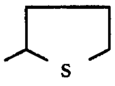 | H | H | |
| 3.021 | H | H | 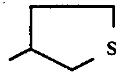 | H | H | |
TABLE 3-continued
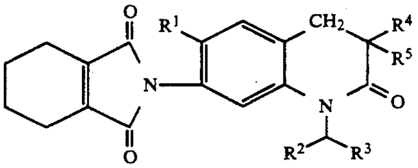
I
| No. | R1 | R2 | R3 | R4 | R5 | m.p.[°C.] |
|---|---|---|---|---|---|---|
| 3.022 | F | H | 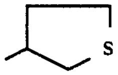 | H | H | |
| 3.023 | H | H | 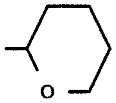 | H | H | |
| 3.024 | F | H | 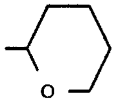 | H | H | |
| 3.025 | H | H | 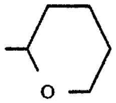 | $CH_3$ | H | |
| 3.026 | F | H | 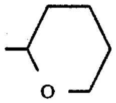 | $CH_3$ | H | |
| 3.027 | H | H | 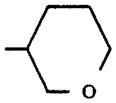 | H | H | 188-190 |
| 3.028 | F | H | 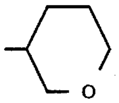 | H | H | |
| 3.029 | H | H | 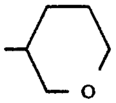 | $CH_3$ | H | |
| 3.030 | F | H | 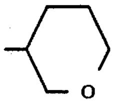 | $CH_3$ | H | |
| 3.031 | H | $CH_3$ | 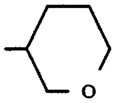 | H | H | |
| 3.032 | F | $CH_3$ | 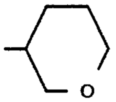 | H | H | |

TABLE 3-continued
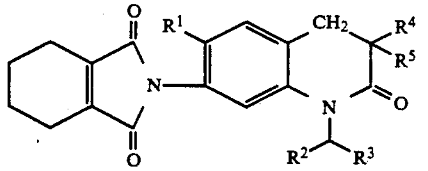
I
| No. | R¹ | R² | R³ | R⁴ | R⁵ | m.p.[°C.] |
|---|---|---|---|---|---|---|
| 3.033 | H | H | 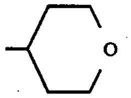 | H | H | |
| 3.034 | F | H | 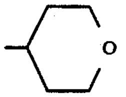 | H | H | |
| 3.035 | H | H | 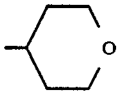 | $CH_3$ | H | |
| 3.036 | F | H | 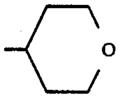 | $CH_3$ | H | |
| 3.037 | H | H | 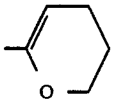 | H | H | |
| 3.038 | F | H | 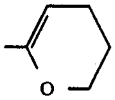 | H | H | |
| 3.039 | H | H | 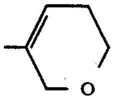 | H | H | |
| 3.040 | F | H | 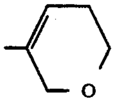 | H | H | |
| 3.041 | H | H | 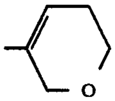 | $CH_3$ | H | |
| 3.042 | F | H | 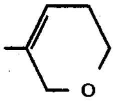 | $CH_3$ | H | |
| 3.043 | H | H | 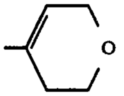 | H | H | |
TABLE 3-continued
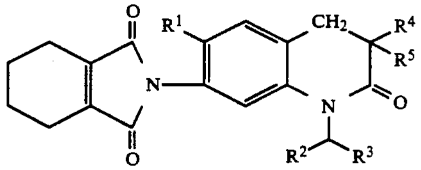
I
| No. | R¹ | R² | R³ | R⁴ | R⁵ | m.p.[°C.] |
|---|---|---|---|---|---|---|
| 3.044 | F | H | 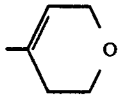 | H | H | |
| 3.045 | H | H | 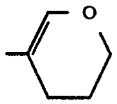 | H | H | |
| 3.046 | F | H | 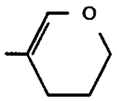 | H | H | |
| 3.047 | H | H | 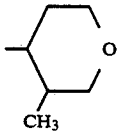 | H | H | |
| 3.048 | F | H | 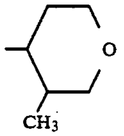 | H | H | |
| 3.049 | H | H | 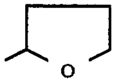 | H | H | |
| 3.050 | F | H | 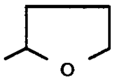 | H | H | |
| 3.051 | H | H | 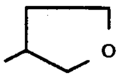 | H | H | |
| 3.052 | F | H | 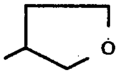 | H | H | |
| 3.053 | H | H | 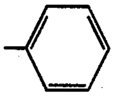 | H | H | |
| 3.054 | F | H | 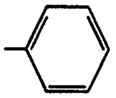 | H | H | |

TABLE 3-continued

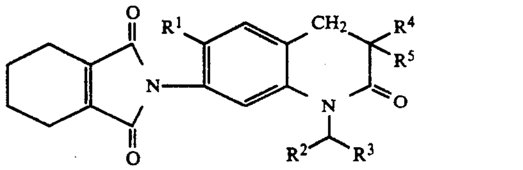

I

| No. | $R^1$ | $R^2$ | $R^3$ | $R^4$ | $R^5$ | m.p.[°C.] |
|---|---|---|---|---|---|---|
| 3.055 | H | H | 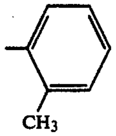 | H | H | 173–175 |
| 3.056 | F | H | 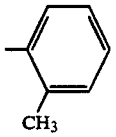 | H | H | |
| 3.057 | H | H | 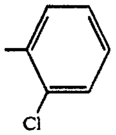 | H | H | |
| 3.058 | F | H | 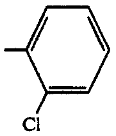 | H | H | |

TABLE 3a

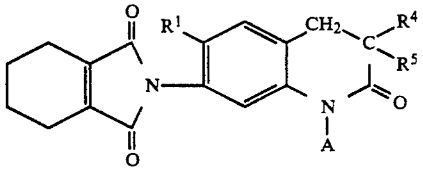

I

| No. | $R^1$ | A | $R^4$ | $R^5$ | m.p.[°C.] |
|---|---|---|---|---|---|
| 3.059 | H | H | H | H | 237–238 |
| 3.060 | F | H | H | H | |
| 3.061 | H | $CH_3$ | H | H | 232–234 |
| 3.062 | F | $CH_3$ | H | H | |
| 3.063 | H | $CH_2CH_3$ | H | H | |
| 3.064 | F | $CH_2CH_3$ | H | H | |
| 3.065 | H | $CH(CH_3)_2$ | H | H | |
| 3.066 | F | $CH(CH_3)_2$ | H | H | |
| 3.067 | H | $CH_2CH{=}CH_2$ | H | H | 168–170 |
| 3.068 | F | $CH_2CH{=}CH_2$ | H | H | |
| 3.069 | H | $CH_2C{\equiv}CH$ | H | H | 196–198 |
| 3.070 | F | $CH_2C{\equiv}CH$ | H | H | |
| 3.071 | H | $CH_2OCH_3$ | H | H | |
| 3.072 | F | $CH_2OCH_3$ | H | H | |
| 3.073 | H | $CH_2CH_2OCH_3$ | H | H | |
| 3.074 | F | $CH_2CH_2OCH_3$ | H | H | |
| 3.075 | H | $CH_2CO_2CH_3$ | H | H | |
| 3.076 | F | $CH_2CO_2CH_3$ | H | H | |
| 3.077 | H | $CH_2CO_2CH_2CH_3$ | H | H | |
| 3.078 | F | $CH_2CO_2CH_2CH_3$ | H | H | |
| 3.079 | H | $CH(CH_3)CO_2CH_3$ | H | H | |
| 3.080 | F | $CH(CH_3)CO_2CH_3$ | H | H | |
| 3.081 | H | $CH(CH_3)CO_2CH_2CH_3$ | H | H | |
| 3.082 | F | $CH(CH_3)CO_2CH_2CH_3$ | H | H | |
| 3.083 | H | $CH(CH_3)CO_2CH_2CH_3$ | $CH_3$ | H | |
| 3.084 | F | $CH(CH_3)CO_2CH_2CH_3$ | $CH_3$ | H | |
| 3.085 | H | $CH_2CH{=}CH_2$ | $CH_3$ | H | |

TABLE 3a-continued

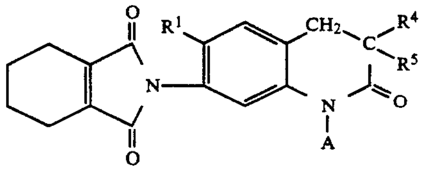

I

| No. | $R^1$ | A | $R^4$ | $R^5$ | m.p.[°C.] |
|---|---|---|---|---|---|
| 3.086 | F | $CH_2CH{=}CH_2$ | $CH_3$ | H | |
| 3.087 | H | $CH_2C{\equiv}CH$ | $CH_3$ | H | |
| 3.088 | F | $CH_2C{\equiv}CH$ | $CH_3$ | H | |

TABLE 4

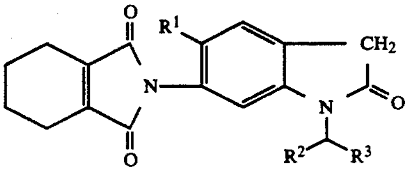

I

| No. | $R^1$ | $R^2$ | $R^3$ | m.p.[°C.] |
|---|---|---|---|---|
| 4.001 | H | H | 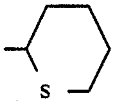 | |
| 4.002 | F | H | 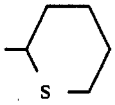 | |
| 4.003 | H | H | 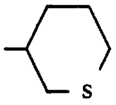 | |
| 4.004 | F | H | 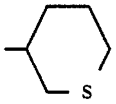 | |
| 4.005 | H | H | 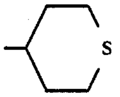 | |
| 4.006 | F | H | 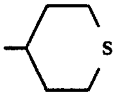 | |
| 4.007 | H | H | 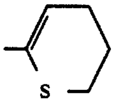 | |
| 4.008 | F | H | 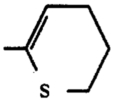 | |
| 4.009 | H | H | 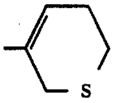 | |

TABLE 4-continued
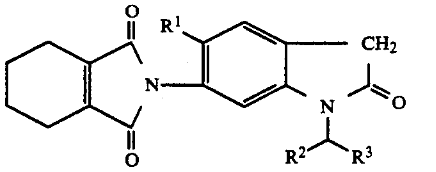
I
| No. | $R^1$ | $R^2$ | $R^3$ | m.p.[°C.] |
|---|---|---|---|---|
| 4.010 | F | H | 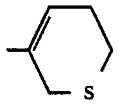 | |
| 4.011 | H | H | 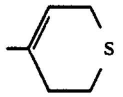 | |
| 4.012 | F | H | 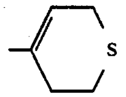 | |
| 4.013 | H | H | 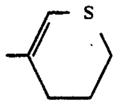 | |
| 4.014 | F | H | 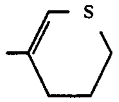 | |
| 4.015 | H | H | 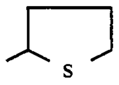 | |
| 4.016 | H | H | 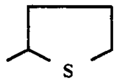 | |
| 4.017 | H | H | 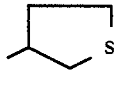 | |
| 4.018 | F | H | 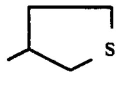 | |
| 4.019 | H | H | 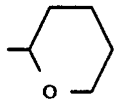 | |
| 4.020 | F | H | 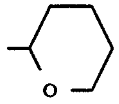 | |
| 4.021 | H | H | 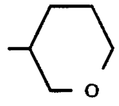 | 150–152 |
TABLE 4-continued
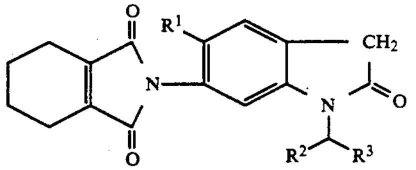
I
| No. | $R^1$ | $R^2$ | $R^3$ | m.p.[°C.] |
|---|---|---|---|---|
| 4.022 | F | H | 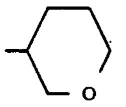 | |
| 4.023 | H | $CH_3$ | 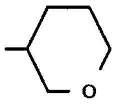 | |
| 4.024 | F | $CH_3$ | 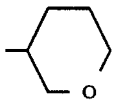 | |
| 4.025 | H | H | 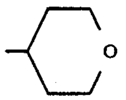 | |
| 4.026 | F | H | 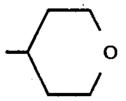 | |
| 4.027 | H | H | 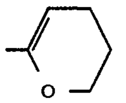 | |
| 4.028 | F | H | 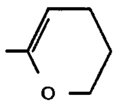 | |
| 4.029 | H | H | 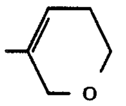 | |
| 4.030 | F | H | 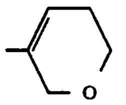 | |
| 4.031 | H | H | 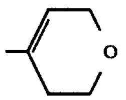 | |
| 4.032 | F | H | 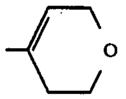 | |

TABLE 4-continued

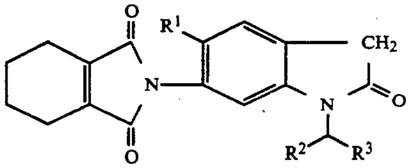

I

| No. | R[1] | R[2] | R[3] | m.p.[°C.] |
|---|---|---|---|---|
| 4.033 | H | H | 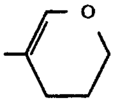 | |
| 4.034 | F | H | 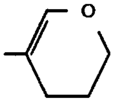 | |
| 4.035 | H | H | 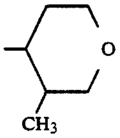 | |
| 4.036 | F | H | 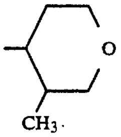 | |
| 4.037 | H | H | 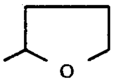 | |
| 4.038 | F | H | 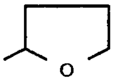 | |
| 4.039 | H | H | 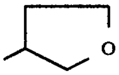 | |
| 4.040 | F | H | 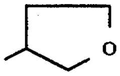 | |
| 4.041 | H | H | 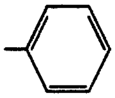 | |
| 4.042 | F | H | 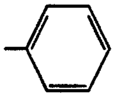 | |
| 4.043 | H | H | 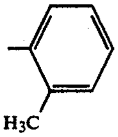 | |

TABLE 4-continued

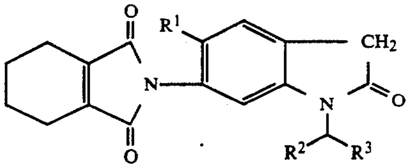

I

| No. | R[1] | R[2] | R[3] | m.p.[°C.] |
|---|---|---|---|---|
| 4.044 | F | H | 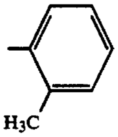 | |
| 4.045 | H | H | 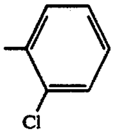 | |
| 4.046 | F | H | 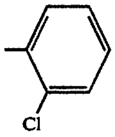 | |

TABLE 4a

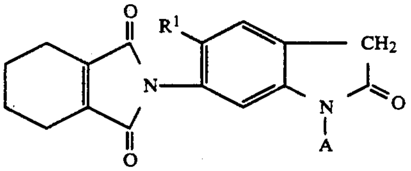

I

| No. | R[1] | A | m.p.[°C.] |
|---|---|---|---|
| 4.047 | H | H | 140–142 |
| 4.048 | F | H | |
| 4.049 | H | $CH_3$ | 205–207 |
| 4.050 | F | $CH_3$ | |
| 4.051 | H | $CH_2CH_3$ | |
| 4.052 | F | $CH_2CH_3$ | |
| 4.053 | H | $CH(CH_3)_2$ | |
| 4.054 | F | $CH(CH_3)_2$ | |
| 4.055 | H | $CH_2CH{=}CH_2$ | |
| 4.056 | F | $CH_2CH{=}CH_2$ | |
| 4.057 | H | $CH_2C{\equiv}CH$ | |
| 4.058 | F | $CH_2C{\equiv}CH$ | |
| 4.059 | H | $CH_2OCH_3$ | |
| 4.060 | F | $CH_2OCH_3$ | |
| 4.061 | H | $CH_2CH_2OCH_3$ | |
| 4.062 | F | $CH_2CH_2OCH_3$ | |
| 4.063 | H | $CH_2CO_2CH_3$ | |
| 4.064 | F | $CH_2CO_2CH_3$ | |
| 4.065 | H | $CH_2CO_2CH_2CH_3$ | |
| 4.066 | F | $CH_2CO_2CH_2CH_3$ | |
| 4.067 | H | $CH(CH_3)CO_2CH_3$ | |
| 4.068 | F | $CH(CH_3)CO_2CH_3$ | |
| 4.069 | H | $CH(CH_3)CO_2CH_2CH_3$ | |
| 4.070 | F | $CH(CH_3)CO_2CH_2CH_3$ | |

TABLE 5
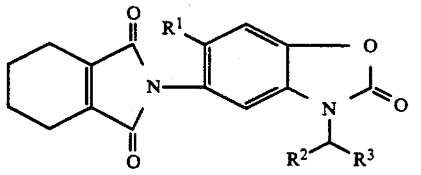
I
| No. | R¹ | R² | R³ | m.p.[°C.] |
|---|---|---|---|---|
| 5.001 | H | H | 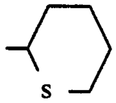 | |
| 5.002 | F | H | 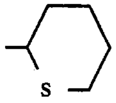 | |
| 5.003 | H | H | 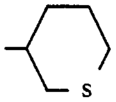 | |
| 5.004 | F | H | 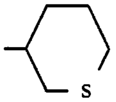 | |
| 5.005 | H | H | 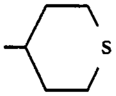 | |
| 5.006 | F | H | 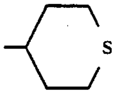 | |
| 5.007 | H | H | 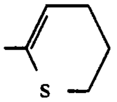 | |
| 5.008 | F | H | 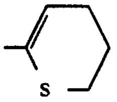 | |
| 5.009 | H | H | 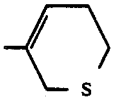 | 147-151 |
| 5.010 | F | H | 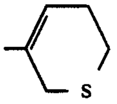 | |
| 5.011 | H | H | 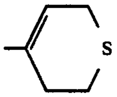 | |
TABLE 5-continued
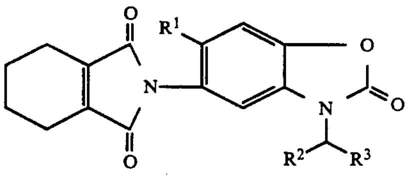
I
| No. | R¹ | R² | R³ | m.p.[°C.] |
|---|---|---|---|---|
| 5.012 | F | H | 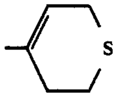 | |
| 5.013 | H | H | 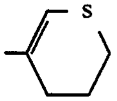 | |
| 5.014 | F | H | 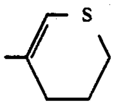 | |
| 5.015 | H | H | 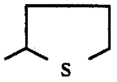 | |
| 5.016 | F | H | 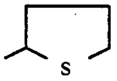 | |
| 5.017 | H | H | 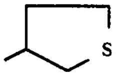 | |
| 5.018 | F | H | 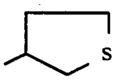 | |
| 5.019 | H | H | 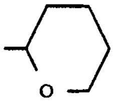 | 133-135 |
| 5.020 | F | H | 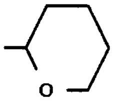 | |
| 5.021 | H | H | 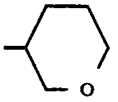 | 167-169 |
| 5.022 | F | H | 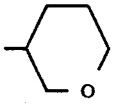 | |
| 5.023 | H | $CH_3$ | 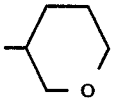 | |

TABLE 5-continued
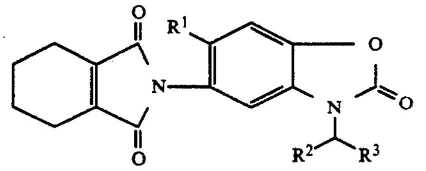
I
| No. | $R^1$ | $R^2$ | $R^3$ | m.p.[°C.] |
| --- | --- | --- | --- | --- |
| 5.024 | F | $CH_3$ | 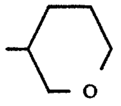 | |
| 5.025 | H | H | 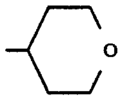 | |
| 5.026 | F | H | 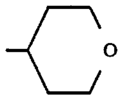 | |
| 5.027 | H | H | 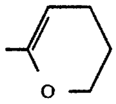 | |
| 5.028 | F | H | 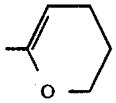 | |
| 5.029 | H | H | 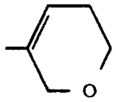 | |
| 5.030 | F | H | 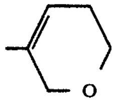 | |
| 5.031 | H | H | 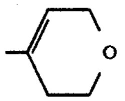 | |
| 5.032 | F | H | 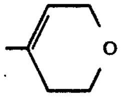 | |
| 5.033 | H | H | 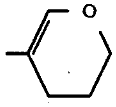 | |
| 5.034 | F | H | 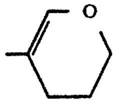 | |
TABLE 5-continued
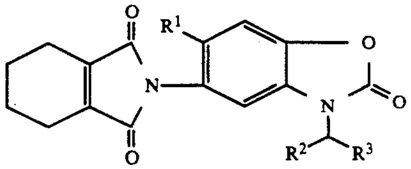
I
| No. | $R^1$ | $R^2$ | $R^3$ | m.p.[°C.] |
| --- | --- | --- | --- | --- |
| 5.035 | H | H | 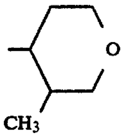 | |
| 5.036 | F | H | 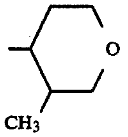 | |
| 5.037 | H | H | 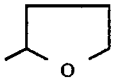 | |
| 5.038 | F | H | 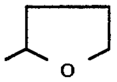 | |
| 5.039 | H | H | 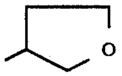 | |
| 5.040 | F | H | 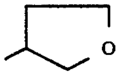 | |
| 5.041 | H | H | 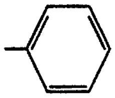 | 206-207 |
| 5.042 | F | H | 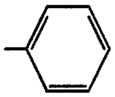 | |
| 5.043 | H | H | 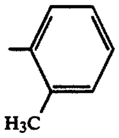 | |
| 5.044 | F | H | 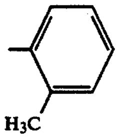 | |
| 5.045 | H | H | 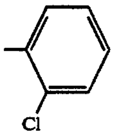 | |

TABLE 5-continued
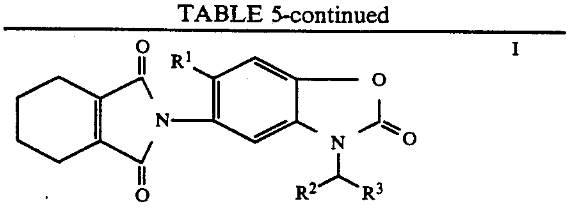
I
| No. | R1 | R2 | R3 | m.p.[°C.] |
|---|---|---|---|---|
| 5.046 | F | H | 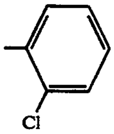 | |
TABLE 6
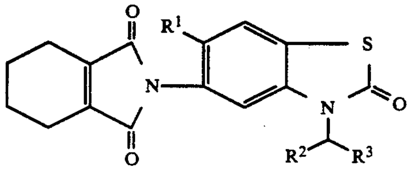
I
| No. | R1 | R2 | R3 | m.p.[°C.] |
|---|---|---|---|---|
| 6.001 | H | H | 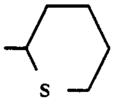 | |
| 6.002 | F | H | 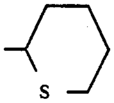 | |
| 6.003 | H | H | 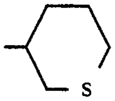 | |
| 6.004 | F | H | 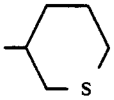 | |
| 6.005 | H | H | 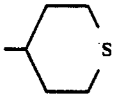 | |
| 6.006 | F | H | 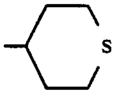 | |
| 6.007 | H | H | 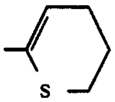 | |
| 6.008 | F | H | 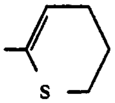 | |
TABLE 6-continued
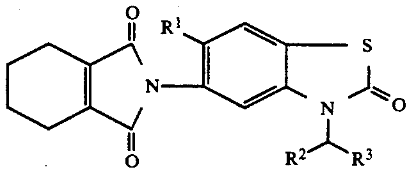
I
| No. | R1 | R2 | R3 | m.p.[°C.] |
|---|---|---|---|---|
| 6.009 | H | H | 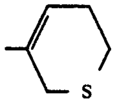 | |
| 6.010 | F | H | 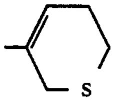 | |
| 6.011 | H | H | 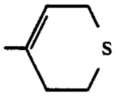 | |
| 6.012 | F | H | 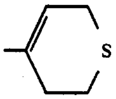 | |
| 6.013 | H | H | 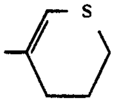 | |
| 6.014 | F | H | 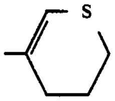 | |
| 6.015 | H | H | 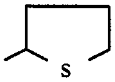 | |
| 6.016 | F | H | 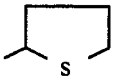 | |
| 6.017 | H | H | 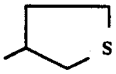 | |
| 6.018 | F | H | 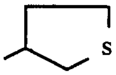 | |
| 6.019 | H | H | 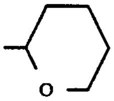 | |
| 6.020 | F | H | 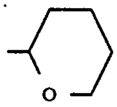 | |

TABLE 6-continued
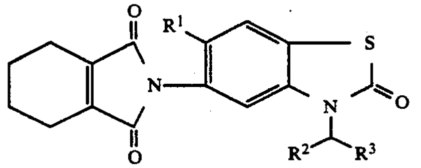
I
| No. | $R^1$ | $R^2$ | $R^3$ | m.p.[°C.] |
|---|---|---|---|---|
| 6.021 | H | H | 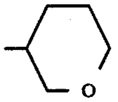 | |
| 6.022 | F | H | 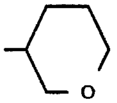 | |
| 6.023 | H | $CH_3$ | 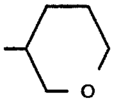 | |
| 6.024 | F | $CH_3$ | 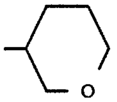 | |
| 6.025 | H | H | 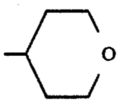 | |
| 6.026 | F | H | 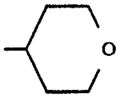 | |
| 6.027 | H | H | 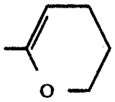 | |
| 6.028 | F | H | 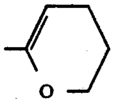 | |
| 6.029 | H | H | 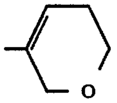 | |
| 6.030 | F | H | 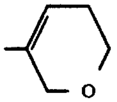 | 187–189 |
| 6.031 | H | H | 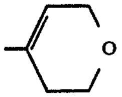 | |
TABLE 6-continued
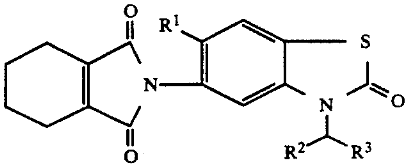
I
| No. | $R^1$ | $R^2$ | $R^3$ | m.p.[°C.] |
|---|---|---|---|---|
| 6.032 | F | H | 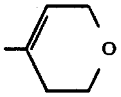 | |
| 6.033 | H | H | 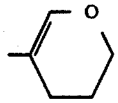 | |
| 6.034 | F | H | 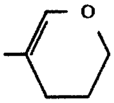 | |
| 6.035 | H | H | 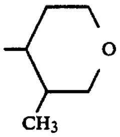 | |
| 6.036 | F | H | 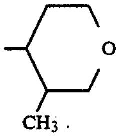 | |
| 6.037 | H | H | 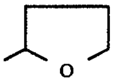 | |
| 6.038 | F | H | 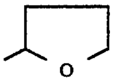 | |
| 6.039 | H | H | 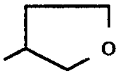 | |
| 6.040 | F | H | 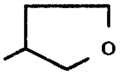 | |
| 6.041 | H | H | 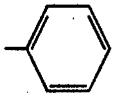 | |
| 6.042 | F | H | 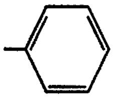 | |

TABLE 6-continued

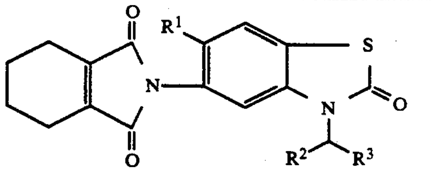

I

| No. | R[1] | R[2] | R[3] | m.p.[°C.] |
|---|---|---|---|---|
| 6.043 | H | H | 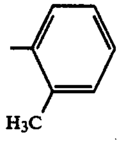 | |
| 6.044 | F | H | 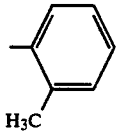 | |
| 6.045 | H | H | 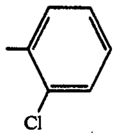 | |
| 6.046 | F | H | 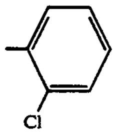 | |

USE EXAMPLES

The action of the N-aryltetrahydrophthalimide compounds of the formula I on plant growth is demonstrated by the following greenhouse experiments:

The vessels employed were plastic flowerpots having a volume of 300 $cm^3$ and filled with a sandy loam containing about 3.0% humus. The seeds of the test plants were sown separately, according to species.

For the postemergence treatment, either plants which had been sown in the pots and grown there were selected, or they were cultivated separately as seedlings and transplanted to the pots a few days before being treated.

Depending on growth form, the plants were grown to a height of from 3 to 15 cm before being treated with the active ingredients which were suspended or emulsified in water and sprayed through finely distributing nozzles. The application rates for postemergence treatment were 0.06 and 0.125 kg of active ingredient per hectare.

The pots were set up in the greenhouse, species from warmer climates in warmer areas (20° to 35° C.) and species from moderate climates at 10 to 20° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

The plants used in the greenhouse experiments were: *Amaranthus retroflexus, Galium aparine, Stellaria media,* Veronica spp., *Oryza sativa, Solanum higrum,* and *Triticum aestivum.*

The compounds 1.027 and 1.029, applied postemergence at rates of 0.06 and 0.125 kg/ha, gave excellent control of unwanted broadleaved plants, and were well tolerated by rice and wheat. Compound 3.067, applied postemergence at a rate of 0.06 kg/ha, combated unwanted broadleaved plants without causing any appreciable damage to rice.

We claim:

1. An N-aryltetrahydrophthalimide compound of the formula I

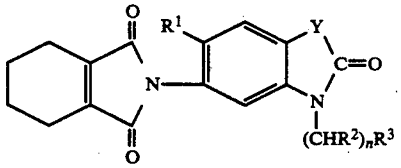

I where the substituents and indices have the following meanings: n is 0 or 1, $R^1$ is hydrogen or halogen, Y is —O— or —S—, $R^2$ is hydrogen or $C_1$-$C_3$-alkyl, and $R^3$ is phenyl which is unsubstituted or monosubstituted to trisubstituted by $C_1$- or $C_2$-alkyl, halogen, methoxy, nitro, and/or cyano.

2. A herbicide containing a herbicidally effective amount of an N-aryltetrahydrophthalimide compound of the formula I as defined in claim 1 and inert additives.

3. A herbicide containing a herbicidally effective amount of an N-aryltetrahydrophthalimide compound of the formula I as defined in claim 1 and further active constituents.

4. A method for controlling undesirable plant growth, wherein the undesirable plants, their habitat or both the undesirable plants and their habitat, are treated with a herbicidally effective amount of an N-aryltetrahydrophthalimide compound of the formula I, as defined in claim 1.

5. An N-aryltetrahydrophthalimide compound of the formula I

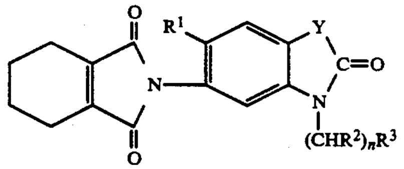

I where the substituents and indices have the following meanings: n is 0 or 1, $R^1$ is hydrogen or halogen, Y is —O— or —S—, $R^2$ is hydrogen or $C_1$–$C_3$-alkyl, and $R^3$ is 2-tetrahydrothiopyranyl, 3-tetrahydrothiopyranyl, 4-tetrahydrothiopyranyl, 5,6-dihydro-2H-thiopyranyl, 2-tetrahydropyranyl, 3-tetrahydropyranyl, 4-tetrahydropyranyl or 5,6-dihydro-2H-pyranyl each of which may be monosubstituted to trisubstituted by $C_1$–$C_3$-alkyl.

6. A herbicide containing a herbicidally effective amount of an N-aryltetrahydrophthalimide compound of the formula I as defined in claim 5 and inert additives.

7. A herbicide containing a herbicidally effective amount of an N-aryltetrahydrophthalimide compound of the formula I as defined in claim 5 and further active constituents.

8. A method for controlling undesirable plant growth, wherein the undesirable plants, their habitat or both the undesirable plants and their habitat, are treated with a herbicidally effective amount of an N-aryltetrahydrophthalimide compound of the formula I, as defined in claim 5.

9. An N-aryltetrahydrophthalimide compound of the formula I

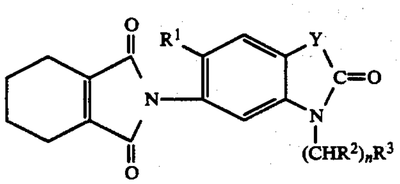

I where the substituents and indices have the following meanings: n is 0 or 1, $R^1$ is hydrogen or halogen, Y is —O— or —S—, $R^2$ is hydrogen or $C_1$–$C_3$-alkyl, and $R^3$ is 2-tetrahydrofuryl, 3-tetrahydrofuryl, 2-tetrahydrothienyl or 3-tetrahydrothienyl each of which may be monosubstituted to trisubstituted by $C_1$–$C_3$-alkyl.

10. A herbicide containing a herbicidally effective amount of an N-aryltetrahydrophthalimide compound of the formula I as defined in claim 9 and inert additives.

11. A herbicide containing a herbicidally effective amount of a N-aryltetrahydrophthalimide compound of the formula I as defined in claim 9 and further active constituents.

12. A method for controlling undesirable plant growth, wherein the undesirable plants, their habitat or both the undesirable plants and their habitat, are treated with a herbicidally effective amount of an N-aryltetrahydrophthalimide compound of the formula I, as defined in claim 9.

* * * * *

UNITED STATES PATENT AND TRADEMARK OFFICE
CERTIFICATE OF CORRECTION

PATENT NO. : 5,213,605

DATED : May 25, 1993

INVENTOR(S) : RUEB et al.

It is certified that error appears in the above identified patent and that said Letters Patent is hereby corrected as shown below:

Column 130:

Claim 1, line 25, delete "to" and substitute --or--.

Claim 5, line 60, delete "to" and substitute --or--.

Signed and Sealed this

Twenty-second Day of February, 1994

Attest:

BRUCE LEHMAN

Attesting Officer

Commissioner of Patents and Trademarks